(12) United States Patent
Dunham et al.

(10) Patent No.: US 11,140,883 B2
(45) Date of Patent: Oct. 12, 2021

(54) GENE EDITING OF REPRODUCTIVE HORMONES TO STERILIZE AQUATIC ANIMALS

(71) Applicant: AUBURN UNIVERSITY, Auburn, AL (US)

(72) Inventors: Rex A. Dunham, Auburn, AL (US); Zhenkui Qin, Auburn, AL (US); Guyu Qin, Auburn, AL (US)

(73) Assignee: AUBURN UNIVERSITY, Auburn, AL (US)

( * ) Notice: Subject to any disclaimer, the term of this patent is extended or adjusted under 35 U.S.C. 154(b) by 152 days.

(21) Appl. No.: 15/614,356

(22) Filed: Jun. 5, 2017

(65) Prior Publication Data

US 2018/0064077 A1    Mar. 8, 2018

Related U.S. Application Data

(60) Provisional application No. 62/345,163, filed on Jun. 3, 2016.

(51) Int. Cl.
| | |
|---|---|
| *A01K 67/027* | (2006.01) |
| *C12N 15/85* | (2006.01) |
| *C12N 9/22* | (2006.01) |
| *C07K 14/46* | (2006.01) |
| *C12N 15/10* | (2006.01) |
| *C12N 15/90* | (2006.01) |

(52) U.S. Cl.
CPC ........ *A01K 67/0276* (2013.01); *C07K 14/461* (2013.01); *C12N 9/22* (2013.01); *C12N 15/102* (2013.01); *C12N 15/8509* (2013.01); *C12N 15/90* (2013.01); *A01K 2217/00* (2013.01); *A01K 2217/075* (2013.01); *A01K 2227/40* (2013.01); *A01K 2267/02* (2013.01)

(58) Field of Classification Search
CPC ............ A01K 67/0276; A01K 2217/00; A01K 2227/40; C12N 15/8509
USPC ........................................................ 800/20
See application file for complete search history.

(56) References Cited

PUBLICATIONS

Zhang (Mol Endocrinol. Jan. 2015; 29(1): 76-98).*
Qin (A dissertation submitted to the Graduate Faculty of Auburn University in partial fulfillment of the requirements for the Degree of Doctor of Philosophy Auburn, Alabama Dec. 12, 2015).*
Weil, C., Bougoussa-Houadec, M., Gallals, C., Itoh, S., Sekine, S. & Valotalre, Y. (1995). Preliminary evidence suggesting variations of GtH 1 and GtH 2 mRNA levels at different stages of gonadal development in rainbow trout, Oncorhynchus mykiss. General and comparative endocrinology, 100: 327-333.
Yano, A.,Guyomard, R., Nicol, B.,Jouanno, E.,Quillet, E.,Klopp, C.,Cabau, C.,Bouchez, O.,Fostier, A. & Gulguen, Y. (2012). An immune-related gene evolved Into the master sex-determining gene In rainbow trout, Oncorhynchus mykiss. Current Biology, 22: 1423-1428.
Yano, A., Nicol, B., Jouanno, E. & Guiguen, Y. (2014). Heritable Targeted Inactivation of the Rainbow Trout (Oncorhynchus mykiss) Master sex-Determining Gene Using Zinc-Finger Nucleases. Marine biotechnology,16: 243-250.
Yaron, Z., Gur, G., Melamed, P., Rosenfeld, H.,Elizur, A. & Levavi-Sivan, B. (2003). Regulation of fish gonadotropins. International review of cytology, 225: 131-185.
Yoshiura, Y., Kobayashi,M., Kato, Y. & Aida, K. (1997). Molecular cloning of the cDNAs encoding two gonadotropin 13 subunits (GTH-113 and-1113) from the goldfish, Carassius auratus. General and comparative endocrinology,105: 379-389.
Young, J.J., Cherone, J.M., Doyon, Y., Ankoudinova, I., Faraji, F.M., Lee, A.H., Ngo, C., Guschin, D.Y., Paschon, D.E. &Miller, J.C. (2011). Efficient targeted gene disruption in the soma and germ line of the frog Xenopus tropicalis using engineered zinc-finger nucleases. Proceedings of the National Academy of Sciences, 108: 7052-7057.
Zhang, X., Guan, G.,Chen, J., Naruse, K. & Hong, Y. (2014). Parameters and efficiency of direct gene disruption by zinc finger nucleases in medaka embryos. Marine biotechnology, 16: 125-134.
Zahar,Y., Munoz-Cueto,J.A.,Elizur,A. & Kah, O. (2010). Neuroendocrinology of reproduction in teleost fish. General and comparative endocrinology, 165: 438-55.
Amano, M., Oka, Y., Yamanome, T., Okuzawa, K. & Yamamori, K. (2002). Three GnRH systems In the brain and pituitary of a pleuronectiform fish, the barfin flounder Verasper moseri. Cell and tissue research, 309: 323-9.
Ansai,S., Ochiai,H., Kanle, Y., Kamei,Y., Gou, Y., Kitano,T. ,Yamamoto, T.& Kinoshita, M. (2012). Targeted disruption of eogenous EGFP gene in medaka using zinc-finger nucleases. Development, growth & differentiation,54: 546-556.
Bart, A. & Dunham, R. (1996). Effects of sperm concentration and egg number on fertilization efficiency with channel catfish (Ictalurus punctatus) eggs and blue catfish {I. furcatus) spermatozoa. Therlogenology, 45:673-682.
Beumer, K.J.,Trautman, J.K., Bozas, A., Liu, J.L., Rutter,J., Gall, J.G. & Carroll, D. (2008). Efficient gene targeting in Drosophila by direct embryo Injection with zinc-finger nucleases. Proceedings of the National Academy of Sciences of the United States of America, 105: 19821-19826.
Bibikova, M., Golie, M., Golie, K.G. & Carroll, D. (2002). Targeted chromosomal cleavage and mutagenesis In Drosophila using zinc-finger nucleases. Genetics, 161: 1169-1175.
Carbery, I.D., Ji, D., Harrington, A., Brown, V., Weinstein, E.J., Liaw, L. & Cui, X. (2010), Targeted genome modification in mice using 2inc-flnger nucleases. Genetics, 186: 451-459.

(Continued)

Primary Examiner — Valarie E Bertoglio
(74) Attorney, Agent, or Firm — Quarles & Brady LLP

(57) ABSTRACT

Disclosed are fish with impaired reproductive capacity and methods and compositions for producing the same. The reproductively impaired fish may include catfish, such as Ictalurus punctatus. The disclosed methods may be generally useful for mitigating environmental impact of escaped genetically engineered fish.

12 Claims, 27 Drawing Sheets
Specification includes a Sequence Listing.

(56) References Cited

PUBLICATIONS

Cathomen, T. & Joung, J.K. (2008). Zinc-finger nucleases: the next generation emerges. Molecular Therapy, 16: 1200-1207.

Chen, S.,Oikonomou, G.,Chiu, C.N., Niles, B.J.,Liu, J., ee, D.A., Antoshechkln, I. & Prober, D.A. (2013). A large-scale in vivo analysis reveals that TALENs are significantly more mutagenic than ZFNs generated using context-dependent assembly. Nucleic Acids Res, 41:2769-2778.

Collares, T., Campos, V.F., Seixas, F.K.,Cavalcanti, P.V., Dellagostin, O.A., Moreira, H.I.M. & Deschamps, J.C. (2010). Transgene transmission in South American catfish (*Rhamdia quelen*) larvae by sperm-mediated gene transfer. Journal of biosciences, 35: 39-47.

Cornu, T.I., Thibodeau-Beganny, S., Guhl, E.,Alwin,S., Eichtinger,M., Joung, J. & Cathomen, T. (2008). DNA-binding specificity Is a major determinant of the activity and toxicity of zinc-finger nucleases. Molecular Therapy,16: 352-358.

Cui, X., Ji, D., Fisher, D.A., Wu, V., Briner, D.M. & Weinstein, E.J. (2011). Targeted integration in rat and mouse embryos with zinc-finger nucleases. Nature biotechnology, 29: 64-7.

Doyon,Y., Mccammon,J.M., Miller,J.C., Farajl, F., Ngo, C., Katibah, G.E.,Amora, R., Hocking, T.D., Zhang, L., Rebar, E.J., Gregory, P.O.,Urnov,F.D. & Amacher,S.L. (2008). Heritable targeted gene disruption In zebrafish using designed zinc-finger nucleases. Nature biotechnology, 26: 702-708.

Dunham, R.A. (2011). Aquaculture and fisheries biotechnology : genetic approaches, Wallingford, Oxfordshire, UK ; Cambridge, MA.

Dunham, R.A., Majumdar, K., Hallerman, E., Bartley, D., Mair; G., Hulata, G., Liu, Z., Pongthana, N., Bakos, J. & Penman, D. (2000). Review of the status of aquaculture genetics. Aquaculture in the Third Millennium Technical Proceedings of the Conference on Aquaculture in the Third Millennium, Bangkok, Thailand.

Dunham, R.A. & Smitherman, R.O. (1984). Ancestry and breeding of catfish in the United States.

Flisikowska, T., Thorey, 1.s., Offner, s., Ros, F., Lifke, V.,Zeitler,B., Rottmann, 0. Vincent, A.,Zhang, L. & Jenkins, s. (2011). Efficient immunoglobulin gene disruption and targeted replacement in rabbit using zinc finger nucleases. PloS one, 6: e21045.

Foley,J.E., Yeh, J.R.J., Maeder, M.L., Reyon, D., Sander, J.D.. Peterson, R.T. & Joung, J.K. (2009). Rapid Mutation of Endogenous Zebrafish Genes Using Zinc Finger Nucleases Made by Oligomerized Pool Engineering (OPEN). PloS one, 4: e4348.

Geurts, A.M., Cost, G.J., Freyvert, Y., Zeitler, B., Miller, J.C., Choi,V.M.,Jenkins, S.S., Wood, A.,Cui, X. & Meng, X. (2009). Knockout rats via embryo microinjection of zinc-finger nucleases. Science, 325: 433-433.

Gupta, A., Christensen, R.G., Rayla, A.L., Lakshmanan, A., Stormo, G.D. & Wolfe, S.A. (2012). An optimized two-finger archive for ZFN-mediated gene targeting. Nature methods, 9: 588-90.

Gupta, A.,Meng, X., Zhu, L.J., Lawson, N.D. & Wolfe, S.A. (2011). Zinc finger protein-dependent and -independent contributions to the in vivo off-target activity of zinc finger nucleases. Nucleic Acids Res, 39: 381-92.

Hanson, T.& Sites, D. (2012). 2011 US catfish database. Fisheries.
Hanson,T. & Sites, D. (2013). 2012 US catfish database. Fisheries.

Hassin, S.. Claire, M., Holland, H. & Zahar, Y. (2000). Early maturity In the male striped bass, *Morone saxatilis*: follicle-stimulating hormone and luteinizing hormone gene expression and their regulation by gonadotropin-releasing hormone analogue and testosterone. Biology of reproduction, 63: 1691-1697.

Hsu, S.Y.,Nakabayashi, K. & Bhalla, A. (2002). Evolution of glycoprotein hormone subunit genes in bilateral metazoa: identification of two novel human glycoprotein hormone subunit family genes, GPA2 and GPB5. Molecular endocrinology, 16: 1538-51.

Kagawa, H., Gen, K., Okuzawa, K. & Tanaka, H. (2003). Effects of luteinizing hormone and follicle-stimulating hormone and insulin-like growth factor-I on aromatase activity and P450 aromatase gene expression in the ovarian follicles of red seabream, *Pagrus major*. Biology of reproduction, 68: 1562-1568.

Kagawa, H., finuma, N., Tanaka, H., Ohta, H. & Okuzawa, K. (1998a). Effects of Rearing Period in Seawater on Induced Maturation In Female Japanese Eel *Anguilla japonica*. Fisheries science, 64: 77-82.

Kagawa, H.,Tanaka, H.,Okuzawa, K. & Kobayashi,M. (1998b). GTH II but not GTH I induces final maturation and the development of maturational competence of oocytes of red seabreamin vitro. General and comparative endocrinology, 112: 80-88.

Kajimura, S.,Yoshiura, V., Suzuki,M.,Utoh, T., Harle, N.,Oka, H. & Aida, K. (2001). Changes In the levels of mRNA coding for gonadotropin Iand IIB subunits during vitellogenesis in the common Japanese conger *Conger myriaster*. Fisheries science, 67: 1053-1062.

Kang, J.-H., Voshizaki, G., Homma, O., Strussmann, C.A. & Takashima, F. (1999). Effect of an osmotic differential on the efficiency of gene transfer by electroporation of fish spermatozoa. Aquaculture, 173: 297-307.

Kurita, K., Burgess, S.M. & Sakai,N. (2004). Transgenic zebrafish produced by retroviral infection of in vitro-cultured sperm. Proceedings of the National Academy of Sciences of the United States of America, 101:1263-1267.

Liu, Z., Kim, S. & Karsi, A. (2001). Channel catfish follicle-stimulating hormone and luteinizing hormone complementary DNA cloning and expression during ovulation. Marine biotechnology, 3: 590-599.

Mashimo, T., Taklzawa, A.,Voigt, B.,Yoshiml,K.,Hlai,H.,Kuramoto, T.& Serikawa, T.(2010). Generation of knockout rats with X-linked severe combined immunodeficiency (X-SCID) using zinc-finger nucleases. PloS one, 5:e8870.

Meng, X.,Noyes, M.B., Zhu, L.J., Lawson, N.D. & Wolfe, S.A. (2008). Targeted gene inactivation in zebrafish using engineered zinc-finger nucleases. Nature biotechnology, 26: 695-701.

Miller, J.C., Holmes, M.C., Wang, J., Guschin, D.Y., Lee, Y.L., Rupniewski, I., Beausejour, C.M., Waite, A.J.,Wang, N. S.,Kim, K.A., Gregory, P.D., Pabo, C.O. & Rebar, E.J. (2007). An improved zinc-finger nuclease architecture for highly specific genome editing. Nature biotechnology, 25: 778-85.

Moore, F.E.,Reyon, D.,Sander,J.D., Martinez, S.A., Blackburn, J.S. ,Khayter,C., Ramirez, C.L.,Joung, J.K. & Langenau, D.M. (2012). Improved somatic mutagenesis In zebrafish using transcription activator-like effector nucleases (TALENs). PloS one, 7: e37877.

Naito, N., Hyodo, S., Okumoto, N., Urano, A. & Nakai, V. (1991). Differential production and regulation of gonadotropins (GTH I and GTH II) in the pituitary gland of rainbow trout, *Oncorhynchus mykiss*, during ovarian development. Cell and tissue research, 266: 457-467.

Nakajima, K.,Nakajima, T.,Takase, M. & Yaoita, Y.(2012). Generation of albino Xenopus tropicalis using zinc-finger nucleases. Development, growth & differentiation, 54: 777-784.

Ochiat, H., Fujita, K., Suzuki, K.T., Nishikawa, M., Shibata, T., Sakamoto, N. & Yamamoto, T. (2010). Targeted mutagenesis in the sea urchin embryo using zinc-finger nucleases. Developmental biology, 344: 487-487.

Okada, T., Kawazoe, I., Kimura, S., Sasamoto,Y.,Aida, K & Kawauchi, H. (1994). Purification and characterization of gonadotropin I and II from pituitary glands of tuna (*Thunnus obesus*). International journal of peptide and protein research, 43: 69-80.

Pattanayak, V., Ramirez, C.L., Joung, J.K. & Liu,D.R. (2011). Revealing off-target cleavage specificities of zinc-finger nucleases by in vitro selection. Nature methods, 8: 765-770.

Perez-Pinera, P., Ousterout, D.G.,Brown,M.T.& Gersbach, C.A. (2012). Gene targeting to the ROSA26 locus directed by engineered zinc finger nucleases. Nucleic Acids Res, 40: 3741-3752.

Pierce, J.G. & Parsons, T.F. (1981). Glycoprotein hormones: structure and function. Annual review of biochemistry, 50: 465-495.

Planas, J.V. & Swanson, P. (1995). Maturation-associated changes in the response of the salmon testis to the steroidogenic actions of gonadotropins (GTH Iand GTH II) In vitro. Biology of reproduction, 52: 697-704.

Porteus, M.H. & Baltimore, D. (2003). Chimeric nucleases stimulate gene targeting in human cells. Science, 300: 763-763.

(56) References Cited

PUBLICATIONS

Su, B. (2012). Reproductive confinement of common carp, *Cyprinus carpio*, and channel catfish, *Ictalurus punctatus*, via transgenic sterilization. Doctoral Dissertation, Auburn University, Alabama, USA.

Suzuki, K., Kawauchi, H. & Nagahama, V. (1988). Isolation and characterization of two distinct gonadotropins from chum salmon pituitary glands. General and comparative endocrinology, 71:292-301.

Swanson, P., Suzuki, K., Kawauchi, H. & Dickhoff, W.W. (1991). Isolation and characterization of two coho salmon gonadotropins, GTH I and GTH II. Biology of reproduction, 44: 29-38.

Taibi, A., Mandavawala, K.P., Noel, J., Okoye, E.V., Milano, C.R., Martin, B.L. & Sirotkin, H.I. (2013). Zebrafish churchill regulates developmental gene expression and cell migration. Developmental Dynamics, 242: 614-621.

Urnov, F.D., Miller, J.C., Lee, V.L., Beausejour, C.M., Rock, J.M., Augustus, S., Jamieson, A.C., Porteus, M.H., Gregory, P.D. & Holmes, M.C. (2005). Highly efficient endogenous human gene correction using designed zinc-finger nucleases. Nature, 435: 646-651.

Van Der Kraak, G., Suzuki, K., Peter, R.E., Itoh, H. & Kawauchi, H. (1992). Properties of common carp gonadotropin I and gonadotropin II. General and comparative endocrinology, 85: 217-229.

Bodnar, Anastasia, Fast-growing genetically engineered salmon approved, Biology Fortified, Mar. 12, 2019.

Devlin, Robert H., et al., Sex determination and sex differentiation in fish: an overview of genetic, physiological, and environmental influences, Aquaculture, Jun. 21, 2002, pp. 191-364, vol. 208, Nos. 3-4.

Bao, Lisui, et al., The Y chromosome sequence of the channel catfish suggests novel sex dewtermination mechanisms in teleost fish, BMC Biology, 2019, pp. 1-16, vol. 17, No. 6.

Marris, Emma, Transgenic fish go large, Nature, Sep. 16, 2010, p. 259, vol. 467.

\* cited by examiner

1) ZFN set1   (SEQ ID NO:1)

CACAGAAACAGTCTCATTAACAGGTTCGCAGTGTGGCA

2) ZFN set2   (SEQ ID NO:2)

CTCATTAACAGGTTCGCAGTGTGGCAGAATGTAGCT

3) ZFN set3   (SEQ ID NO:3)

CTCATTAACAGGTTCGCAGTGTGGCAGAATGTAGCTTTGAGCG (SEQ ID NO:34) TTTCTTCTCCTG-TG--TTTCTTGATGAAC  wt
(SEQ ID NO:35) TTTCTTCTCCTGGTG--TTTCTTGATGAAC ⎤
(SEQ ID NO:36) TTTCTTCTCCTG-TGU-TTTCTTGATGAAC ⎥ 1 bp insertion
(SEQ ID NO:37) TTTCTTCTCCTG-TGT-TTTCTTGATGAAC ⎥
(SEQ ID NO:38) TTTCTTCTCCTGATG--TTTCTTGATGAAC ⎦
(SEQ ID NO:39) TTTCTTCTCCTGGTGG-TTTCTTGATGAAC ⎤
(SEQ ID NO:40) TTTCTTCTCCTGATGG-TTTCTTGATGAAC ⎬ 2 bp insertion
(SEQ ID NO:41) TTTCTTCTCCTG-TGTGTTTCTTGATGAAC ⎦
(SEQ ID NO:42) TTTCTCCTCCTG-TG--TTTCTTGATGAAC  Substitution
(SEQ ID NO:43) TTTCTTCTCCTG-----TTTCTTGATGAAC  Deletion
(SEQ ID NO:44) TTTCTCCTCCTGGTG--TTTCTTGATGAAC  Complex

FIG. 7

1) LH_XTN (SEQ ID NO:4)

TCTTGATGAACTCCTTCTCCCCCGCTCAAAGCTACATTCTGCCACACTGCGA

2) FSH_XTN (SEQ ID NO:5)

TACCAACATCTCCATCACCGTGGAGAGCGACGAGTGTGGCAGCTGCATCA

3) GnRH_XTN (SEQ ID NO:6)

TTCACCTCGGAATAAACTCTACAGGCTGAAAGATCTGCTGGTGCACAGCTCA

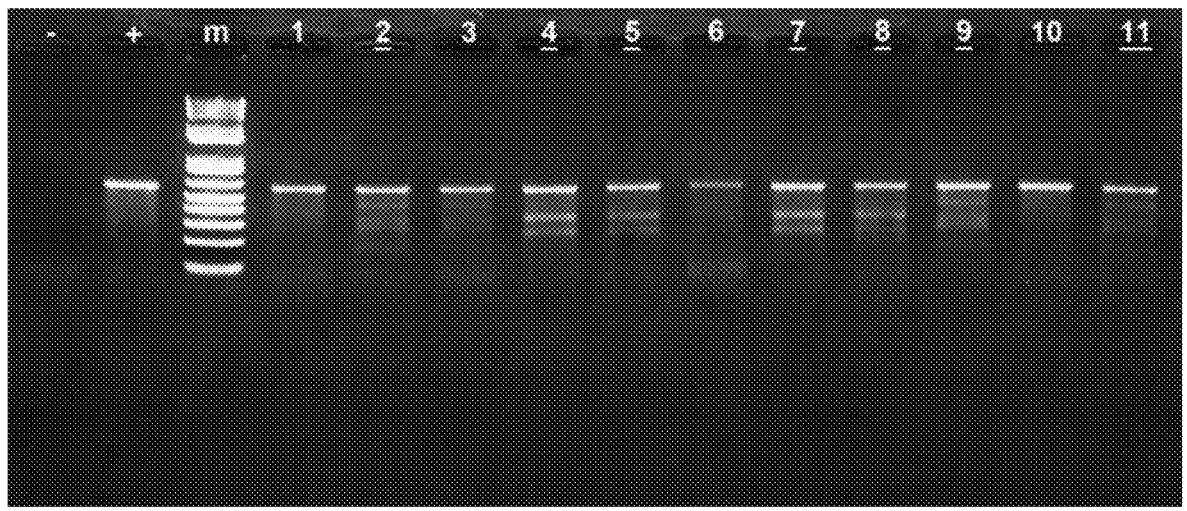

FIG. 14

(SEQ ID NO:46) GTTCTTGATGAACTCCTTCTCCCCCGTCAAAGCTACATTCTGCCACACTGCGAACCT   wt
(SEQ ID NO:47) GTTCTTGATGAACTCCTTCTCCCCG-TCAAAGCTACATTCTGCCACACTGCGAACCT
(SEQ ID NO:48) GTTCTTGATGAACTCCTTCTCC--GCTCAAAGCTACATTCTGCCACACTGCGAACCT
(SEQ ID NO:49) GTTCTTGATGAACTCCTTCTCCC---TCAAAGCTACATTCTGCCACACTGCGAACCT   Deletion
(SEQ ID NO:50) GTTCTTGATGAACTCCTTCTC----GCTCAAAGCTACATTCTGCCACACTGCGAACCT
(SEQ ID NO:51) GTTCTTGATGAACTCCTTCTCC-----TCAAAGCTACATTCTGCCACACTGCGAACCT
(SEQ ID NO:52) GTTCTTGATGAACTCCTTCTCCCCCGTCTAAGCTACATTCTGCCACACTGCGAACCT   Substitution
(SEQ ID NO:53) GTTCTTGATGAACTCCTTCTCCCCCGATCAAAGCTACATTCTGCCACACTGCGAACCT
(SEQ ID NO:54) GTTCTTGATGAACTCCTTCTCCCCCGGCTCAAAGCTACATTCTGCCACACTGCGAACCT   Insertion

FIG. 15

(SEQ ID NO:55) GTCTTACCAACATCTCCATCACCGTGGAGAGCGACGAGTGTGGCAGCTGCATCACTG   wt
(SEQ ID NO:56) GTCTTACCAACATCTCCATCACCGTGGA--GCGACGAGTGTGGCAGCTGCATCACTG ⎫
(SEQ ID NO:57) GTCTTACCAACATCTCCATCACCGTG---AGCGACGAGTGTGGCAGCTGCATCACTG ⎬ Deletion
(SEQ ID NO:58) GTCTTACCAACATCTCCATCACCG----GAGCGACGAGTGTGGCAGCTGCATCACTG ⎪
(SEQ ID NO:59) GTCTTACCAACATCTCCATCACCGTGGA----GACGAGTGTGGCAGCTGCATCACTG ⎭
(SEQ ID NO:60) GTCTTACCAACATCTCCATCACCGTGGAGAGCGCGAGTGTGGCAGCTGCATCACTG ⎫ Substitution
(SEQ ID NO:61) GTCTTACCAACATCTCCATCACCGTGGAGAGCGGCGAGTGTGGCAGCTGCATCACTG ⎭
(SEQ ID NO:62) GTCTTACCAACATCTCCATCACCGTGGACTGGAGCGACGAGTGTGGCAGCTGCATCACTG ⎫ Insertion
(SEQ ID NO:63) GTCTTACCAACATCTCCATCACCGTGGAGAGCGACGAGTGCGGTGTGGCAGCTGCATCACTG ⎭

FIG. 16

(SEQ ID NO:64) TGTTTCACCTCGGAATAAACTCTACAGGCTGAAAGATCTGCTGGTGCACAGCTCATAAT   wt
(SEQ ID NO:65) TGTTTCACCTCGGAATAAACTCT--AGGCTGAAAGATCTGCTGGTGCACAGCTCATAAT ⎫
(SEQ ID NO:66) TGTTTCACCTCGGAATAAACTCT---GGCTGAAAGATCTGCTGGTGCACAGCTCATAAT ⎬ Deletion
(SEQ ID NO:67) TGTTTCACCTCGGAATAAACTCTACAG--GAAAGATCTGCTGGTGCACAGCTCATAAT ⎪
(SEQ ID NO:68) TGTTTCACCTCGGAATAAACTCTA-----TGAAAGATCTGCTGGTGCACAGCTCATAAT ⎭
(SEQ ID NO:69) TGTTTCACCTCGGAATAAACTCTACAAGCTGAAAGATCTGCTGGTGCACAGCTCATAAT ⎫ Substitution
(SEQ ID NO:70) TGTTTCACCTCGGAATAAACTCTACAGCTGATAGATCTGCTGGTGCACAGCTCATAAT ⎭
(SEQ ID NO:71) TGTTTCACCTCGGAATAAACTCTACAGGGCTGAAAGATCTGCTGGTGCACAGCTCATAAT   Insertion

FIG. 17

1) LH sgRNA target sequence    (SEQ ID NO:7)

CCTTCTCCCCCGCTCAAAGCTACATTCTGCCACACTGCGAACCT

2) GnRH sgRNA target sequence    (SEQ ID NO:8)

TGCCGAGGACCTCCGGCTACGTGTGTGATTACGTAGATGTTCA

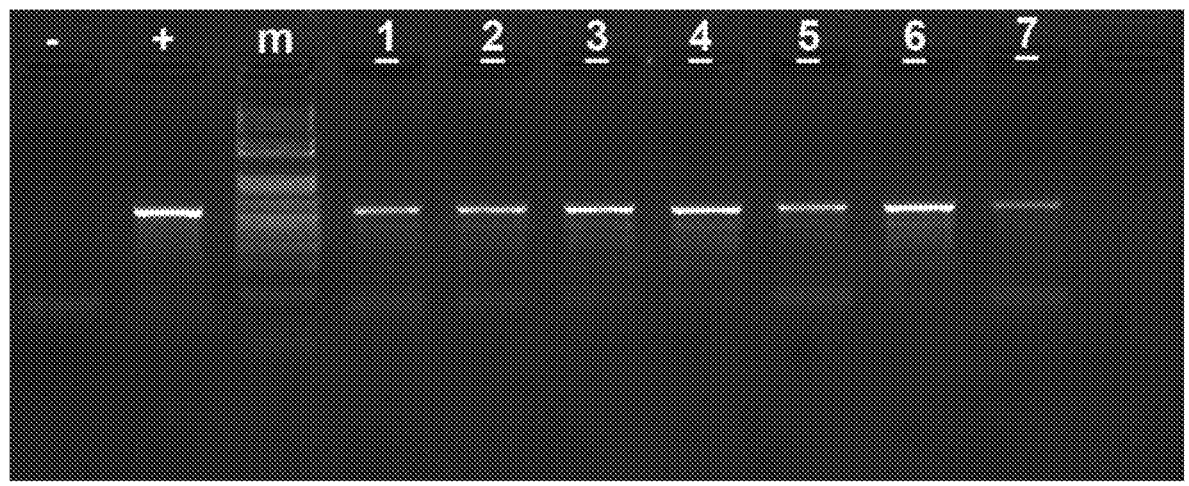

FIG. 29

```
TGAACTCCTTCTCCCCGCTCAAAGCTACATTCTGCCACACTGCGAACC    wt
  (SEQ ID NO:72)
TGAACTCCTTCTCCCCGCTCAAAGCTACATTC-GCCACACTGCGAACC
  (SEQ ID NO:73)
TGAACTCCTTCTCCCCGCTCAAAGCTACATTCT--CACACTGCGAACC
  (SEQ ID NO:74)
TGAACTCCTTCTCCCCGCTCAAAGCTACATT----CACACTGCGAACC    deletion
  (SEQ ID NO:75)
TGAACTCCTTCTCCCCGCTCAAAGCTACATT------CACTGCGAACC
  (SEQ ID NO:76)
TGAACTCCTTCTCCCCGCTCAAAGC-------GCCACACTGCGAACC
  (SEQ ID NO:77)
```

FIG. 30

GAAATGCCGAGGACCTCCGGCTACGTGTGTGATTACGTAGATGTTTCAC    wt
(SEQ ID NO:78)

GAAATGCCGAGGACCTCCGGCTAGTGTGTGG--TACGTAGATGTTTCAC  ⎫
(SEQ ID NO:79)                                     ⎪
GAAATGCCGAGGACCTCCGGCTAGTTGTGTGA--ACGTAGATGTTTCAC  ⎬ deletion
(SEQ ID NO:80)                                     ⎪
GAAATGCCGAGGACCTCCGGCTAGTTGTG----ACGTAGATGTTTCAC   ⎭
(SEQ ID NO:81)

FIG. 31

(SEQ ID NO:82)  GAAATGCCGAGGACCTCCGGCTACGTGTGTGATTACGTAGATGTTTCAC    wt
(SEQ ID NO:83)  GAAATGCCGAGGACCTCCGGCTACGTGTG-TTACGTAGATGTTTCAC    ⎫
(SEQ ID NO:84)  GAAATGCCGAGGACCTCCGGCTACGTGTG--ATTACGTAGATGTTTCAC  ⎪
(SEQ ID NO:85)  GAAATGCCGAGGACCTCCGGCTACGTGTGTG--TACGTAGATGTTTCAC  ⎬ Deletion
(SEQ ID NO:86)  GAAATGCCGAGGACCTCCGGCTACGTGTGTGTTACGTAGATGTTTCAC   ⎭
(SEQ ID NO:87)  GAAATGCCGAGGACCTCCGGCTACGTGTGTGATATTACGTAGATGTTTCAC ⎫ Substitution
(SEQ ID NO:88)  GAAATGCCGAGGACCTCCGGCTACGTGTGTGATCTTACGTAGATGTTTCAC ⎭ Insertion

FIG. 32

| | | |
|---|---|---|
| (SEQ ID NO:97) | 1 | ATG AAC TCC TTC TCC CCC GCT CAA AGC TAC ATT CTG CCA CAC TGC  45 |
| | 1 | Met Asn Ser Phe Ser Pro Ala Gln Ser Tyr Ile Leu Pro His Cys  15 |
| (SEQ ID NO:98) | 1 | ATG AAC TCC TTC TCC CCC GTC AAA GCT ACA TTC TGC CAC ACT GCG  45 |
| | 1 | Met Asn Ser Phe Ser Pro Val Lys Ala Thr Phe Cys His Thr Ala  15 |
| (SEQ ID NO:99) | 1 | ATG AAC TCC TTC TCC GCT CAA AGC TAC ATT CTG CCA CAC TGC GAA  45 |
| | 1 | Met Asn Ser Phe Ser Ala Gln Ser Tyr Ile Leu Pro His Cys Glu  15 |
| (SEQ ID NO:100) | 1 | ATG AAC TCC TTC TCC CCT CAA AGC TAC ATT CTG CCA CAC TGC GAA  45 |
| | 1 | Met Asn Ser Phe Ser Pro Gln Ser Tyr Ile Leu Pro His Cys Glu  15 |
| (SEQ ID NO:101) | 1 | ATG AAC TCC TTC TCC CTC AAA GCT ACA TTC TGC CAC ACT GCG AAC  45 |
| | 1 | Met Asn Ser Phe Ser Leu Lys Ala Thr Phe Cys His Thr Ala Asn  15 |
| (SEQ ID NO:102) | 1 | ATG AAC TCC TTC TCC TCA AAG CTA CAT TCT GCC ACA CTG CGA ACC  45 |
| | 1 | Met Asn Ser Phe Ser Ser Lys Leu His Ser Ala Thr Leu Arg Thr  15 |
| (SEQ ID NO:103) | 1 | ATG AAC TCC TTC TCC CCC GCT CTA AGC TAC ATT CTG CCA CAC TGC  45 |
| | 1 | Met Asn Ser Phe Ser Pro Ala Leu Ser Tyr Ile Leu Pro His Cys  15 |
| (SEQ ID NO:104) | 1 | ATG AAC TCC TTC TCC CCC GCA TCA AAG CTA CAT TCT GCC ACA CTG  45 |
| | 1 | Met Asn Ser Phe Ser Pro Ala Ser Lys Leu His Ser Ala Thr Leu  15 |
| (SEQ ID NO:105) | 1 | ATG AAC TCC TTC TCC CCC CGC TCC AAA GCT ACA TTC TGC CAC ACT  45 |
| | 1 | Met Asn Ser Phe Ser Pro Arg Ser Lys Ala Thr Phe Cys His Thr  15 |

FIG. 37

| | | | | | | | | | | | | | | | |
|---|---|---|---|---|---|---|---|---|---|---|---|---|---|---|---|
| (SEQ ID NO:106) | 1 | ATG | TCA | GTG | CCA | GCT | TCC | TCT | TTT | CTT | CTC | CTG | TGT | TTC | TTG ATG | 45 |
| | 1 | Met | Ser | Val | Pro | Ala | Ser | Ser | Phe | Leu | Leu | Leu | Cys | Phe | Leu Met | 15 |
| (SEQ ID NO:107) | 1 | ATG | TCA | GTG | CCA | GCT | TCC | TCT | TTT | CTT | CTC | CTG | GTG | TTT | CTT GAT | 45 |
| | 1 | Met | Ser | Val | Pro | Ala | Ser | Ser | Phe | Leu | Leu | Leu | Val | Phe | Leu Asp | 15 |
| (SEQ ID NO:108) | 1 | ATG | TCA | GTG | CCA | GCT | TCC | TCT | TTT | CTT | CTC | CTG | TGG | TTT | CTT GAT | 45 |
| | 1 | Met | Ser | Val | Pro | Ala | Ser | Ser | Phe | Leu | Leu | Leu | Trp | Phe | Leu Asp | 15 |
| (SEQ ID NO:109) | 1 | ATG | TCA | GTG | CCA | GCT | TCC | TCT | TTT | CTT | CTC | CTG | TGT | TTT | CTT GAT | 45 |
| | 1 | Met | Ser | Val | Pro | Ala | Ser | Ser | Phe | Leu | Leu | Leu | Cys | Phe | Leu Asp | 15 |
| (SEQ ID NO:110) | 1 | ATG | TCA | GTG | CCA | GCT | TCC | TCT | TTT | CTT | CTC | CTG | ATG | TTT | CTT GAT | 45 |
| | 1 | Met | Ser | Val | Pro | Ala | Ser | Ser | Phe | Leu | Leu | Leu | Met | Phe | Leu Asp | 15 |
| (SEQ ID NO:111) | 1 | ATG | TCA | GTG | CCA | GCT | TCC | TCT | TTT | CTT | CTC | CTG | GTG | GTT | TCT TGA | 45 |
| | 1 | Met | Ser | Val | Pro | Ala | Ser | Ser | Phe | Leu | Leu | Leu | Val | Val | Ser * | 15 |
| (SEQ ID NO:112) | 1 | ATG | TCA | GTG | CCA | GCT | TCC | TCT | TTT | CTT | CTC | CTG | ATG | GTT | TCT TGA | 45 |
| | 1 | Met | Ser | Val | Pro | Ala | Ser | Ser | Phe | Leu | Leu | Leu | Met | Val | Ser * | 15 |
| (SEQ ID NO:113) | 1 | ATG | TCA | GTG | CCA | GCT | TCC | TCT | TTT | CTC | CTC | CTG | TGT | GTT | TCT TGA | 45 |
| | 1 | Met | Ser | Val | Pro | Ala | Ser | Ser | Phe | Leu | Leu | Leu | Cys | Val | Ser * | 15 |
| (SEQ ID NO:114) | 1 | ATG | TCA | GTG | CCA | GCT | TCC | TCT | TTT | CTC | CTC | CTG | TGT | TTC | TTG ATG | 45 |
| | 1 | Met | Ser | Val | Pro | Ala | Ser | Ser | Phe | Leu | Leu | Leu | Cys | Phe | Leu Met | 15 |
| (SEQ ID NO:115) | 1 | ATG | TCA | GTG | CCA | GCT | TCC | TCT | TTT | CTC | CTC | CTG | TTT | CTT | GAT GAA | 45 |
| | 1 | Met | Ser | Val | Pro | Ala | Ser | Ser | Phe | Leu | Leu | Leu | Phe | Leu | Asp Glu | 15 |
| (SEQ ID NO:116) | 1 | ATG | TCA | GTG | CCA | GCT | TCC | TCT | TTT | CTC | CTC | CTG | GTG | TTT | CTT GAT | 45 |
| | 1 | Met | Ser | Val | Pro | Ala | Ser | Ser | Phe | Leu | Leu | Leu | Val | Phe | Leu Asp | 15 |

FIG. 38

| | | |
|---|---|---|
| (SEQ ID NO:117) | 1<br>1 | CTT ACC AAC ATC TCC ATC ACC GTG GAG AGC GAC GAG TGT GGC AGC   45<br>Leu Thr Asn Ile Ser Ile Thr Val Glu Ser Asp Glu Cys Gly Ser   15 |
| (SEQ ID NO:118) | 1<br>1 | CTT ACC AAC ATC TCC ATC ACC GTG GAG CGA CGA GTG TGG CAG CTG   45<br>Leu Thr Asn Ile Ser Ile Thr Val Glu Arg Arg Val Trp Gln Leu   15 |
| (SEQ ID NO:119) | 1<br>1 | CTT ACC AAC ATC TCC ATC ACC GTG AGC GAC GAG TGT GGC AGC TGC   45<br>Leu Thr Asn Ile Ser Ile Thr Val Ser Asp Glu Cys Gly Ser Cys   15 |
| (SEQ ID NO:120) | 1<br>1 | CTT ACC AAC ATC TCC ATC ACC GGA GCC ACG AGT GTG GCA GCT GCA   45<br>Leu Thr Asn Ile Ser Ile Thr Gly Ala Thr Ser Val Ala Ala Ala   15 |
| (SEQ ID NO:121) | 1<br>1 | CTT ACC AAC ATC TCC ATC ACC GTG GAG ACG AGT GTG GCA GCT GCA   45<br>Leu Thr Asn Ile Ser Ile Thr Val Glu Thr Ser Val Ala Ala Ala   15 |
| (SEQ ID NO:122) | 1<br>1 | CTT ACC AAC ATC TCC ATC ACC GTG GAG AGC GCC GAG TGT GCC AGC   45<br>Leu Thr Asn Ile Ser Ile Thr Val Glu Ser Ala Glu Cys Gly Ser   15 |
| (SEQ ID NO:123) | 1<br>1 | CTT ACC AAC ATC TCC ATC ACC GTG GAG AGC GGC GAG TGT GGC AGC   45<br>Leu Thr Asn Ile Ser Ile Thr Val Glu Ser Gly Glu Cys Gly Ser   15 |
| (SEQ ID NO:124) | 1<br>1 | CTT ACC AAC ATC TCC ATC ACC GTG GAC TCG GAC GAG TGT GGC AGC   45<br>Leu Thr Asn Ile Ser Ile Thr Val Asp Ser Asp Glu Cys Gly Ser   15 |
| (SEQ ID NO:125) | 1<br>1 | CTT ACC AAC ATC TCC ATC ACC GTG GAG AGC GAC GAG TGC GGT GTG   45<br>Leu Thr Asn Ile Ser Ile Thr Val Glu Ser Asp Glu Cys Gly Val   15 |

FIG. 39

GENE EDITING OF REPRODUCTIVE HORMONES TO STERILIZE AQUATIC ANIMALS

CROSS-REFERENCE TO RELATED APPLICATIONS

The present application claims the benefit of priority under 35 U.S.C. § 119(e) to U.S. Provisional Applications No. 62/345,163, filed on Jun. 3, 2016, the content of which is incorporated herein by reference in its entirety.

STATEMENT REGARDING FEDERALLY SPONSORED RESEARCH OR DEVELOPMENT

This invention was made with U.S. government support under grant no. 2014-33522-22263, awarded by the U.S. Department of Agriculture. The U.S. government has certain rights in the invention.

SEQUENCE LISTING

This application contains a sequence listing filed in electronic form as an ASCII.txt file entitled 2015_054sequence-listing.txt, created on Jun. 5, 2017, and having a size of 28 kilobytes. The content of the sequence listing is incorporated herein in its entirety.

BACKGROUND

Provided herein are descriptions of gene edited fish with reduced fertility and compositions and methods for producing the same. In particular, these descriptions relate to fish with modifications (knockout) to genes expressing reproductive hormones and the genetic vectors and methods for reducing fertility in farmed fish (e.g. fish for consumption such as catfish, carp, tilapia, as well as ornamental fish that are not consumed). Exogenous supplementation of hormones to these gene-deleted fish then becomes the only way they can reproduce, preventing any cross-breeding of genetically engineered and gene edited fish or gene edited fish that escape into the wild with non-engineered, wild type fish already present in the environment. This method may has broad potential application as it can also be used to control reproduction in domestic fish in general exotic species and interspecific hybrids to prevent genetic impact on natural populations.

Aquaculture as an industry is growing rapidly throughout the world. In most places where it is already developed or developing, it is expanding at a rapid pace. This expansion is driven by the growing wealth in developing countries where the rising middle class is seeking affordable sources of protein, such as aquatic food products, as well as the inability of wild-capture fisheries to satisfy that demand.

Catfish farming, primarily channel catfish (*Ictalurus punctatus*) and its hybrid, channel catfish ♀ X blue catfish (*Ictalurus furcatus*) ♂ (Chatakonidi, personal communication), is the largest US aquaculture industry in terms of both weight and value, which accounting for more than 70% of all US aquaculture production and more than 40% of all sales. However, the catfish industry is in crisis. Catfish production has contracted since a high mark in 2003 and catfish production acres keep decreasing in the past years. The industry is currently struggling to keep pace with the increasing cost of inputs, particularly feed cost driven by the demand and high price of soybeans and corn, production inefficiencies, and competition with inexpensive imported frozen fish which now accounts for more than two-thirds of all US sales of frozen catfish fillets. Food safety will become a large issue if much of the aquatic food needs to be imported from other countries. In the last 2-3 years these issues have stabilized, but the industry has opportunity to grow and recapture its lost market share with improved production and production efficiency.

Exploiting fish genetics can greatly contribute to production efficiency and enhancing aquaculture production. Genetic enhancement of farmed fish has advanced to the point that it is now impacting aquaculture worldwide. Gene transfer holds great promise for genetic improvement of farmed fish and catfish.

Transgenic technology is a powerful technology which has high potential to increase both production and profit of catfish industry. Transgenic fish have been developed that have improved growth, color, disease resistance, tolerance of heavy metals, survival in cold and body composition, and that can produce pharmaceutical proteins. The application of transgenic techniques to fish that has received the most attention is growth enhancement. Transgenic fish such as Atlantic salmon (*Salmo salar*), coho salmon (*Oncorhynchus kisutch*) and mud loach (*Misgurnus mizolepis*) have been produced, for which growth enhancement is dramatic, with fish growing to be more than ten-fold faster, and as high as 35-fold faster in mud loach, than control growth that can probably never be achieved by traditional breeding. Transfer of growth hormone (GH) genes also enhances performance in channel catfish. Five generations of mass selection has increased growth in channel catfish by 65%. By inserting GH gene, an additional 41% increase in growth is obtained. GH gene transfer in catfish has numerous other positive effects including increasing percent protein lowering fat percentage and improving flavor and texture.

Disease is the most critical problem of catfish industry, which leads to the largest economic loss. The most effective mechanism for increasing disease resistance in catfish is transgenesis via transfer of cecropin genes found originally in the moth (*Hyalophora cecropia*), which gave two to four-fold increase in bacterial disease resistance and was much better than what was obtained through selection. There is an evidence that cecropin might also have anti-viral and anti-fungal properties.

Concern and controversy exists regarding the possible ecological impacts of transgenic fish should they escape into the current habitats. Physical containment and physico-chemical containment are options to confine various types of fish. However, these options work in very limited cases, have inherent disadvantages, and usually are not practical. Chemical and mechanical sterilization are additional approaches, but the disadvantages are that the effects are temporary and are not feasible on a commercial scale in fish. Monosexing may be an approach for some fish. The sex ratio of Nile tilapia and loach were altered when fry are cultured in different temperature during their sex differentiation period, and hormonal sex control can lead to populations having the genotype of a single sex. This approach will only provide confinement if the fish are utilized in locations where members of the same species are not present.

Virtually all ecological issues become moot if transgenic fish are genetically sterile. Several genetic mechanisms can result in sterility, but unfortunately all of the systems developed have significant shortcomings, making them unacceptable to address these ecological problems, especially on a commercial scale. Induction of triploidy is a popular sterilization option, but it still requires fertile diploid brood stock, so risk is not eliminated. Additionally, in some cases triploidy can decrease performance in fish and is not feasible in catfish and many other species of fish industry on a commercial scale.

Transgenic sterilization is another option and includes technologies under development such as complementary DNA overexpression and short hairpin RNA interference, repressible Tet-off and modified Tet-off based systems driving expression of a blocker gene, antisense RNA, dsRNA, sense RNA or ribozyme to an early key developmental gene, site-specific recombinases, such as Cre and FLP, that excise key developmental genes, and hammerhead ribozymes that knockdown expression of target genes. Each of these systems struggle with difficulties, including (1) incomplete knockdown of fertility, (2) the need to maintain fertile broodstock which fails to remove the threat of environmental harm should broodstock escape, (3) failure to apply to other species (4) lack of commercial feasibility, or (5) complexity and expense.

Fish have a multitude of reproductive as well as sexual differentiation strategies. Because of this diversity, the mechanisms, even though apparently obvious in one species, may not function exactly the same in a second species. This is illustrated by the fact that in zebrafish FSH knockouts and LH knockouts are fertile and FSH knockouts are sex reversed to males, whereas our channel catfish FSH and LH knockouts are sterile and we do not see sex reversal in the channel catfish FSH knockouts (as described in Zhang et al. Mol Endocrinol, January 2015, 29(1):76-98 and Chu et al. Mol Endocrinol, November 2014, 28(11):1785-1795).

Therefore, there remains a need for controlling the reproductive capacities of genetically engineered aquatic animals such as fish and, in general, various domestic genotypes. Here, the inventors disclose methods and compositions for efficiently removing genetic material necessary for reproduction in catfish.

SUMMARY

Disclosed herein are methods and compositions for gene editing reproductive hormones in fish. These methods and compositions may be used to introduce gene editing changes at the single cell and multicellular level, followed by growth to an adult fish. Compositions include genetic vectors encoding nucleases that target sites in the luteinizing hormone (LH), gonadotropin-releasing hormone (GnRH), or follicle-stimulating hormone (FSH) of the fish. These genetic vectors could comprise DNA or RNA that encode the nuclease protein products. Target sites of the nucleases may be designed to induce double strand breaks in the coding, or exon, regions of the reproductive hormone genes or may cause individual base pair substitutions leading to specific nucleotide changes in the coding, or exon, regions of these genes.

Also included are methods for delivery of genetic vectors for high efficiency of inducing gene editing in the fish. Said methods include delivery of at least one genetic vector into gametes prior to fertilization. Other methods include delivery of at least one genetic vector into embryos after fertilization. Other methods include delivery of at least one genetic vector into embryos both prior to and after fertilization.

One embodiment includes polynucleic acid vectors that can encode at least one nuclease targeting at least one of the reproductive hormones. Preferred embodiments include vectors that encode genes any one of the gene editing technologies currently known in the art, such as zinc finger nucleases (ZFN), Transcription activator-like effector nucleases (TALEN), or Clustered Regularly Interspaced Short Palindromic Repeats-associated nucleases (CRISPR-Cas9). These nucleases are well known in the art and descriptions of these nucleases and how to design them can be found in the published literature. These nucleases may target any one of the reproductive genes in fish. Preferred targets include, but are not limited to the LH, GnRH, and FSH genes. Preferred targets within these genes include, but are not limited to, target sequences such as SEQ ID NOs: 1, 2, 3, 4, 5, 6, 7, 8, or gene sequences that show 50%, 60%, 70%, 80%, 90%, or up to 100% sequence homology. In addition, any of the future CRISPR technologies using nucleases other than Cas9 could be readily used with these methods and compositions.

Another embodiment includes methods delivering genetic vectors into gametes using viral vectors, electroporation, transfection, microinjection, or other common methods of introducing nucleic acid vectors into cells. A preferred embodiment includes electroporation of gametes, and in particular sperm cells, as described in Qin., et al Mar Biotechnol (2016) 18:255-263. Another embodiment includes delivering genetic vectors into embryos using any of the aforementioned delivery methods. Yet a further preferred embodiment includes a dual-delivery of said vectors into gametes first, using those gametes for fertilization, and then again delivering the same vectors into embryos that resulted from fertilization. This methods is described in detail in Qin., et al Mar Biotechnol (2016) 18:255-263.

Another embodiment includes fish that have been gene edited in their reproductive genes. Genes that may be gene-edited include, but are not limited to, the LH, GnRH, and FSH genes. Species of fish may include food production or consumable fish, such as catfish, carp, or tilapia, as well as non-consumable fish, such as ornamentals. A preferred embodiment may include a catfish that has been gene edited in the LH gene, such that the fish shows reduced fertility. Yet another preferred embodiment may include a catfish that has been gene edited in the GnRH gene, such that the fish shows reduced fertility. Yet another preferred embodiment may include a catfish that has been gene edited in the FSH gene, such that the fish shows reduced fertility. Yet another embodiment may include a catfish that has been gene edited in more than one reproductive gene, such that the fish shows reduced fertility. Any one of these embodiments may include genes may have been edited using any one of the gene editing technologies mentioned (ZFN, TALEN, CRISPR/Cas9). In addition, any of the future CRJSPR technologies using nucleases other than Cas9 could be readily used to introduce these genetic changes.

Examples of how these methods and compositions may be employed may be found in the detailed examples provided in this application. One such embodiment that describes specific examples and methodology can be found in the previously referenced Qin., et al Mar Biotechnol (2016) 18:255-263.

BRIEF DESCRIPTION OF THE DRAWINGS

FIG. 7. Sequences of luteinizing hormone (LH) gene with zinc finger nuclease (ZFN) induced mutations. Underlined letters/dashes indicate modified nucleotides.

FIG. 14. Identification of edited catfish type gonadotropin-releasing hormone (cfGnRH) gene in channel catfish (*Ictalurus punctatus*) using Cel-I mutation detection assay.

FIG. 15. Sequences of channel catfish (*Ictalurus punctatus*) luteinizing hormone (LH) gene with transcription activator-like effector nuclease (TALEN) induced mutations. Underlined letters/dashes indicate modified nucleotides.

FIG. 16. Sequences of channel catfish (*Ictalurus punctatus*) follicle-stimulating hormone (FSH) gene with transcription activator-like effector nuclease (TALEN) induced mutations. Underlined letters/dashes indicate modified nucleotides.

FIG. 17. Sequences of channel catfish (*Ictalurus punctatus*) catfish type gonadotropin-releasing hormone (cfGnRH) gene with transcription activator-like effector nuclease (TALEN) induced mutations. Underlined letters/dashes indicate modified nucleotides.

FIG. 29. Identification of edited catfish type gonadotropin-releasing hormone (cfGnRH) gene in channel catfish (*Ictalurus punctatus*) microinjected with clustered regularly interspaced short palindromic repeats (CRISPR)/Cas9 RNAs using Cel-I mutation detection assay.

FIG. 30. Sequences of channel catfish (*Ictalurus punctatus*) luteinizing hormone (LH) gene with clustered regularly interspaced short palindromic repeats (CRISPR)/Cas9 plasmids electroporation induced mutations. Dashes indicate modified nucleotides.

FIG. 31. Sequences of channel catfish (*Ictalurus punctatus*) catfish type gonadotropin-releasing hormone (cfGnRH) gene with clustered regularly interspaced short palindromic repeats (CRISPR)/Cas9 plasmids electroporation induced mutations. Dashes indicate modified nucleotides.

FIG. 32. Sequences of channel catfish (*Ictalurus punctatus*) catfish type gonadotropin-releasing hormone (cfGnRH) gene with clustered regularly interspaced short palindromic repeats (CRISPR/Cas9 RNAs microinjection induced mutations. Underlined letters/dashes indicate modified nucleotides.

FIG. 37. Amino acid alignments of LH TALEN sites showing mutations and predicted shifts, changes, and stops in the modified sequences.

FIG. 38. Amino acid alignments of LH zinc finger sites showing mutations and predicted shifts, changes, and stops in the modified sequences.

FIG. 39. Amino acid alignments of FSH TALEN sites showing mutations and predicted shifts, changes, and stops in the modified sequences.

DETAILED DESCRIPTION

Figures 1, 2:
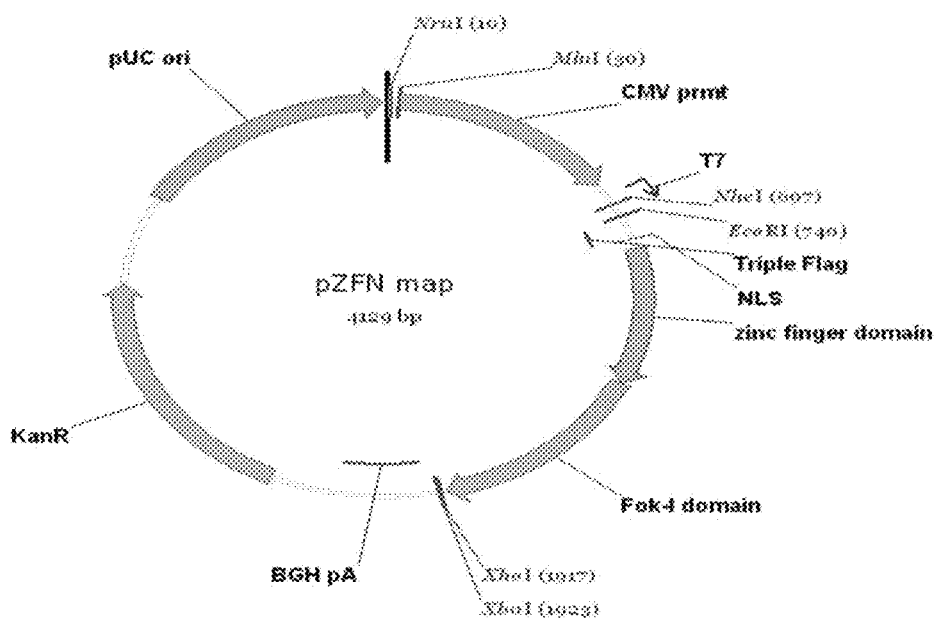
FIG. 1. Schematic representation of zinc finger nuclease (ZFN) plasmid structure targeting channel catfish (*Ictalurus punctatus*) luteinizing hormone (LH) gene.
FIG. 2. Three sets of zinc finger nucleases (ZFN targeting channel catfish (*Ictalurus punctatus*) luteinizing hormone (LH) gene.

Transgenic sterilization is a promising option to confine various biotechnological forms of fish including transgenics. Targets for transgenic sterilization would primarily include those responsible for gamete maturation and release. Gonadal maturation in teleost fish is primarily regulated by the hypothalamic-pituitary-gonadal axis. Gonadotropin-releasing hormone (GnRH) is known and named for its role as the final common signaling molecule used by the brain to regulate reproduction in all vertebrates. The GnRH decapeptide is synthesized by neurosecretory cells in the hypothalamus and secreted into portal vessels, to be transported to the pituitary gland and simulated the synthesis and release of hypophysial gonadotropin (including LH and FSH) which then simulates the secretion of steroid hormone from the gonads. These steroid hormones, in turn, feed back to the brain and the pituitary to complete the axis and to regulate the reproductive cycle.

To date, comparative endocrinological studies have revealed 14 different types of GnRH in vertebrates. In teleost fish, two or three forms of GnRH exist in the brain. The Siluriformes order to which channel catfish belongs has two fmms of GnRH, the first one is cGnRH-II and the second one named catfish type GnRH (cfGnRH), of which cfGnRH is the hypophysiotropic GnRH fmm and considered to be the gonadotropin releaser, which plays a key role in sexual maturation in catfish.

The glycoprotein hormone (GpH) family consists of follicle-stimulating hormone (FSH), luteinizing hormone (LH), chorionic gonadotropin (CG), thyroid-stimulating hormone (TSH), and thyrostimulin. These glycoproteins all share the same α subunit in a given species in a functional heterodimer consist of one α subunit and one β subunit, where the different β subunit confers distinct functions to each of them.

In teleost, there are two types of gonadotropin, FSH and LH. These two pituitary gonadotropins are now generally accepted as homologues and play central roles in regulating gametogenesis and the production of gonadal hormones required for the development of sexual behavior and secondary sex characters. In salmonid fish, FSH is primarily involved in spermatogenesis and vitellogenesis, where LH stimulates the maturation of oocytes, ovulation and spermiation. Both LH and FSH stimulate the maturation-inducing steroid testicular 11-ketotestosterone (11-KT) and 17α, 20β-dihydroxy-4-pregnen-3-one (17,20β-P) in males, whereas in females they stimulate production of ovarian estradiol-17β (E2) and 17,20β-P.

The introduction of a recombinant vector containing gonadotropin releasing hormone (GnRH) antisense sequence can result in transgenic fish expressing GnRH antisense mRNA, which disturbs the normal function of GnRH and leads to sterile fish (Uzbekova et al., 2000; Hu et al., 2007). The fertility of the fish could be restored by therapy with exogenous artificial GnRH. The disadvantage is that GnRH is needed at different time points of fish development. They may need to be captured multiple times to administer the therapy which would not be practical at a commercial scale.

In the past decade, new approaches enabling researchers to accurately manipulate genes via gene editing have been developed. This technology could be used to knock out reproductive function. The core technology is based on the use of engineered nucleases composed of specific DNA recognition and binding domains and non-specific DNA cleavage modules (Gaj et al., 2013). These methods can produce DNA double-strand breaks (DSB) at the targeted sequences and stimulate DNA repair mechanisms by either nonhomologous end joining (NHEJ) or homology-directed repair (HDR) (Wyman and Kanaar, 2006), which induce efficient alteration of genes by nucleotide deletion and/or insertion and modify normal gene functions. Zinc finger nuclease (ZFN), transcription activator-like effector nuclease (TALEN) and clustered regularly interspaced short palindromic repeats (CRISPR)/CRISPR-associated (Cas) are developed as the popular targeted gene editing technologies.

Zinc finger nucleases (ZFNs) are a class of engineered proteins that create a highly targeted DSB within the genome and enable the manipulation of the genome with unprecedented ease and precision (Urnov et al., 2005). ZFNs consist of two domains, a zinc finger DNA binding domain comprised of a chain of zinc finger proteins and a DNA-cleaving domain comprised of catalytic nuclease domain of FokI (Santiago et al., 2008). The zinc finger domains usually consist of 3-6 zinc finger proteins that each can specifically recognize and bind to 9-18 base pair target DNA. The nuclease domain comes from a restriction endonuclease FokI and more importantly is it has been reengineered to function as an obligate heterodimer to cleave DNA (Miller et al., 2007). The relatively easier modular design offers a greater number of combinatorial possibilities that could be designed to target a number of genes in the genome.

Transcription activator-like effector nucleases (TALENs) are proteins engineered by fusion of a FokI endonuclease domain with a transcription activator-like (TAL) effectors DNA binding domain. TAL effectors are specific DNA binding proteins produced by plant pathogenic bacteria Xanthamonas to modulate host gene expression (Aigner et al., 2010) and composed with highly conserved 33-35 amino acid repeats. The amino acids in positions 12 and 13, referred to as "repeat variable di-residue" (RVD), vary and specify DNA-binding properties (Boch et al., 2009; Moscou and Bogdanove, 2009). Thus TALENs can be designed by the combination of TAL effectors to recognize much of the genome. Whereas the nuclease domain is similar to that of ZFNs with the restriction endonuclease FokI and works obligately as heterodimer (Ansai et al., 2013).

Clustered regularly interspaced short palindromic repeats (CRISPR)/CRISPR-associated (Cas) system is a microbial adaptive immune system that uses RNA-guided nucleases to cleave foreign genetic elements so that protects bacteria and archaea from invading viruses and plasmids (Bhaya et al., 2011). Three major types of CRISPR (types I-III) have been categorized on the basis of locus organization and conservation (Makarova et al., 2011), in which the type II CRISPR system is one of the best characterized consisting the nuclease Cas9, the crRNA array that encodes the guide RNAs and a required auxiliary trans-activating crRNA (tracrRNA) that facilitates the processing of the crRNA array into discrete units (Gasiunas et al., 2012; Jinek et al., 2012). Each crRNA unit then contains a 20-nt guide sequence and a partial direct repeat, where the former direct Cas9 to a 20-bp DNA target. The crRNA and tracrRNA can be fused together to create a chimeric, single-guide RNA (sgRNA) (Ran et al., 2013). Cas9 can thus be re-directed toward almost any target of interest in the genome.

Disclosed herein are systems and methods for reversible genetic sterilization in channel catfish, to reproductively confine and prevent the impact of transgenic or domestic species on the natural environment and to protect the ecosystem. Specific examples include sterilizing channel catfish using ZFN, TALEN and CRSPR/Cas9 technologies by inactivating LH, FSH and cfGnRH genes either with electroporation or microinjection, evaluating their efficiencies and potential plasmids integration, as well as the hormone therapy of fertility restoration. This approach could serve as a model for other aquaculture species including any domestic genotype, interspecific hybrid, transgenic or exotic to minimize impacts on the natural environment, protect genetic biodiversity and ecosystems, increasing environmental friendliness of aquaculture and transgenic fish.

Unless otherwise specified or indicated by context, the terms "a", "an", and "the" mean "one or more." In addition, singular nouns such as "a bacterium," "a carrier," and "a vector" should be interpreted to mean "bacteria," "carriers," and "vectors," unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

As used herein, a "fish" means a farmed fish for grown for consumption (e.g. catfish, carp, or tilapia) as well as ornamental fish that are not consumed.

As used herein, "modification" to nucleotide sequences shall include base changes, deletions, insertions, rearrangements, inversions, duplications, or other changes commonly found in the art that are associated with nucleotide repairs.

EXAMPLES

The following examples are illustrative and are not intended to limit the claimed subject matter.

Example 1—Gene Edit of Luteinizing Hormone Gene Sterilize Channel Catfish, Ictalurus punctatus, Using a Modified Zinc Finger Nuclease Technology Abstract Channel catfish (Ictalurus punctatus) is the most important freshwater aquaculture species in the US. Genetically enhanced fish that are sterile could both profit the catfish industry and overcome potential environmental and ecological risk. As the first step to generate sterile channel catfish, three sets of zinc finger nuclease (ZFN) plasmids targeting the luteinizing hormone (LH) gene were designed and electroporated into one-cell embryos; different concentrations were introduced and the Cel-I assay was conducted to detect mutations, Channel catfish carrying the mutated LH gene were sterile, as confirmed by DNA sequencing and mating experiments. The overall mutation rate was 19.7% for 66 channel catfish, and the best treatment was ZFN set 1 at the concentration 25 g/ml. The introduction of the ZFN plasmids may have reduced mosaicism as mutated individuals were gene edited in every tissue evaluated. Apparently, the plasmids were eventually degraded without integration as they were not detectable in mutated individuals using PCR. Carp pituitary extract failed to induce spawning and restoration of fertility indicating the need for developing other hormone therapies to achieve reversal of sterility upon demand. This is the first sterilization achieved using ZFNs and plasmids electroporation in an aquaculture species, and the first successful gene editing of channel catfish. Our results will help in understanding the roles of LH gene, sterilization of teleost fish and is a step towards control of domestic, hybrid, exotic, invasive and transgenic fish.

1 Introduction

Technology for targeted gene editing is advancing rapidly. Zinc finger nuclease (ZFN) was a major breakthrough, which allowed targeted gene manipulation. ZFN technology is a novel gene editing tool developed in recent years, which are a class of engineered proteins that could create a highly targeted DNA double-strand break (DSB) within the genome and enable the manipulation of the genome with unprecedented ease and precision (Urnov et al., 2005).

ZFN consists of two domains, a zinc finger DNA binding domain comprised of a chain of zinc finger proteins that could recognize and combine to the target sequences, and a DNA-cleaving domain comprised of catalytic endonuclease FokI which creates DNA strand break. When a pair of ZFNs binds to their target in the correct orientation, FokI monomers can dimerize at the target site and introduce a DNA DSB. Then, cells will initiate the DNA repair processes by one of two highly conserved processes, homology-directed repair (HDR) or non-homologous end joining (NHEJ) (Urnov et al., 2010; Stoddard, 2011). The NHEJ is an error prone process that usually leads to mutations (nonsense, deletion, insertion or frame shift) at the target site and the gene product usually loses its function.

ZFN-mediated mutations have been reported in a number of animals, including fruit fly (Drosophila melanogaster) (Bibikova et al., 2002; Beumer et al., 2008), sea urchin (Hemicentrotus pulcherrimus) (Ochiat et al., 2010), frog (Xenopus tropicalis) (Young et al., 2011; Nakajima et al., 2012), zebrafish (Danio rerio) (Doyon et al., 2008; Meng et al., 2008; Foley et al., 2009), rat (Rattus norvegicus) (Geurts et al., 2009; Mashimo et al., 2010; Cui et al., 2011) and rabbit (Flisikowska et al., 2011). In all these studies, ZFNs could be successfully applied to introduce the target gene mutations, lead to the loss of gene function and the corresponding phenotype modification. In addition, these gene mutations could also be inherited by their offspring and a mutated family could be built.

Channel catfish (Ictalurus punctatus) and its hybrid, channel catfish ♀ X blue catfish (Ictalurus furcatus) ♂ (Chatakonidi, personal communication), are the leading freshwater aquaculture organism in the US and catfish farming is the largest aquaculture industry in both weight and value, accounting for more than 70% of all US aquaculture production and more than 40% of all sales (Zhang et al., 2014b; NASS, 2013). However, the catfish industry is in crisis, struggling with the rising cost of inputs, production inefficiencies and competing with inexpensive imported frozen fish. Exploiting fish genetics can greatly contribute to production efficiency and enhancement. Genetic enhancement of farmed fish has advanced to the point that it is now impacting aquaculture worldwide (Dunham et al., 2000; Dunham, 2011). Gene editing is a powerful technology which has high potential to increase production of aquaculture and profit to catfish industry. A critical problem in aquaculture is the potential escapement of domestic, hybrid, exotic and transgenic fish with potential adverse effects on the natural environment. Virtually all ecological issues become moot if genetically sterile brood stocks are used.

Luteinizing hormone (LH) is one of the gonadotropins that belongs to the glycoprotein hormone family (Hsu et al., 2002). Glycoproteins are functional heterodimers, consisting of one a subunit and one β subunit. Within a given fish species all a subunits are identical while the different β subunit confers the physiological specificity of the hormone (Liu et al., 2001). LH plays central roles in regulating gametogenesis and the production of gonadal hormones. LH stimulates secretion of the maturation-inducing steroid testicular 11-ketotestosterone (11-KT) and 17α,20β-dihydroxy-4-pregnen-3-one (17,20β-P) in males (Planas and Swanson, 1995; Kagawa et al., 1998), while working in females by producing ovarian estradiol-17β (E2) and 17,20β-P (Suzuki et al., 1988; Kagawa et al., 2003). LH is expressed in later stages of reproductive cycle and regulates spermiation and ovulation (Rosenfeld et al., 2007; Levavi-Sivan et al., 2010).

In the present study, we delivered the ZFN plasmids, targeting the LH gene, into fertilized eggs with electroporation process and our study aims to create a gene edited sterile channel catfish by ZFN mediated targeting mutagenesis. Usually, ZFN mRNA is delivered by microinjection, thus, the electroporation of ZFNs plasmids offers a novel and potentially more effective delivery mechanism not previously evaluated in fish. The potential disadvantage is integration of the plasmids, which would result in a transgenic organism obviating one of the advantages of gene editing. Evaluation of potential integration was another objective of the current study.

2 Material and Methods 2.1 Construction of Zinc Finger Nuclease

The design and assembly of ZFNs plasmids, "CompoZr Custom ZFN" plasmids, were provided by Sigma-Aldrich Company (St. Louis, Mo.). All the plasmids are driven by the cytomegalovirus (CMV) promoter and the T7 promoter, followed with the zinc finger domain, FokI domain and the kanamycin resistant element (FIG. 1).

The channel catfish (*I. punctatus*) LH gene β subunit (AF112192) (Liu et al., 2001) was chosen as the target gene and three targeting sites were selected (FIG. 2) for gene editing and sterilization of channel catfish. Three sets of ZFN plasmids targeting each site were prepared and MEI-I assay was performed by the company to check the ZFNs activity as previously described (Urnov et al., 2005; Doyon et al., 2008).

Figure 3:
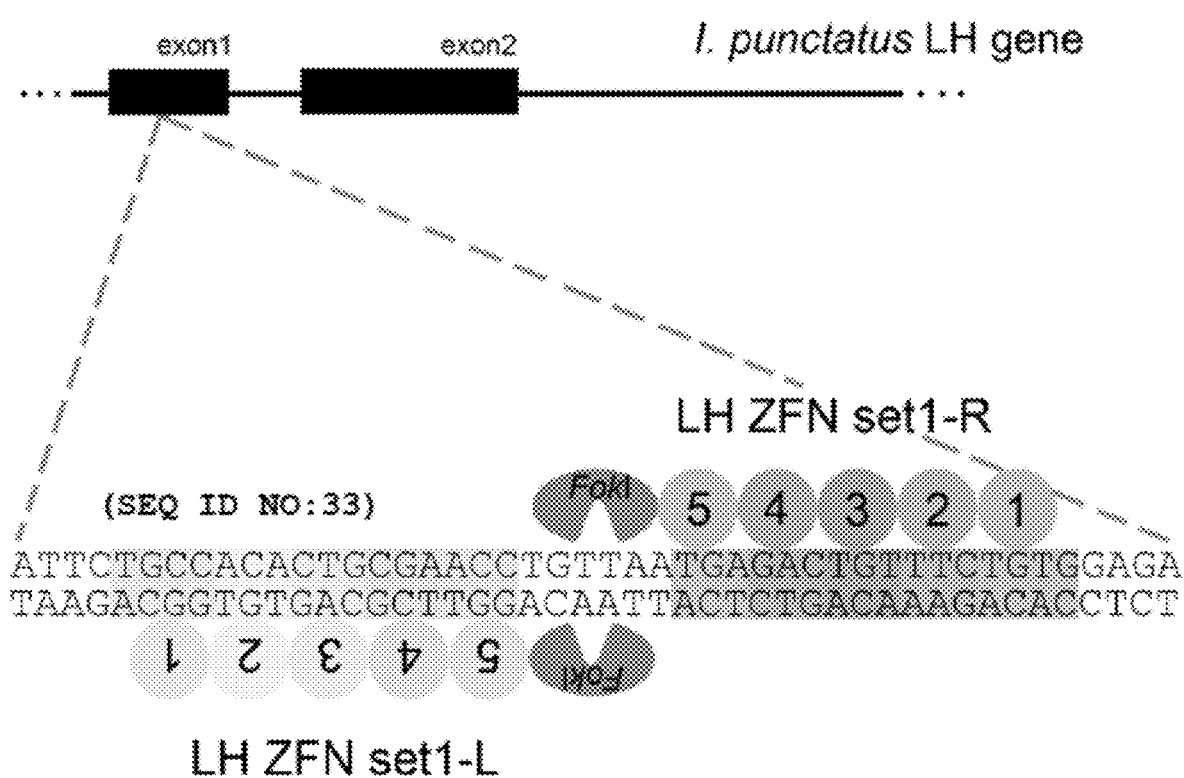
FIG. 3. The location of the zinc finger nuclease (ZFN) target site in the *Ictalurus punctatus* luteinizing hormone (LH) gene.

Three sets of ZFNs were designed to disrupt the *I. punctatus* LH gene, and the targeting sites were all located within the ORF of channel catfish LH gene β subunit (FIG. 3).

2.2 Plasmid DNA Preparation

ZFN plasmids were transformed into One Shot Top 10F' Chemically Competent *E. coli* (Invitrogen, Grand Island, N.Y.) following the manufacturer's instruction and cultured in LB broth. 100 μl transformation mix was used to spread on the LB agar plate with 50 μg/ml kanamycin. A single colony was picked up from each plate and cultured in 400 ml LB broth with 50 μg/ml kanamycin. Plasmids were then extracted with the IsoPure Plasmid Maxi II Prep Kit (Denville, Holliston, Mass.) and their quantity and quality were inspected by gel electrophoresis and spectrophotometry.

The ZFN plasmids of each set were prepared separately for the purpose of double electroporation (Su, 2012; Dunham and Winn, 2014). Equal amount of both left and right ZFNs were mixed together and diluted with 2 ml saline (0.9% NaCl) to the final concentration of 10 μg/ml, 25 μg/ml and 50 μg/ml for the first electroporation of sperm. The purpose of the saline was to dehydrate the sperm once they were introduced to the solution; when rehydrated, transformation rates of the embryos can be improved (Kang et al., 1999; Collares et al., 2010). Meanwhile, the same concentration of ZFNs was diluted with 5 ml TE buffer (5 mM Tris-HC, 0.5M EDTA, pH=8.0), which was then used for a second electroporation of embryos.

2.3 Brood Stock Spawning

Sexually mature channel catfish were harvested from the Fisheries Genetics Unit, E.W. Shell Research Center (Auburn University, Auburn, Ala.) and artificially spawned in aquaria with flowing water at 26 to 27° C. Kansas random female channel catfish were implanted with luteinizing hormone releasing hormone analog (LHRHa) at 90 μg/kg body weight to facilitate ovulation. Eggs were stripped from two ovulating females into metal pie pans coated with grease (Crisco, Orrville, Ohio). Two male channel catfish (Kansas random and AR) (Dunham and Smitherman, 1984) were euthanized and the testes were macerated into saline (0.9% NaCl) to release sperm and produce a sperm homogenate.

2.4 Fertilization, Electroporation and Incubation

Two drops of sperm solution were added to the ZFNs plasmids saline solution, mixed and incubated at room temperature for 5 min. Then the mixture was poured into a 10 ml petri dish and filled with fresh water. This solution was then electroporated with a Baekon 2000 macromolecule transfer system (Baekon, Inc., Saratoga, Calif.) with parameters set at 6 kV, 27 pulses, 0.8 s burst, 4 cycles, 160 μs (Powers et al., 1991).

Two hundred eggs were fertilized with these sperm and incubated in fresh water for 60 min. Then fertilized eggs were transferred into a 10 ml petri dish and ZFNs plasmids TE solution was poured into it. After 10 min of incubation, the embryos were electroporated again as described above. Control groups were treated similarly with double electroporation using saline and TE buffer without ZFNs plasmids.

Embryos were moved into separate 10 L tubs filled with Holtfreter's solution (Bart and Dunham, 1996) containing 10 ppm doxycycline and reared at 27° C. until hatch. Dead embryos were picked out and water was changed daily. Then channel catfish fry were transferred into a recirculating system.

2.5 Sample Collection and DNA Extraction

The pelvic fin and barbel of 6-month-old fingerlings were sampled for DNA analysis. Fingerling were also euthanized and samples from barbel, brain, muscle, intestine and pelvic fin were collected, to study the mosaicism of the mutations. All samples were stored at −20° C.

To extract DNA, samples were digested with 100 g/ml proteinase K followed by protein precipitation and DNA ethanol precipitation as described by Kurita et al. (2004). DNA quantity and quality were determined with gel electrophoresis and spectrophotometry.

2.6 Mutation Analysis.

Channel catfish LH gene β subunit specific primers (Table 1) were designed and Roche Expand High FidelityPlus PCR System (Roche, Indianapolis, Ind.) was used to amply these DNA samples. The PCR amplification procedure was as follows: initial denaturation for 2 min at 94° C.; followed by 35 cycles of 94° C. for 30 s, 60° C. for 30 s and 72° C. for min; and a final elongation for 10 min at 72° C. PCR products were examined by gel electrophoresis.

TABLE 1

Primer sequences used for the amplification of luteinizing hormone (LH) β subunit in channel catfish (Ictalurus punctatus).

| Primer | Sequence (5'-3') | Product Size (bp) | Description |
|---|---|---|---|
| LH-F | AGGATGTCAGTGCCAGCTTC (SEQ ID NO: 9) | 572 | LH gene amplification and mutation analysis |
| LH-R | CTTGGAGTAAATGGACTCGTTG (SEQ ID NO: 10) | | |

LH gene mutations were detected through the Cel-I mutation detection assay with SURVEYOR Mutation Detection Kit (Integrated DNA Technologies, Coralville, Iowa) as described by Miller et al. (2007). This approach takes advantage of the NHEJ error prone DNA repairing process. After the denaturing and re-annealing treatment of the PCR products, the wild type and modified amplicons could anneal to create the heteroduplex structure, which will be cleaved by the CEL-I mismatch endonuclease. Thus, three bands will be seen after electrophoresis, which indicates the existence of mutation. In contrast, only one band on the gel represents no mutation occurs. Briefly, PCR products were denature and re-annealed as follows: 94° C. 10 min; 94° C. to 85° C.-2° C./s; 85° C. to 25° C.-0.1° C./s; cooling to 4° C.; then 1 μl Enhancer S and 10 Nuclease S were added into 5 μl of the products above and incubated at 42° C. for 30 min; The digested PCR products were resolved on 2% UltraPure Agrose-1000 high resolution agarose gel (Invitrogen, Grand Island, N.Y.).

2.7 TA Clone and Sequencing

To identify the exact modification of LH gene, the DNA samples were amplified with Roche Expand High Fidelity-Plus PCR system as described above. After purification with IsoPure DNA Purification Kit (Denville, Holliston, Mass.), PCR products were inserted into the vector of TOPO TA Cloning Kit for Sequencing (Invitrogen, Grand Island, N.Y.) and transformed into the One Shot TOP10F' Chemically Competent E. coli (Invitrogen, Grand Island, N.Y.). The positive competent cells harboring the putative mutated DNA fragments of each individual were selected with LB agar plate containing 100 μg/ml ampicillin.

At least 10 colonies, carrying mutated LH DNA from each individual, were picked up and amplified with LB broth. The plasmids were extracted using Zyppy™ Plasmid Miniprep Kit (ZYMO Research, Irvine, Calif.) and sequenced by Lucigen Corporation (Middleton, Wis.).

When the sequencing results came back, the quality of the sequencing was detected by examining the .abl file using the software FinchTV (version 1.4.0). Sequences of each results were then aligned with the wild type channel catfish LH gene β subunit using the online multiple sequence alignment tool Clustal Omega (http//www.ebi.ac.uk/Tools/msa/clustalo/).

2.8 Plasmid Integration Inspection

To determine the presence of plasmids integrated into the channel catfish genome or persisting in the cytoplasm, three pairs of primers (Table 2), amplifying the vector backbone, ZFN domain and CMV promoter region, respectively, were designed to detect ZFN plasmids in LH mutated channel catfish. The PCR procedure was the same as above and products were inspected with electrophoresis.

TABLE 2

Primer sequences used for the detection of zinc finger nuclease (ZFN) plasmids integration in channel catfish (Ictalurus punctatus).

| Primer | Sequence (5'-3') | Product Size (bp) | Description |
|---|---|---|---|
| I1-F | GTGTACGGCTACAGGGGAAA (SEQ ID NO: 11) | 203 | ZFN plasmids integration detection |
| I1-R | TTGGGGTTGAGGTGCTTATC (SEQ ID NO: 12) | | |
| I2-F | CGTGACCGAGTTCAAGTTCC (SEQ ID NO: 13) | 204 | ZFN plasmids integration detection |
| I2-R | AAGTTGATCTCGCCGTTGTT (SEQ ID NO: 14) | | |
| I3-F | TACAAAGACCATGACGGTGA (SEQ ID NO: 15) | 148 | ZFN plasmids integration detection |
| I3-R | TGCAGATTCGACACTGGAAG (SEQ ID NO: 16) | | |

2.9 Reproductive Evaluation of LH Mutants

When LH mutated channel catfish were two years old, four males and four females were paired in individual aquarium to mate. Meanwhile, four pairs of control catfish were also paired in individual aquaria. When three years old, 11 pairs of putative LH mutated channel catfish were paired in aquaria. In each case they were given 14 days to spawn naturally and then were injected with a priming dose of 2 mg/kg of carp pituitary extract (CPE) followed by a resolving dose of 6 mg/kg CPE 12 hours later. Fifteen control pairs were utilized at the same time. When the three-year old fish did not respond to the CPE injections after 4 days, they were given two more injections of CPE at 2 mg/kg every 3 days.

2.10 Statistical Analysis

Mutation rates, hatch rate and survival rates from different ZFN sets and different concentration groups were analyzed utilizing Pearson Chi-square Test and Fisher's Exact Test (McDonald, 2014). All analysis were performed with statistical software R (version 3.1.3).

3. Results

3.1 ZFN Activity Examination

Figure 4:
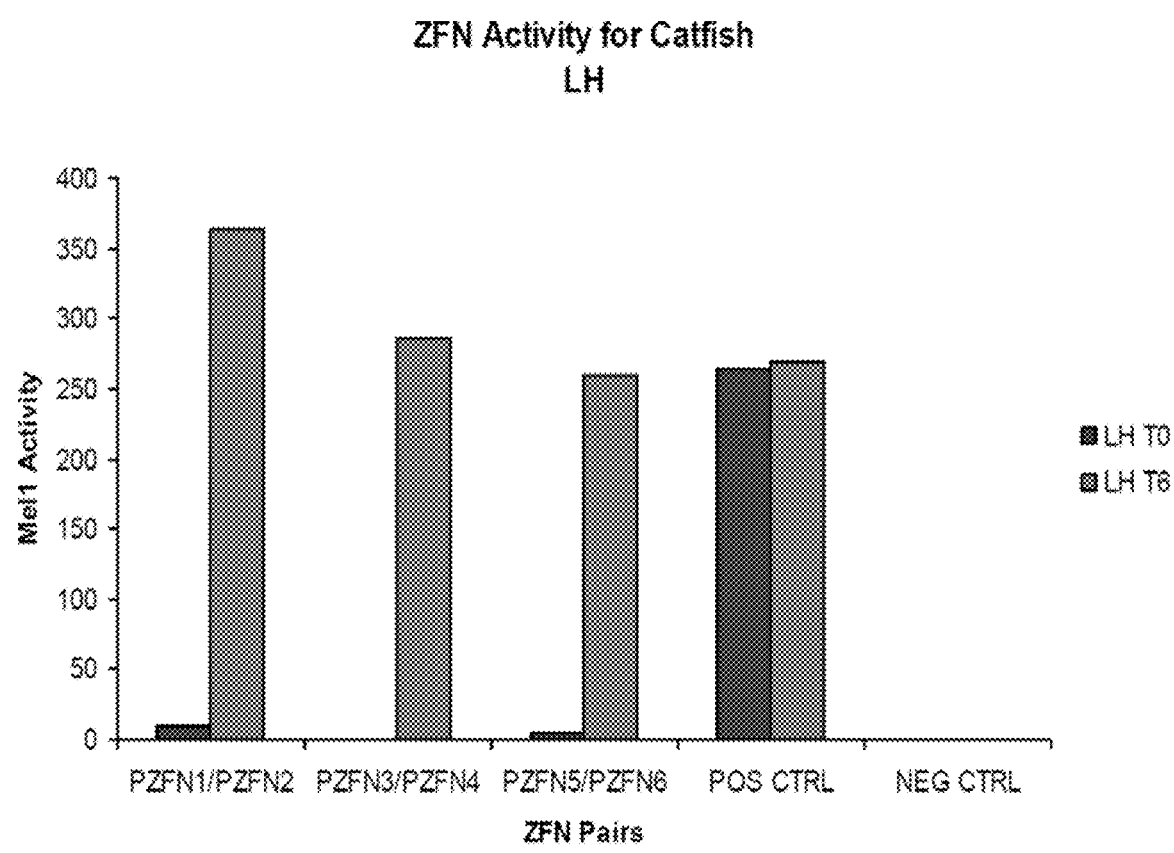
FIG. 4. Zinc finger nuclease (ZFN) activity as measured by the yeast MEL-1 reporter assay.

All these three sets of ZFNs displayed high activities in the yeast MEL-I assay (Doyon et al., 2008) (FIG. 4), among which ZFNs set1 had the highest activity.

3.2 Hatch Rate and Survival Rate

Two hundred eggs were double electroporated for each ZFN treatment group and control group. 47 of them hatched from ZFN set1 group (hatch rate 23.5%), 38 hatched in ZFN set2 group (19%) and 42 hatched from ZFN set3 group (hatch rate 21%). After 6-month growing, 32 out of 47 (68.1%) fry survived from ZFN set1 group, 12 of 38 (31.6%)

and 22 of 42 (52.4%) survived in ZFN set2 and set3 group, respectively (Table 3). Statistical analysis was performed and indicated the embryo hatch rate was not different from each group (p=0.544), but the fry survival rate was significantly different (p=0.004).

TABLE 3

Comparison of the embryo hatch rate and fry survival rate for different sets of zinc finger nuclease (ZFN) treatments in channel catfish (*Ictalurus punctatus*).

| Constructs | Eggs | Fry hatched | Hatch rate (%)* | Fry survival | Survival rat (%)† |
|---|---|---|---|---|---|
| ZFN-set1 | 200 | 47 | 23.5 | 32 | 68.1 |
| ZFN-set2 | 200 | 38 | 19.0 | 12 | 31.6 |
| ZFN-set3 | 200 | 42 | 21.0 | 22 | 52.4 |
| Control | 200 | 96 | 48.0 | 79 | 82.3 |

*No difference among treatment groups (p = 0.544); significant difference between treatment and control groups (p < 0.0001).
†Significant difference among treatment groups (p = 0.004) and between treatment and control groups (p = 0.033).

In contrast, the control group has a hatch rate of 48% (96 of 200) and survival rate of 82.3% (79 of 96), both of which were significant higher than treatment groups (p<0.001 and p=0.033).

3.3 Mutation Detection

Figure 5:
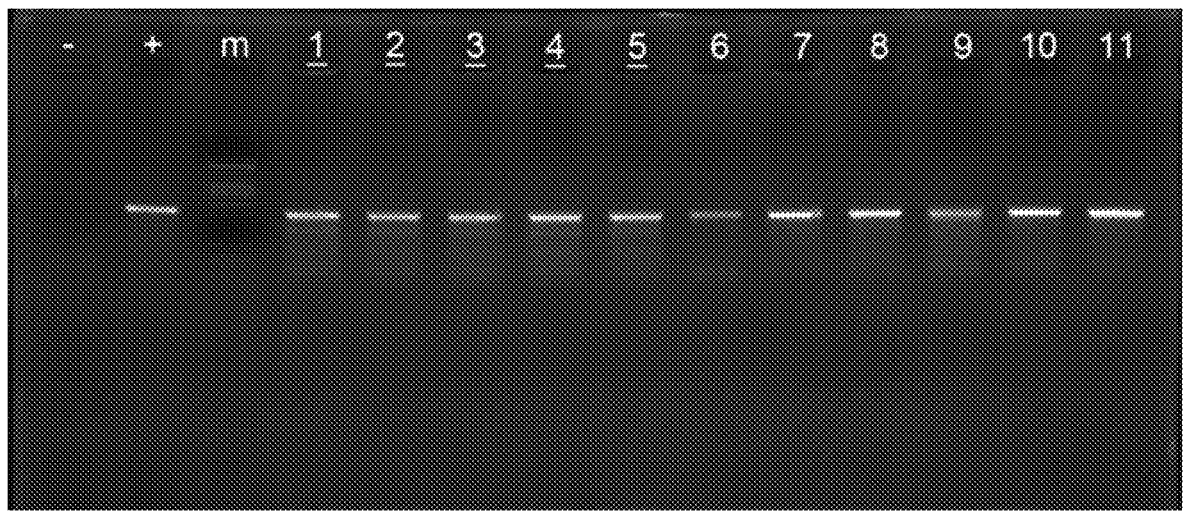
FIG. 5. Identification of edited luteinizing hormone (LH) gene in channel catfish (*Ictalurus punctatus*) using Cel-I mutation detection assay.

Pelvic fin and barbel samples were collected from each of the survived 66 fingerlings and DNA is extracted. After PCR amplification and Cel-I assay, the products were detected with high resolution gel electrophoresis. Three bands appearing on the gel indicated the individual containing mutated LH gene (FIG. 5).

The Cel-I assay indicated that the ZFN sets varied in effectiveness (Fisher's Exact Test, p=0.100). ZFN set1 treatment group had 31.3% (10 of 32) of individuals containing mutated LH gene (Table 4), for which 37.5% (3 of 8) occurred at the concentration 10 g/ml, 38.9% (7 of 18) at 25 µg/ml and 0 (0 of 6) at 50 g/ml. In contrast, zero (0 of 12) mutation was detected for ZFNs set 2 and 13.6% (3 of 22) for ZFNs set 3, including 25.0% (3 of 12) at concentration 25 µg/ml and zero at others. The overall mutation rate was 19.7% for a these 66 channel catfish, which rises to 25.0/o if the non-working concentration 50 g/ml is excluded.

TABLE 4

Comparison of luteinizing hormone (LH) gene mutation rate for different sets of zinc finger nucleases (ZFN) electroporated at different concentrations in channel catfish (*Ictalurus punctatus*).

| ZFN sets | Concentration (µg/ml) | N fry | N mutated fry | Mutation rate (%)* |
|---|---|---|---|---|
| ZFN set1 | 10 | 8 | 3 | 37.5 |
| | 25 | 18 | 7 | 38.9 |
| | 50 | 6 | 0 | 0 |
| ZFN set2 | 10 | 3 | 0 | 0 |
| | 25 | 5 | 0 | 0 |
| | 50 | 4 | 0 | 0 |
| ZFN set3 | 10 | 6 | 0 | 0 |
| | 25 | 12 | 3 | 25.0 |
| | 50 | 4 | 0 | 0 |
| Overall | | 66 | 13 | 19.7 |

*Mutation rate was significantly different among treatments (Fisher's Exact Test, p = 0.100) (50 µg/ml was excluded from analysis).

Figure 6:
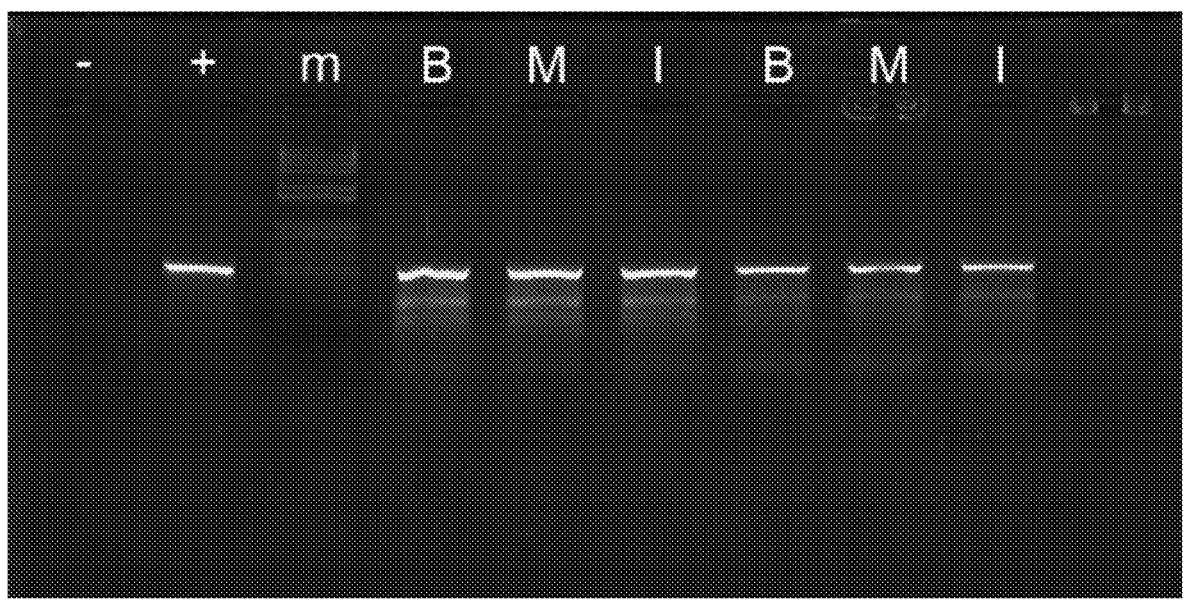
FIG. 6. Identification of edited luteinizing hormone (LH) gene in different tissues from two mutated channel catfish using Cel-I mutation detection assay.

Two mutated fingerlings, confirmed with the analysis of pelvic fin and barbel DNA, from the ZFNs set1 group were sacrificed and DNA was extracted from the brain, muscle and intestine to detect mosaicism of the LH gene mutation. Same procedure was conducted as above and the Cel-I assay results of all these tissues showed three bands on the gel (FIG. 6), indicative of all these tissues tested containing mutated LH gene.

3.4 Sequence Modification of Mutated LH Gene

Several types of mutations were observed from the multiple alignment result: 1 bp insertion (5 of 13 mutated individuals), 2 bp insertion (3 of 13), 1 bp substitution (1 of 13), 2 bp deletion (1 of 13) and complex type with both insertion and substitution (3 of 13) (FIG. 7). However, these mutations were not located at the expected ZFNs targeting position. The mutation sites were all located at around 60 bp upstream of the proposed target site, but were still within the ORF of LH p subunit gene.

3.5 ZFN Plasmids Integration Detection

Figure 8:
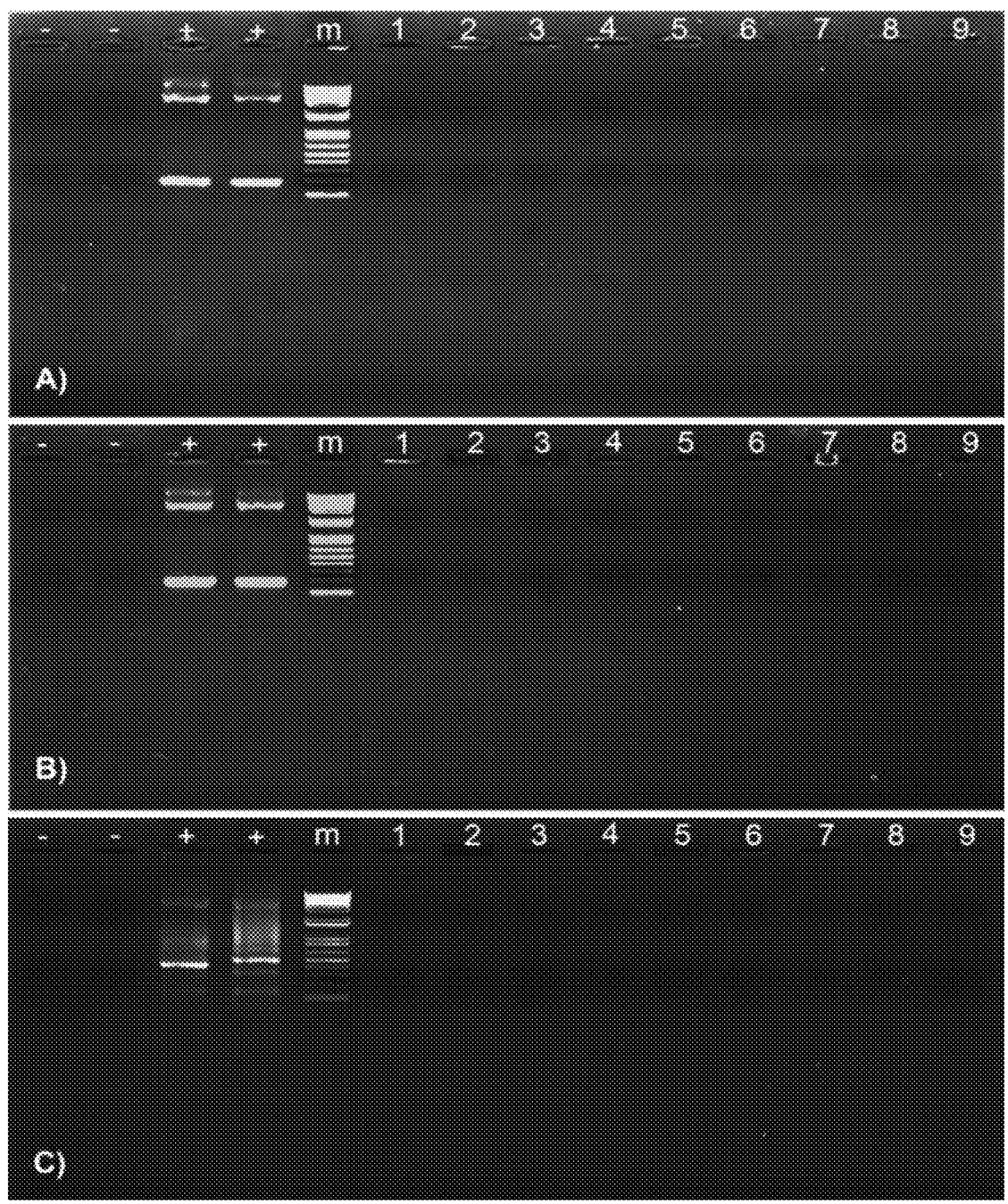
FIG. 8. PCR inspection of zinc finger nuclease (ZFN) plasmids integration.

Three pairs of ZFN plasmid specific primers (Table 2), amplifying vector backbone, ZFN domain and CMV promoter region, were used to detect potential plasmid integration or prevailing concatamers in the cytoplasm of these 3 groups of LH mutated channel catfish. Gel electrophoresis showed no band from all these individuals (FIG. 8), indicating the genome of them did not contain exogenous DNA fragments.

3.6 Fertility Restoration Evaluation

Four pairs of two-year-old catfish carrying the mutated LH gene were introduced to aquaria for natural spawning, but none of these catfish successfully spawned. In contrast, three of four pairs of catfish from the control group spawned naturally with eggs hatched.

At three years old, eleven pairs of putative LH mutated channel catfish did not spawn when given a two-week opportunity to mate. No courtship behavior was exhibited although they had outstanding secondary sexual characteristics. A series of CPE injections did not induce any spawning. Meanwhile, eleven out of fifteen control pairs produced fertile egg masses.

4 Discussion

Three different sets of ZFNs were designed to target the channel catfish LH gene and different concentrations of each set were tested. ZNF set 1 gave the best results with a 31.3% mutation rate, and ZFN set 2 did not generate mutants. ZFN set 1 was predicted to be the most effective based upon MEL-I assay, validating this assay for ZFN design and evaluation for catfish research. ZFN set 2 also had the lowest survival. One possibility is that this set generated more off-target mutations resulting in the mortality of any mutated individuals for ZN set 2. The hatch rate and fry survival of the control electroporated with buffer were both significantly higher than all of the ZFN treated embryos and fry suggesting that all 3 ZFN plasmid sets caused some level of lethal off-target effects during these early life stages. Obviously, these individuals were or would be quickly selected out of the population.

Different concentrations of ZFN plasmids used during the experiment also had distinct outcomes. For the two successful ZFNs sets, 25 µg/ml of plasmids showed the best results, combining for a 33.3% (10 of 30) mutation rate and accounting for 76.9% (10 of 13) of all mutated fry. When the plasmid concentration was increased to 50 µg/ml, no mutants were generated in all three sets of ZFNs. Taking the eggs hatch rate and fry survival rate into consideration, the best outcome was generated with ZFN set 1 with a plasmids concentration of 25 µg/ml.

ZFNs have been applied to target and manipulate genes in different animals such as zebrafish (*Danio rerio*) (Doyon et al., 2008; Meng et al., 2008; Foley et al., 2009), rainbow trout (*Oncorhynchus mykiss*) (Yano et al., 2012), frog (*Xenopus tropicalis*) (Young et al., 2011; Nakajima et al., 2012), mice (*Mus musculus*) (Carbery et al., 2010) and rat (*Rattus norvegicus*) (Geurts et al., 2009; Mashimo et al., 2010; Cui et al., 2011). Generally, ZFN technology results in the low mutation rates in fish (mostly zebraish and medaka), often approximately 1% (Gupta et al., 2011; Gupta et al., 2012; Moore et al., 2012; Chen et al., 2013), sometimes 4-30% (Doyon et al., 2008; Foley et al., 2009; Gupta et al., 2011; Ansai et al., 2012; Taibi et al., 2013; Yano et al., 2014; Zhang et al., 2014a) and on rare occasion 30-100% (Zhang et al., 2014a). The overall mutation rate (19.7%, and 25.0% if the failed 50 µg/ml treatment is discounted) and the highest mutation rate (38.9%) found in the current study are relatively high compared to most ZFN studies.

Microinjection was used to transfer the ZFNs mRNA into cells in previous studies. In our study, we transferred ZFNs plasmids instead of mRNA into the embryo with electroporation and successfully mutated the channel catfish LH gene. Introducing plasmids has advantages compared to introducing mRNA to induce mutations. Plasmids are easier to use and avoid degradation problems, require less time, effort and money and electroporation is technically easier than microinjection. Additionally, plasmids can persist in the embryo for an extended time during the development allowing greater opportunity for mutation.

Electroporation allows transfer of ZNFs to a large number of embryos in a short time. Two hundred channel catfish embryos can be electroporated at one time. Electroporation was successfully used for gene knock-in at the ROSA26 locus in mouse cell lines (Perez-Pinera et al., 2012) using ZFNs, but until our research, ZFN plasmids had not been introduced to a whole embryo. One criticism of electroporating plasmids is the possibility of their integration into the catfish genome, producing a transgenic as well as gene edited organism. However, ZFN plasmids were not detected in the LH mutated channel catfish, indicating that this technique can be used to generate gene edited individuals without the unwanted outcome of transgenesis.

Sequencing results showed a variety of LH knockouts were induced, including insertions, deletions, substitutions and a complex of multiple types. These mutations were not located at the ZFN targeted position, but were all located approximately 60 bp upstream of the target site. However, they were still located in the ORF of channel catfish LH gene.

Mosaicism is a common phenomenon in ZFNs mediated gene knockout animals (Carbery et al., 2010; Nakajima et al., 2012; Yano et al., 2012) as apparently ZFNs rarely induce mutations at the one-cell stage. In our study, barbel, brain, fin, muscle and intestine were among the tissues examined for LH mutation with upwards to 3 tissues tested per mutated fish. If a mutation was detected in one tissue, it was detected for every tissue tested.

To our knowledge, this is the first report that ZFNs produced a homogenous and uniform mutation in a teleost. The widespread incidence of mutation across multiple tissues is important as it would increases the probability of the mutation being found in the germline, and it may allow loss of function studies in the initial P1 generation rather than having to wait for inheritance of the mutation in F1 or F2 fish.

ZFN off-target effects have been observed in zebrafish (Meng et al., 2008; Gupta et al., 2011) and human cells (Porteus and Baltimore, 2003; Cathomen and Joung, 2008; Cornu et al., 2008; Pattanayak et al., 2011) with the DNA sequencing of the targeted genes. ZFN-induced cytotoxicity is an issue reported in several studies, and are most likely the result of excessive cleavage at off-target sites (Cathomen and Joung, 2008). The only circumstantial evidence for off-target effects in the current study were the lower survival of fry from ZFN set 2 for which no survivors were edited, and the significantly higher hatch and fry survival of the buffer electroporated control.

Four pairs of channel catfish carrying the mutated LH gene did not spawn at two years of age, in contrast to the three of four pairs of control catfish that successfully spawned under the same conditions. In the following year, 11 pairs of LH edited channel catfish did not show courtship behavior and did not spawn despite having excellent gravidness and other secondary sexual characteristics. Recent studies indicated LH gene is indispensable in zebrafish (*Danio rerio*) reproduction especially for females (Chu et al., 2014, Zhang et al., 2014b). Surprisingly, LH appears less important for fertility in zebrafish males. This phenomenon needs to be explored and confirmed in other species. However, our study strongly suggests that desired loss of function, sterilization, was successfully achieved in both females and males. Further morphological and physiological research are needed to compare LH knockout channel catfish testis development and spermatogenesis with that of zebrafish and to validate the difference. These 11 pairs of three-year-old fish did not spawn after hormone therapy with CPE. CPE is the universal ovulater and should have contained sufficient LH to allow final maturation of ova and sperm, but this hypothesis was apparently incorrect. Hormone therapy will need to be developed by evaluating different dose applications of purified LH to allow restoration of fertility and spawning of the LH mutated channel catfish.

5 Conclusion

An efficient approach for targeted gene mutagenesis with zinc finger nucleases in channel catfish *I. punctatus* is achieved. ZFNs targeting LH β subunit were used to induce LH gene mutations in the catfish genome, and LH inactivated channel catfish were generated. This is the first gene edited aquaculture species in the US using ZFNs.

Additionally, this study described an important approach that could be used to directly manipulate the genome of non-traditional animal models, which only requires the delivery of ZFN plasmids into the embryos with electroporation rather than the more technically difficult microinjection of mRNA into embryos. The mutated channel catfish did not respond to the CPE hormone therapy, and the technology to restore fertility will need to be improved.

Example 2—Gene Editing of Luteinizing Hormone, Follicle-stimulating Hormone and Gonadotropinreleasing Hormone Genes to Sterilize Channel Catfish, *Ictalurus punctatus*, Using Transcription Activator-Like Effector Nuclease Technology Abstract Transcription activator-like effector nuclease (TALEN) is a powerful new research tool that has broad applications in genetic manipulation. In the present study we demonstrate the targeted mutation of channel catfish (*Ictalurus punctatus*) luteinizing hormone (LH), follicle-stimulating hormone (FSH) and catfish type gonadotropin-releasing hormone (cfGnRH) genes with TALENs with the future goal of sterilization. TALEN plasmids were electroporated into embryos and successfully produced mutations confirmed with Cel-I assay and DNA sequencing. The mutation rates of LH, FSH and cfGnRH genes were 44.7%, 63.2% and 52.9% respectively, and mutations were detected at the expected TALEN cutting sites. Embryo hatch rates and fry survival rates were not different among either TALEN groups or among the TALEN and control groups, indicating low cell toxicity of TALENs. The electroporated plasmids were eventually degraded without integration based upon PCR. If the editing of these genes results in sterilization, it could be used in a variety of fish to minimize impacts on the natural environment, protect genetic biodiversity and ecosystems and increase environmental friendliness of aquaculture, interspecific hybrids, exotic species and transgenic fish.

I Introduction

Transcription activator-like effector nucleases (TALENs) is a site-specific gene editing technology that has generated much interest as a broadly applicable technology with high efficiency (Baker, 2012; DeFrancesco, 2012). TALEN is engineered by a fusion of a FokI endonuclease domain with a transcription activator-like (TAL) effector domain. The TAL effectors are a newly described class of specific DNA binding protein that produced by plant pathogenic bacteria Xanthamonas, and can directly modulate the host gene expression (Aigner et al., 2010).

Similar to zinc finger nucleases (ZFNs), the TAL effectors were engineered together to compose the DNA binding domain of TALEN. Each TAL effector consists of highly conserved 33-35 amino acid sequence repeats that could recognize and interact with a specific target nucleotide. The amino acids in position 12 and 13 of each amino acid repeat, referred to as "repeat variable di-residue" (RVD), vary and are what convey the specific DNA-binding properties. The four most common RVDs each preferentially associate with one of the four bases: NI binds to A, HD binds to C, NO binds to T and NN binds to G (Boch et al., 2009; Moscou and Bogdanove, 2009). Thus based on these straightforward sequence relationships, the TAL effector repeats can be joined together to form arrays binding to specific DNA sequence in the genome. The nuclease domain is the same as that of ZFNs with FokI endonuclease fused following the DNA binding domain and works obligately as a heterodimer (Ansai et al., 2013).

After both the left and right TALENs bind to the target site, FokI endonuclease will form a dimer and create a DNA double-strand break (DSB). This type of lesion is often repaired by non-homologous end-joining (NHEJ), which is an error-prone process and typically results in small insertions or deletions (Stoddard, 2011). The gene will be disabled because of the change or shift of the translational reading frame.

Compared to ZFNs, TALENs have some significant advantages. ZFN DNA binding module recognizes and binds three nucleotides at a time. Therefore the target sequences are limited by the combination of zinc finger proteins and much of the genome cannot be recognized by the ZFN binding domain. In contrast, the TAL effector of TALEN only associates with one nucleotide and can be assembled based on the target sequence information, and thus can be designed to target nearly any site in any genome (Miller et al., 2011). ZFN binding units typically bind only 9-18 base pairs on each side of the target site, while TALEN can be engineered to recognize longer DNA sequences, and may confer increased specificity, thus reduce the incidence of off-target editing. Another important advantage is that TALENs are simple and straightforward in design and assembly strategy (Cermak et al., 2011), such that manufacture of effective TALFNs is significantly cheaper and faster than that for ZFNs.

TALEN as a new and powerful genome editing technology has been successfully conducted in a number of animal models, including worm (*Bombyx mori*) (Ma et al., 2012), fruit fly (*Drosophila*) (Liu et al., 2012), ascidian (*Ciona intestinalis*) (Treen et al., 2014), zebrafish (*Danio rerio*) (Huang et al., 2011; Sander et al., 2011; Cade et al., 2012; Moore et al., 2012), medaka (*Oryzias latipes*) (Ansai et al., 2013), yellow catfish (*Tachysurus fulvidraco*) (Dong et al., 2014), frog (*Xenopus tropicalis*) (Lei et al., 2012), rat (*Rattus norvegicus*) (Tesson et al., 2011; Mashimo et al., 2013) and livestock (Carlson et al., 2012).

Catfish, especially channel catfish (*Ictalurus punctatus*) and its hybrid, channel catfish ♀ X blue catfish (*Ictalurus furcatus*) ♂, are the most important aquaculture organism in the US. However, catfish culture is plagued by production problems such as relatively slow growth rates, disease problems and control of reproduction, bringing the US aquaculture industry is into crisis (Hanson and Sites, 2012). Exploiting fish genetics can greatly contribute to production and efficiency, and gene editing is a powerful technology which has high potential to increase production of aquaculture and profit to catfish industry (Dunham et al., 2000; Dunham, 2011). Nevertheless, sterilization is needed to dispel public concern regarding the potential environment and ecological risk of transgenic, as well as hybrid, exotic and invasive fish.

Gonadotropin-releasing hormone (GnRH) is known for its role as the final common signaling molecule used by the brain to regulate reproduction in all vertebrates (Fernald and White, 1999), and stimulated the synthesis and release of hypophysial gonadotropin, including luteinizing hormone (LH) and follicle-stimulating hormone (FSH), which then stimulates the secretion of steroid hormone from the gonads (Amano et al., 2002). In teleost fish, two or three forms of GnRH exist (Amano et al., 2002), while in Siluriformes one form named catfish type GnRH (cfGnRH) and considered to play the key role in sexual maturation in catfish (Zandbergen et al., 1995; Zohar et al., 2010). The gonadotropins, LH and FSH, are heterodimers, sharing a common α-subunit and differing in their 0-subunits. They coordinate for the fine-tuning of ovarian and testicular function. FSH in certain fish has a dominant role in the initiation of gametogenesis and regulation of gonadal growth, whereas, LH is dominant mainly during gonadal maturation and spermiation/ovulation (Rosenfeld et al., 2007; Levavi-Sivan et al., 2010). Hypothetically, the mutations of LH, FSH and cfGnRH genes prevent transcription and lead to sterilization of fish.

In this experiment, we delivered TALEN plasmids targeting the channel catfish LH gene, FSH gene and cfGnRH gene, respectively, into fertilized eggs with electroporation and propose to create the gene edited sterile channel catfish by TALEN mediated targeting mutagenesis on genomic level. Our objectives include accomplishing knockout of channel catfish LH, FSH and cfGnRH genes by TALENs, compare the mutation efficiency and embryo hatch rate to ZFNs, and evaluate potential TALEN plasmids integration.

Figure 9:
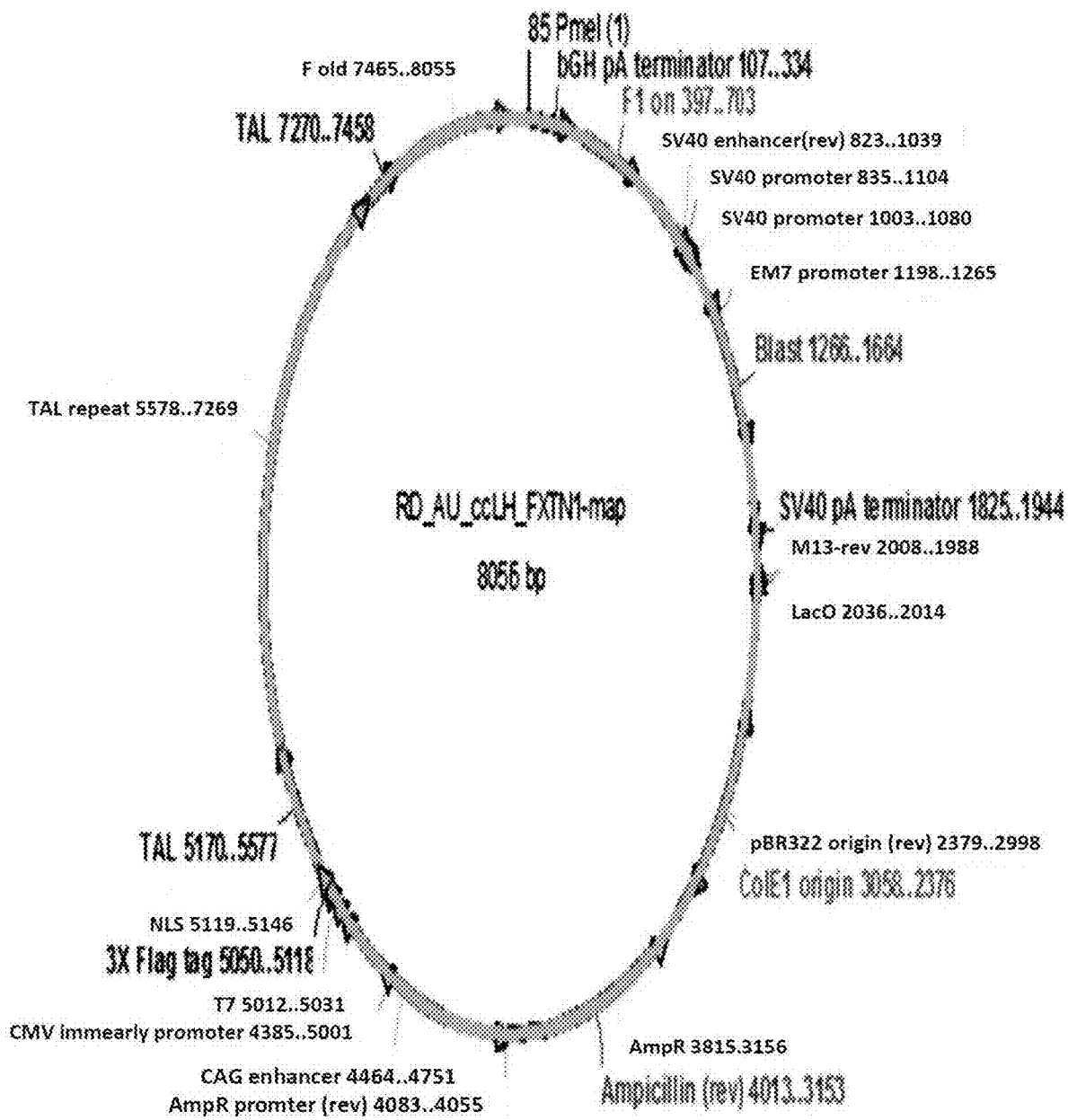
FIG. 9. Schematic representation of transcription activator-like effector nuclease (TALEN) plasmid structure targeting channel catfish (*Ictalurus punctatus*) luteinizing hormone (L1) gene.

2. Material and Methods 2.1 Construction of the Transcription Activator-Like-Effector Nuclease The design and assembly of TALENs plasmids, "XTN TALENs Site-Specific Nucleases" plasmids, were provided by Transposagen Company (Lexington, Ky.). All the plasmids were driven by the cytomegalovirus (CMV) promoter and the T7 promoter, followed by the site-specific TAL repeats, FokI domain and the ampicillin resistant element (FIG. 9).

The channel catfish (*I. punctatus*) LH gene s subunit (AF112192) (Liu et al., 2001), FSH gene β subunit (AF112191) (Liu et al., 2001) and the cfGnRH gene (data unpublished) were chosen as the target genes and one target site of each gene was selected (FIG. 10) for gene editing to sterilize catfish.

Figures 10, 11:
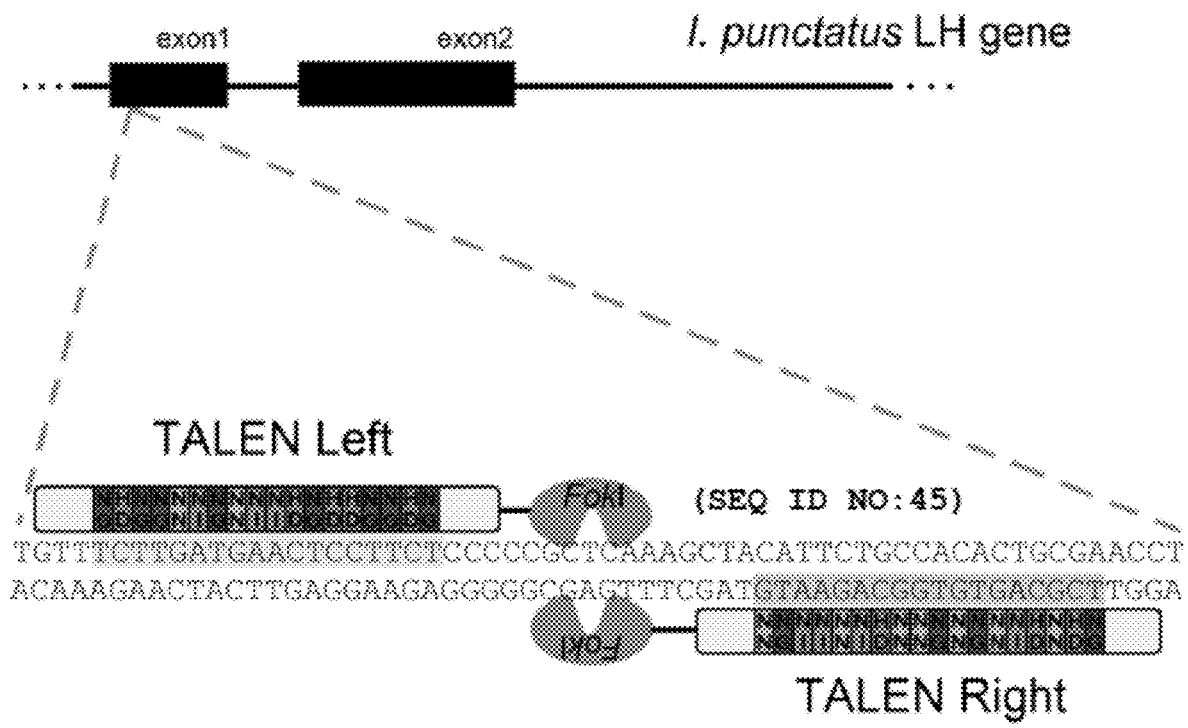
FIG. 10. Transcription activator-like effector nuclease (TALEN) plasmid sets targeting channel catfish (*Ictalurus punctatus*) luteinizing hormone (LH) gene, follicle-stimulating hormone (FSH) gene and catfish type gonadotropin-releasing hormone (cfGnRH) gene.
FIG. 11. The location of the transcription activator-like effector nuclease (TALEN) target site in the channel catfish (*Ictalurus punctatus*) luteinizing hormone (LH) gene.

A set of TALENs was designed to individually target the channel catfish LH gene, FSH gene and cfGnRH gene, respectively. The targeting sites of these TALENs were all located within the ORF, in order to disturb their function (FIG. 11).

2.2 Plasmid Preparation

The TALEN plasmids were transformed into One Shot Top 10F' Chemically Competent *E. coli* (invitrogen, Grand Island, N.Y.) following the manufacturer's instruction and cultured in LB broth. A 100 μl transformation mix of each plasmid was used to spread on the LB agar plate with 100 μg/ml ampicillin. A single colony was picked up from each plate and cultured in 400 ml LB broth with 100 g/ml ampicillin. Plasmids were then extracted with the IsoPure Plasmid Maxi II Prep Kit (Denville, Holliston, Mass.) and their quantity and quality were inspected by gel electrophoresis and spectrophotometry.

Each TALEN plasmid set was prepared for the purpose of double electroporation (Su, 2012; Dunham and Winn, 2014). Equal amounts of both left and right TALENs were mixed together and diluted with 2 ml saline (0.9% NaCl) to the final concentration of 25 g/ml each for the first elcetroporation of sperm. The same concentration of TALENs was diluted with 5 ml TE buffer (5 mM Tris-HCl, 0.5M EDTA, pH=8.0), for the second electroporation of embryos.

2.3 Brood Stock Spawning

Sexually mature Kansas random channel catfish females were implanted with luteinizing hormone releasing hormone analog (LHRHa) at 90 g/kg body weight to facilitate ovulation. Eggs were stripped from two ovulating females into metal pie pans coated with grease (Crisco, Orrville, Ohio). Two male channel catfish (Kansas random and AR) (Dunham and Smitherman, 1984) were euthanized and the testes were macerated into saline (0.9% NaCl) to release sperm and produce a sperm homogenate.

2.4 Fertilization, Electroporation and Incubation

Double electroporation was performed for each of the TALEN groups with a Baekon 2000 macromolecule transfer system (Baekon, Inc., Saratoga, Calif.) with parameters set at 6 kV, 27 pulses, 0.8 s burst, 4 cycles, 160 s (Powers et al., 1991). Briefly, channel catfish sperm were electroporated with one of the three TALEN plasmid sets, then two hundred eggs were fertilized with the electroporated sperm. Sixty minutes later, embryos were collected and incubated with the same TALEN plasmid set for 10 minutes, followed with one more electroporation. The same procedure was performed on the control group, but without plasmids.

Then embryos were moved into separate 10 L tubs filled with Holtfreter's solution (Bart and Dunham, 1996) containing 10 ppm doxycycline and incubated at 27° C. until hatch. Dead embryos were removed and water was changed daily. Channel catfish fry were then transferred into a recirculating system.

2.5 Sample Collection, DNA Extraction and Mutation Analysis

The pelvic fin and barbel of 6-month-old fingerlings were sampled for DNA analysis. Samples were digested with 100 μg/ml proteinase K followed by protein precipitation and DNA ethanol precipitation as described by Kurita et al. (2004). DNA quantity and quality were determined with gel electrophoresis and spectrophotometry.

Channel catfish LH gene β subunit specific primer, FSH gene β subunit specific primer and cfGnRH gene specific primers (Table 5) were designed and Roche Expand High FidelityPlus PCR System (Roche, Indianapolis, Ind.) was used to amplify these DNA samples. The PCR amplification procedure was as follows: initial denaturation for 2 min at 94° C.; followed by 35 cycles of 94° C. for 30 s, 60° C. for 30 s and 72° C. for min; and a final elongation for 10 min at 72° C. PCR products were examined by gel electrophoresis.

TABLE 5

Primer sequences used for the amplification of luteinizing hormone (LH) β subunit, follicle-stimulating hormone (FSH) β subunit and catfish type gonadotropin-releasing hormone (cfGnRH) in channel catfish (*Ictalurus punctatus*).

| Primer | Sequence (5'-3') | Product Size (bp) | Description |
|---|---|---|---|
| I1-F | AGGATGTCAGTGCCAGCTTC (SEQ ID NO: 9) | 572 | LH gene amplification and mutation analysis |
| I1-R | CTTGGAGTAAATGGACTCGTTG (SEQ ID NO: 10) | | |
| I2-F | CACAACTCCAGCTGTGACAA (SEQ ID NO: 126) | 511 | FSH gene amplification and mutation analysis |
| I2-R | CAGAATTCCGTGGCCATTTA (SEQ ID NO: 127) | | |
| I3-F | ATGGATGCTGTCTTTGTTTTCC (SEQ ID NO: 19) | 550 | cfGnRH gene amplification and mutation analysis |
| I3-R | CCACACGAAATAAAGGCAAAG (SEQ ID NO: 20) | | |

Gene mutations were detected through the Cel-I mutation detection assay with SURVEYOR Mutation Detection Kit (Integrated DNA Technologies, Coralville, Iowa) as described by Miller et al. (2007). Briefly, PCR products were denatured and re-annealed as follows: 94° C. 10 min; 94° C. to 85° C. -2° C./s; 85° C. to 25° C. -0.1° C./s; cooling to 4° C.; then 1 μl Enhancer S and 1 μl Nuclease S were added into 5 μl of the products above and incubated at 42° C. for 30 min. The digested PCR products were resolved on 2% UltraPure Agrose-1000 high resolution agarose gel (Invitrogen, Grand Island, N.Y.).

2.6 TA Clone and Sequencing

LH, FSH and cfGnRH genes from the mutated fingerlings were amplified and were purified with IsoPure DNA Purification Kit (Denville, Holliston, Mass.), and then inserted into the vector of TOPO TA Cloning Kit for Sequencing (Invitrogen, Grand Island, N.Y.) and transformed into the One Shot TOP10F' Chemically Competent *E. coli* (Invitrogen, Grand Island, N.Y.). Colonies were selected from a LB agar plate containing 100 μg/ml ampicillin.

Ten colonies corresponding to each individual carrying mutated genes were picked and amplified. The bacteria glycerol stock were added into 96-well plates and sent to Eurofins Genomics Company (Louisville, Ky.) for sequencing.

Upon receiving the results, the quality was checked and the sequences were aligned with the wild type channel catfish LH, FSH and cfGnRH genes using the online multiple sequence alignment tool Clustal Omega (http://www.ebi.ac.uk/Tools/msa/clustalo/), respectively.

2.7 Plasmid Integration Inspection

To determine the presence of plasmids integrated into the channel catfish genome or persisting in the cytoplasm, two pairs of specific primers (Table 6) for each set of the TALEN plasmids targeting LH, FSH and cfGnRH genes were designed to detect the plasmid DNA in corresponding mutated channel catfish. The amplification regions of these two primers were the CMV promoter region and TAL repeats region, respectively. The PCR procedure was the same as above of amplifying LH, FSH and cfGnRH genes and products were inspected with electrophoresis

TABLE 6

Primer sequences used for the detection of transcription activator-like effector nuclease (TALEN) plasmids targeting channel catfish (*Ictalurus punctatus*) luteinizing hormone (LH) gene, follicle-stimulating hormone (FSH) gene and catfish type gonadotropin-releasing hormone (cfGnRH) gene.

| Primer | Sequence (5'-3') | Product Size (bp) | Description |
|---|---|---|---|
| LI1-F | AACAACAACGGCGGTAAG (SEQ ID NO: 128) | 323 | TALEN LH plasmids integration detection |
| LI1-R | TTCCCTCCATTGTTATTCGC (SEQ ID NO: 129) | | |
| LI2-F | GCGAATAACAATGGAGGGAA (SEQ ID NO: 130) | 318 | TALEN LH plasmids integration detection |
| LI2-R | GTCGTGGGATGCAATGG (SEQ ID NO: 131) | | |
| FI1-F | GCAAATAATAACGGTGGCAA (SEQ ID NO: 132) | 124 | TALEN FSH plasmids integration detection |
| FI1-R | GTTTCCCTCCGTCATGCG (SEQ ID NO: 133) | | |
| FI2-F | GCGAATAACAATGGAGGGA (SEQ ID NO: 134) | 324 | TALEN FSH plasmids integration detection |
| FI2-R | GCCACCGTTATTATTTGCAA (SEQ ID NO: 135) | | |
| GI1-F | AACAACAACGGCGGTAAG (SEQ ID NO: 136) | 114 | TALEN cfGnRH plasmids integration detection |
| GI1-R | CCCATTATTGTTCGCGATTG (SEQ ID NO: 137) | | |
| GI2-F | GCATGACGGAGGGAAAC (SEQ ID NO: 138) | 215 | TALEN cfGnRH plasmids integration detection |
| GI2-R | CCATTATTGTTCGCGATTGA (SEQ ID NO: 139) | | |

2.8 Statistical Analysis

Mutation rates, hatch rates and survival rates from TALEN sets targeting different genes were analyzed utilizing Fisher's Exact Test and Pearson's Chi-square Test (McDonald, 2014). All analysis were performed with statistical software R (version 3.1.3).

3 Results

3.1 Hatch Rate and Survival Rate

Two hundred eggs were double electroporated for the three TALEN treatment groups and the one control group. For the TALEN-LH group, 67 hatched with a hatch rate of 33.5% (Table 7). Eighty of 200 eggs hatched for the TALEN-FSH group (40%), while 76 hatched in TALEN-GnRH group (36.5%). No significant difference exited among different groups (Pearson's Chi-square Test, p=0.387). At 6 months, the fry survival of the TALEN-LH, TALEN-FSH and TALEN-GnRH groups was 56.7%, 71.3% and 67.1%, respectively, which was not different among groups (Fisher's Exact Test, p=0.182).

TABLE 7

Comparison of the embryo hatch rate and fry survival rate for channel catfish (*Ictalurus punctatus*) treated with transcription activator-like effector nucleases (TALENs) targeting luteinizing hormone (LH) gene, follicle-stimulating hormone (FSH) gene or catfish type gonadotropin-releasing hormone (cfGnRH) gene.

| Constructs | Eggs | Fry hatched | Hatch rate (%)* | Fry survival | Survival rat (%)† |
|---|---|---|---|---|---|
| TALEN-LH | 200 | 67 | 33.5 | 38 | 56.7 |
| TALEN-FSH | 200 | 80 | 40.0 | 57 | 71.3 |
| TALEN-GnRH | 200 | 76 | 36.5 | 51 | 67.1 |
| Control | 200 | 84 | 44.0 | 63 | 75.0 |

*No significant difference exits either among different treatment groups (p = 0.387), or between treatment groups and the control group (p = 0.340).
†No significant difference exits either among different treatment groups (p = 0.182), or between treatment groups and the control group (p = 0.107).

Two hundred eggs in control group has a hatch rate of 44.0% (84 of 200) and a survival rate of 75.0% (63 of 84). When comparing with the treatment groups, there is no significant difference exists on both hatch rate (Pearson's Chi-square Test, p=0.340) and survival rate (Fisher's Exact Test, p=0.107).

3.2 Mutation Rate

Figure 12:
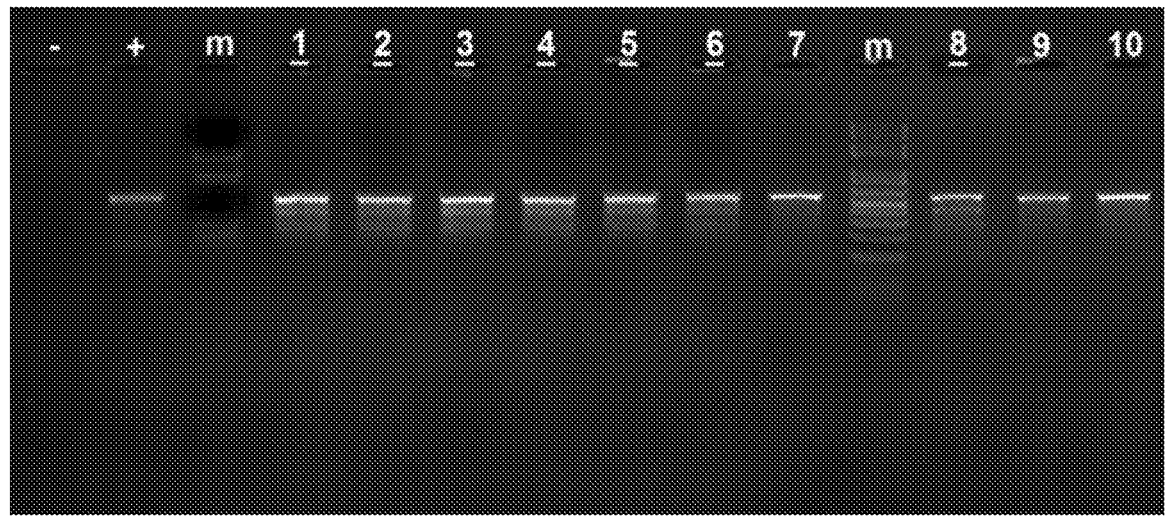
FIG. 12. Identification of edited luteinizing hormone (LH) gene in channel catfish (*Ictalurus punctatus*) using Cel-I mutation detection assay.

As indicated by the three bands evident for some individual on the gel shown in FIG. 12, individuals exposed to TALENs targeting channel catfish LH gene had a 44.7% mutation rate (Table 8). None of the individuals in the control group were mutated.

TABLE 8

Mutation rate of channel catfish (*Ictalurus punctatus*) electroporated with transcription activator-like nuclease (TALEN) plasmids targeting luteinizing hormone (LH) gene, follicle-stimulating hormone (FSH) gene or catfish type gonadotropin-releasing hormone (cfGnRH) gene.

| TALEN sets | Concentration (µg/ml) | N fry | N mutated fry | Mutation rate (%) |
|---|---|---|---|---|
| LH | 25 | 38 | 17 | 44.7 |
| FSH | 25 | 57 | 31 | 63.2 |
| cfGnREI | 25 | 51 | 27 | 52.9 |
| Control | 0 | 63 | 0 | 0 |

Figure 13:
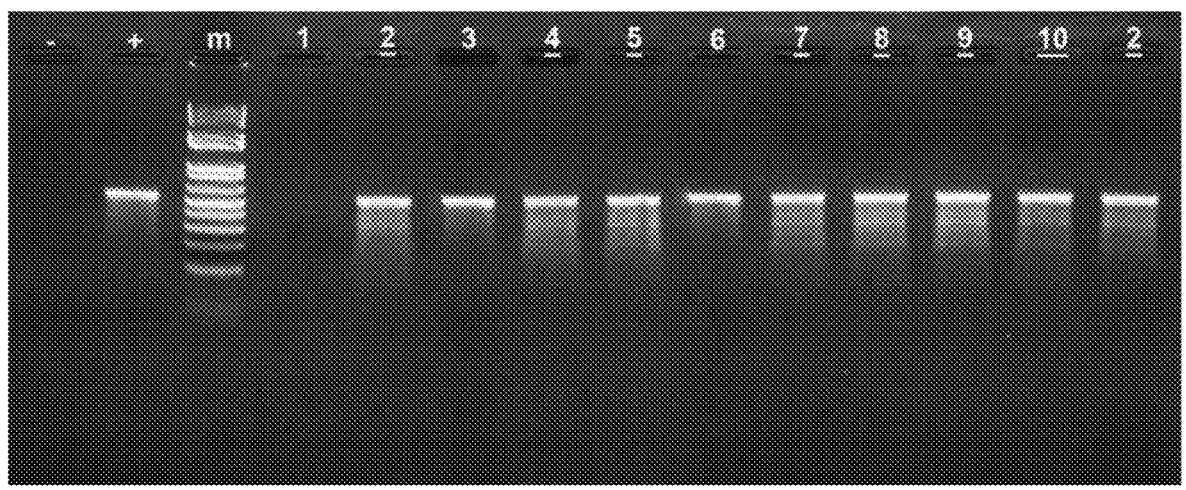
FIG. 13. Identification of edited follicle-stimulating hormone (FSH) gene in channel catfish (*Ictalurus punctatus*) using Cel-I mutation detection assay.

The FSH gene was successfully mutated in 31 of 57 channel catfish fingerlings which had a 63.2% mutation rate (Table 8, FIG. 13). In the group electroporated with TALEN plasmids targeting the cfGnRH gene, the mutation rate was 52.9% (Table 8). Two patterns of DNA bands, both of which indicated the cfGnRH gene mutation, could be found on the gel, one with three bands and the other with five bands (FIG. 14).

3.3 Sequence Modification of the Mutated LH, FSH and cfGnRH genes

Sequencing and alignment results confirmed that channel catfish were successfully mutated for the LH gene, multiple types of mutations were generated. Most of the mutations occurred as one to five base deletions within the TALEN target cutting site; some changes were base substitutions and the remainder were in the form of base insertions (FIG. 15). Unlike the ZFN experiment, the TALEN technology introduced mutations located within the expected cutting site of the LH gene, and thus showed higher specificity in the gene editing process. The mutation should lead to a frame-shift or early termination in transcription and the LH amino acid sequences will be altered, disrupting normal LH function.

Analysis of the sequence information from the FSH gene mutated individuals and cfGnRH gene mutated individuals generated similar results as for the LH gene. All the mutations occurred within the TALEN cutting site, and base deletion, substitution and insertion were found for both genes (FIG. 16, FIG. 17). All of these mutations were introduced in the ORF region, which should disrupt the corresponding normal gene functions.

3.4 TALEN Plasmids Integration Evaluation

Figure 18:
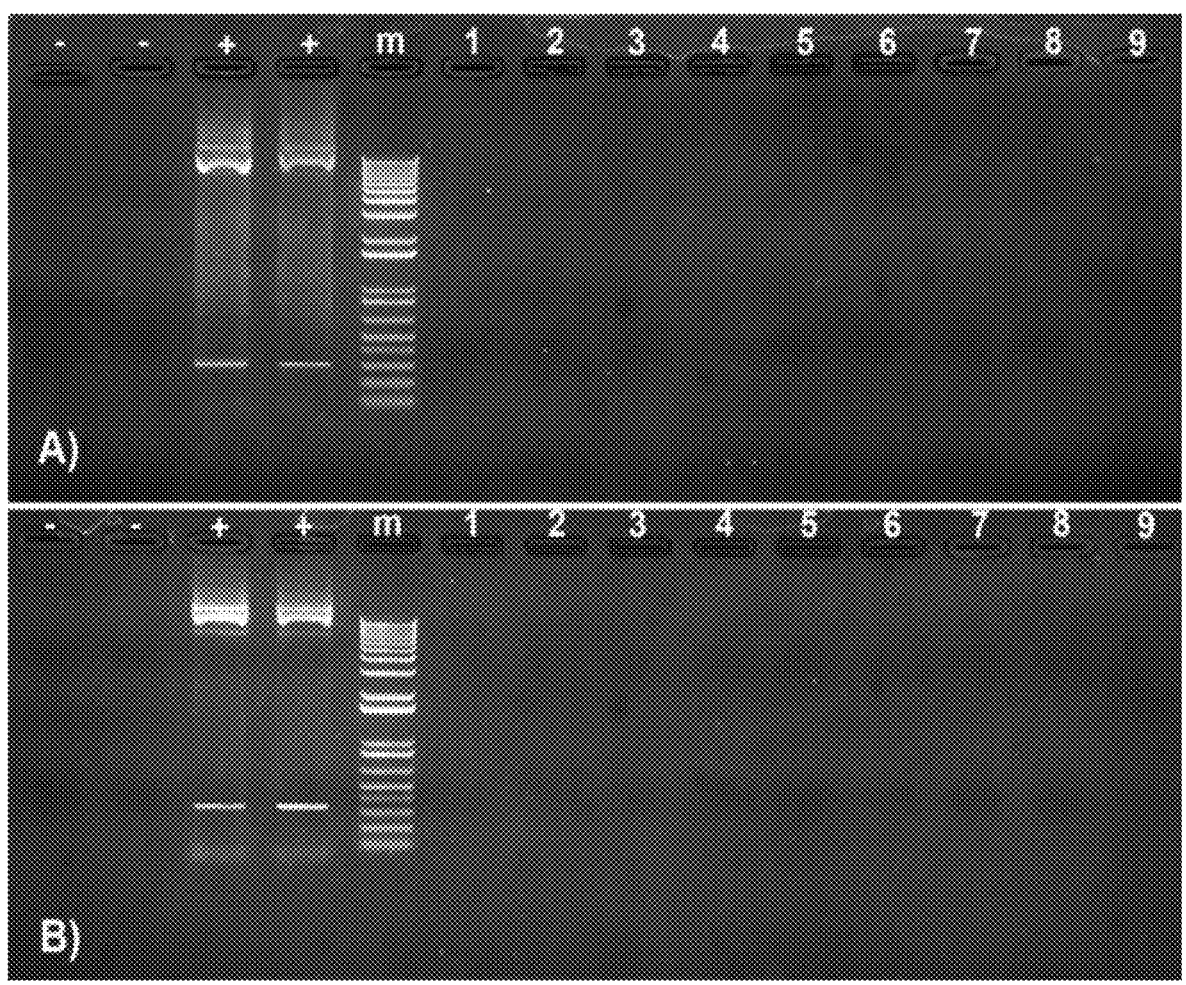
FIG. 18. PCR inspection of transcription activator-like effector nucleas (TALEN) plasmids (targeting the luteinizing hormone (LH) gene) integration into channel catfish (*Ictalurus punctatus*) genome.
Figure 19:
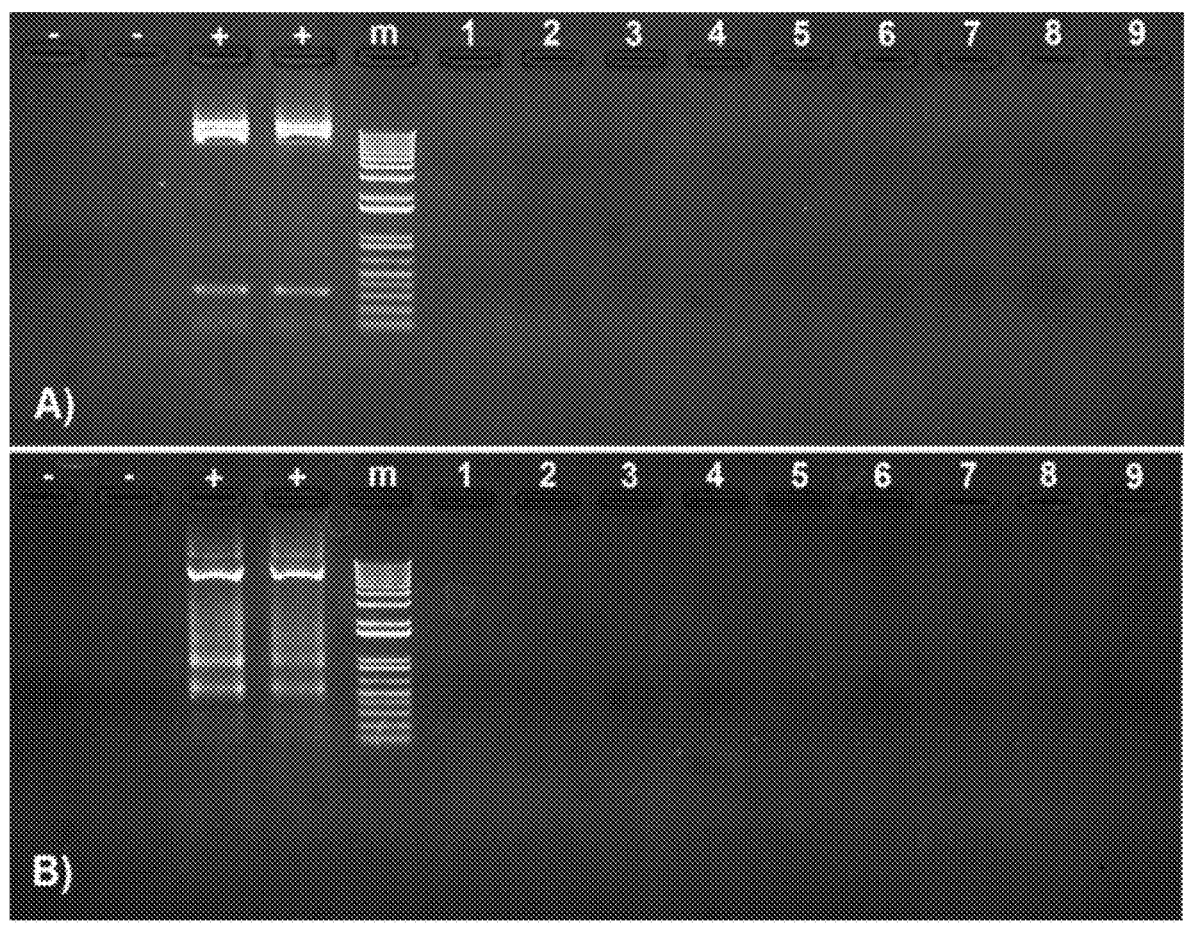
FIG. 19. PCR inspection of transcription activator-like effector nuclease (TALEN) plasmids (targeting the follicle-stimulating hormone (FSH) gene) integration into channel catfish (*Ictalurus punctatus*) genome.
Figure 20:
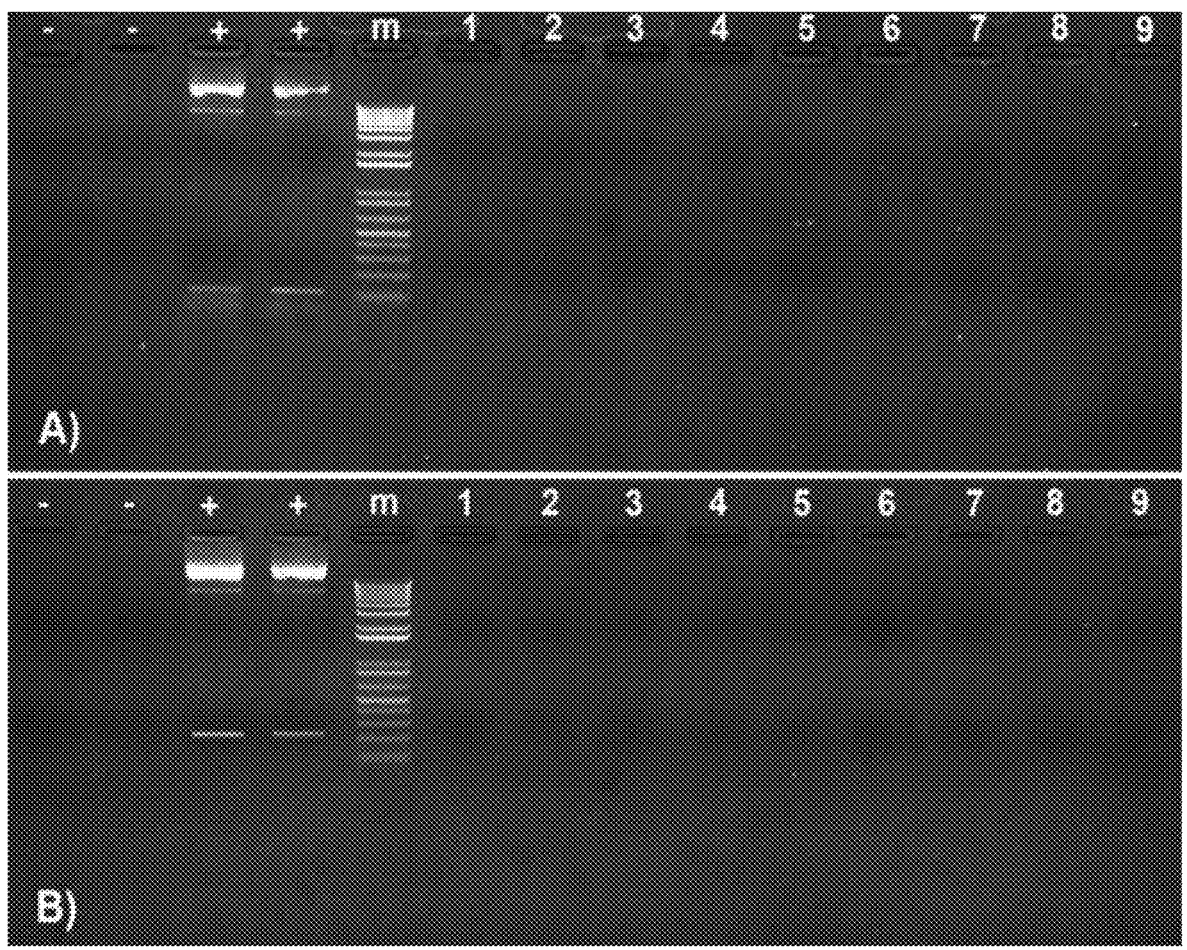
FIG. 20. PCR inspection of transcription activator-like effector nuclease (TALEN) plasmids (targeting the catfish type gonadotropin-releasing hormone (cfGnRH) gene) integration into channel catfish (*Ictalurus punctatus*) genome.

Two pairs of TALEN plasmids specific primers (Table 6), which amplify the CMV promoter or TAL repeats region of each TALEN sets, were used to detect the presence of plasmids DNA in all mutated individuals. Similar to the results of ZFNs experiment, no plasmid DNA was detected with PCR for all TALEN-LH (FIG. 18), TALEN-FSH (FIG. 19) and TALEN-GnRH (FIG. 20) mutated fish. None of the channel catfish fingerlings carried the exogenous DNA.

4 Discussion

Gene mutation targeting channel catfish LH gene, FSH gene and cfGnRH gene, using the engineered TALEN technology and electroporation was accomplished. The mutation rate varied among groups targeted for the different genes, ranging from 44.7% to 63.2%. The hatch rate and survival rate of these treatment groups were not different from the control group. Apparently, the TALEN technology did not have any negative effects on the development of embryos and fry. Thus, off-target mutations did not occur or did not affect genes important for development and early survival. A variety of mutations were induced including deletions, additions and substitutions. This is the first report of using TALENs to induce mutations in a major US aquaculture species.

TALEN has been proved a powerful approach to introduce DNA mutations in a number of animal models, including worm (*Bombyx mori*) (Ma et al., 2012), fruit fly (*Drosophila*) (Liu et al., 2012), ascidian (*Ciona intestinalis*) (Treen et al., 2014), frog (*Xenopus tropicalis*) (Lei et al., 2012), rat (*Rattus norvegicus*) (Tesson et al., 2011; Mashimo et al., 2013) and livestock (Carlson et al., 2012). In teleost, TALENs have been utilized to investigate gene function in medaka (*Oryzias latipes*) (Ansai et al., 2013), yellow catfish (*Tachysurus fulvidraco*) (Dong et al., 2014), and mostly in zebrafish (*Danio rerio*) (Huang et al., 2011; Sander et al., 2011; Cade et al., 2012; Moore et al., 2012). The mutation rates of TALEN varies in different species. In zebrafish the mutation rate ranged from 2.0% to 76.8% (Bedell et al., 2012; Cade et al., 2012; Dahlem et al., 2012; Moore et al., 2012), and in medaka the mutation rate could be as high as 100% in some cases (Ansai et al., 2013). In the current experiment, the mutation rate for channel catfish LH gene, FSH gene and cfGnRH gene were 44.7%, 63.2% and 52.9%, respectively, which was relatively high compared to rates in other species.

TALEN mutation rates are generally higher compared to ZFN, and as much as 10 times higher in some cases (Chen et al., 2013). In the current experiment, the mutation rate of TALEN exposed embryos, 44.7%, 63.2% and 52.9% for TALEN-LH, TALEN-FSH and TALEN-GnRH, respectively, were all significantly higher than that of ZFNs group (19.7%, see Chapter II) when analyzing with Fisher's Exact Test (p=0.0125, p=0.0001, p=0.0003). Meanwhile band intensity in Cel-I assay results were darker and more distinct in the TALEN groups (FIG. 12, FIG. 13, FIG. 14) than that in the ZFN groups (FIG. 5), which means higher mutation efficiency was achieved using TALEN (Qiu et al., 2004). More bands were obtained in some of cfGnRH mutated individuals, indicating more mutations may exist. Multiple mutations were not found in a single individual and a potential reason could be we only picked up 10 colonies of each mutated individual for sequencing. It may be possible to discover more mutations with further more sequencing and alignment analysis. All the evidence indicated TALEN technology has better efficiency than ZFN when performing targeted gene manipulation.

The sequences of the detected mutations in this experiment were all located within the designed TALEN cutting sequence for all three TALENs targeting channel catfish LH gene, FSH gene and cfGnRH gene. Nucleotide deletion, insertion and substitution were all observed. All these modifications were in the ORF of the corresponding genes, and will lead to a change of amino acid sequence, which likely will disable gene function. In contrast, in the ZFN experiment (Chapter I1), off-target mutations occurred outside the supposed site, but within the targeted gene ORF. This phenomenon was also observed in other species, such as zebrafish (Meng et al., 2008; Gupta et al., 2011), when using ZFN technology. TALEN had higher specificity than ZFN when utilized in the current targeted gene editing studies on channel catfish.

Almost all previous targeted gene editing work using TALEN or ZFN technology was conducted with microinjection of mRNA into cells (Doyon et al., 2008; Ansai et al., 2012; Cade et al., 2012; Moore et al., 2012). Although mutation rates from microinjection of TALEN mRNA is high in these studies (Cade et al., 2012; Moore et al., 2012), this technique is a time and labor consuming process and it is difficult to produce a large number of mutated individuals in a short time. Electroporation is an alternative method to introduce exogenous nucleic acid into cells, but has been rarely utilized in gene editing research. Only a few studies were conducted with electroporation and most of them performed on cultured cells. But there is a research that TALEN plasmids were electroporated into ascidian (*Ciona intestinalis*) embryos and successfully mutated target genes (Treen et al., 2014). Utilizing electroporation we successfully mutated channel catfish LH gene, FSH gene and cfGnRH gene, by delivering TALEN plasmids instead of mRNA into channel catfish embryos in this study. The mutation rate from electroporation of TALEN plasmids was as high as 63.2%, which was a higher mutation rate than what was obtained in other studies that utilized microinjection of TALEN mRNA. This process is much easier than microinjection, avoids the degradation problems, requires less time and effort and could produce large amount of mutated fish in a short time. Additionally, plasmid DNA did not integrate into channel catfish genome (FIG. 18, FIG. 19, FIG. 20), resulting in mutated non-transgenic channel catfish. Based upon the results of both the ZFN and TALEN experiments with channel catfish, electroporation is a good technique for targeted gene editing without inducing transgenesis.

Cell toxicity is an issue in the gene targeting mutation studies. Cell death and apoptosis are most likely associated with off-target effects created by these technologies. ZFNs are reported to have relatively high off-target effects in previous studies (Gupta et al., 2011). In contrast, TALENs generally have low incidence of off-target effects and thus low cell toxicity (Mussolino et al., 2011; Zhu et al., 2013; Liu et al., 2014). Our experimental results showed that both the embryo hatch rate and fry survival rate of TALEN treatment groups was not different than that of the control group, indicating that introduction of TALEN plasmids and the resulting mutations did not increase the embryo and fry mortality, and were likely on target. Thus, the results with channel catfish are consistent with previous results, indicating than TALEN technology gives higher mutation rate and lower cell toxicity and is a better method to induce gene editing on the genomic level compared to ZFN technology and even when electroporation of plasmids is utilized.

TALENs with low off-target effect have multiple benefits on commercial application. The low cost of design and assembly of TALENs enables large scale application in aquaculture industry. Low off-target effect reduces the cell toxicity of gene editing and does not influence embryo hatching and fry survival, will not dramatically increase the initial investment. In addition, TALENs decrease other unwanted gene modifications and thus will not change the good commercial trials and not affect production and profit. However, pleiotropic effects of the mutant allele will need evaluation to ensure no adverse effects on economically important traits.

If the editing of LH gene, FSH gene or cfGnRH gene using TALENs results in sterilization, it could be applied to overcome potential environmental risk, as well as combining with other fish genetic enhancement programs to profit aquaculture industry.

5 Conclusion

A simple, convenient and efficient method of targeted gene editing with TALEN technology in channel catfish *I. punctatus* was demonstrated. TALEN plasmids targeting channel catfish LH β subunit, FSH β subunit and cfGnRH gene were introduced into fertilized eggs with electroporation and these reproductive related genes were successfully mutated. This is the first time that an aquaculture species in the US was gene edited at the genomic level with TALENs.

Further study is needed to evaluate the reproductive status of LH, FSH and cfGnRH mutated individuals when they reach sexual maturity. The restoration of fertility with hormone therapy will also need to be developed to allow production of fertile brood stock to complete the reversible sterilization in channel catfish.

Example 3—Gene Editing of Luteinizing Hormone and Gonadotropin-Releasing Hormone Genes to Sterilize Channel Catfish, Ictalurus punctatus, Using Clustered Regularly Interspaced Short Palindromic Repeat/Cas9 Technology Abstract Clustered regularly interspaced short palindromic repeats (CRISPR)/Cas9 system is a powerful new research tool that enables targeted gene editing in a wide variety of animals. Here we demonstrate efficient targeted mutagenesis in channel catfish (*Ictalurus punctatus*), the most important freshwater aquaculture species in the US. CRISPR/Cas9 was utilized targeting channel catfish luteinizing hormone (LH) and catfish type gonadotropin-releasing hormone (cfGnRH) genes to generate sterile channel catfish. CRISPR/Ca9 plasmids were electroporated into embryos to mutate LH and cfGnRH genes, while CRISPR/Cas9 RNAs were microinjected into embryos to target cfGnRH gene. Both methods successfully produced mutations that were confirmed with Cel-I assay and sequencing. The mutation rates for the electroporation were 37.5% and 38.5%, while it is 100% when using microinjection. However, the egg hatch rate was only 9.0% using microinjection and lower than that of electroporation, 23.0% and 21.0% (Fisher's Exact Test, p=0.008). The electroporated plasmids were eventually degraded without integration as they were not detectable in mutated individuals using PCR. If the editing of these genes results in sterilization, several applications could be explored to profit the catfish industry and overcome potential environmental risk of various genetic manipulations.

Introduction

Recent advances in the study of prokaryotic clustered regularly interspaced short palindromic repeats (CRISPR) adaptive immune system provide an alternative genome editing approach. The CRISPR/CRISPR-associated (Cas) system is a microbial adaptive immune system that uses RNA-guided nucleases to cleave foreign genetic elements that protects bacteria and archaea from invading viruses and plasmids (Deveau et al., 2010; Bhaya et al., 2011; Makarova et al., 2011; Chang et al., 2013). Three major types of CRISPR (types I-III) have been categorized on the basis of locus organization and conservation (Makarova et al., 2011), wherein each system comprises a cluster of Cas genes, noncoding RNAs and a distinctive array of repetitive elements (direct repeats). These repeats are interspaced by short variable sequences derived from exogenous DNA targets known as protospacers, and together they constitute the CRISPR RNA (crRNA) array (Makarova et al., 2011). Within the DNA target, each protospacer is always associated with a protospacer adjacent motif (PAM), which can vary depending on the specific CRISPR system (Ran et al., 2013).

The type 1 CRISPR system is one of the best characterized (Gasiunas et al., 2012; Jinek et al., 2012), which consists of the nuclease Cas9, the crRNA array that encodes the guide RNAs and a required auxiliary trans-activating crRNA (tracrRNA) that facilitates the processing of the crRNA array into discrete units. Each crRNA unit then contains a 20-nt guide sequence and a partial direct repeat, where the former direct Cas9 to a 20-bp DNA target. The crRNA and tracrRNA can be fused together to create a chimeric, single-guide RNA (sgRNA) (Ran et al., 2013). Cas9 can thus be re-directed toward almost any target of interest in immediate vicinity of the PAM sequence by altering the 20-nt guide sequence within the sgRNA. Similarly to zinc finger nucleases (ZFNs) and transcription activator-like effector nucleases (TALENs), Cas9 promotes genome editing by stimulating a double-strand break (DSB) at target locus. Upon cleavage by Cas9, the target locus typically undergoes the NHEJ and HDR. In the absence of a repair template, DSBs are re-ligated by the NHEJ process, which leaves scars in the form of insertion/deletion (indel) mutations, which can lead to frameshift and premature stop codons.

Cas9 offers several potential advantages, including the ease of customization, higher targeting efficiency and the ability to facilitate multiplex genome editing. Cas9 can be easily retargeted to new DNA sequences by simply change the 20-nt guide sequence. The Cas9 derived from *Streptococcus pyogenes* is known to make a DSB between the 17th and 18th bases in the target sequences (Jinek et al., 2012), whereas TALENs cleave nonspecifically in the 12-24 bp linker between the pair of binding sites. There is a requirement for the Cas9 target sites, which is the presence of a PAM sequence directly 3' of the 20-bp target sequence. Also Cas9 can be used to target multiple genomic loci simultaneously by co-delivering a combination of sgRNAs (Jao et al., 2013).

CRISPR/Cas9 system has been successfully utilized in many animals for the gene function disruption, such as nematode (*Caenorhabditis elegans*) (Friedland et al., 2013; Ward, 2015), fruit fly (*Drosophila*) (Gratz et al., 2013), frog (*Xenopus tropicalis*) (Nakayama et al., 2013), zebrafish (*Danio rerio*) (Chang et al., 2013; Hwang et al., 2013; Jao et al., 2013; Xiao et al., 2013), mice (Wang et al., 2013; Shen et al., 2013; Wu et al., 2015) and human cells (Cong et al., 2013; Hwang et al., 2013; Mali et al., 2013). Higher efficiency and lower cell toxicity have been reported.

Channel catfish (*Ictalurus punctatus*) and its hybrid, channel catfish ♀ X blue catfish (*Ictalurus furcatus*) ♂, are the most important aquaculture organism in the US, however the catfish farming is in crisis recently (Hanson and Sites, 2012). A effective method to improve the production and efficiency is exploring fish genetics (Dunham, 2011) but sterilization is needed to prevent potential environmental and ecological risk for certain genetic manipulations.

Gonadotropin-releasing hormone (GnRH) regulates reproduction (Fernald and White, 1999) and stimulates the synthesis of gonadotropin. Luteinizing hormone (LH) stimulates the steroid hormone secretion, boosts ovarian and testicular function and plays a key role during gonadal maturation and spermiation/ovulation (Levavi-Sivan et al., 2010). Deactivating LH and GnRH genes function has the potential possibility of inducing fish sterilization.

In this study, we utilize CRISPR/Cas9 technology for the targeted gene disruption of LH gene and cfGnRH gene, to sterilize channel catfish. Both electroporation and microinjection approaches were performed and evaluated, and we aim to produce sterile channel catfish with CRISPR/Cas9 targeted gene editing.

Figure 21:
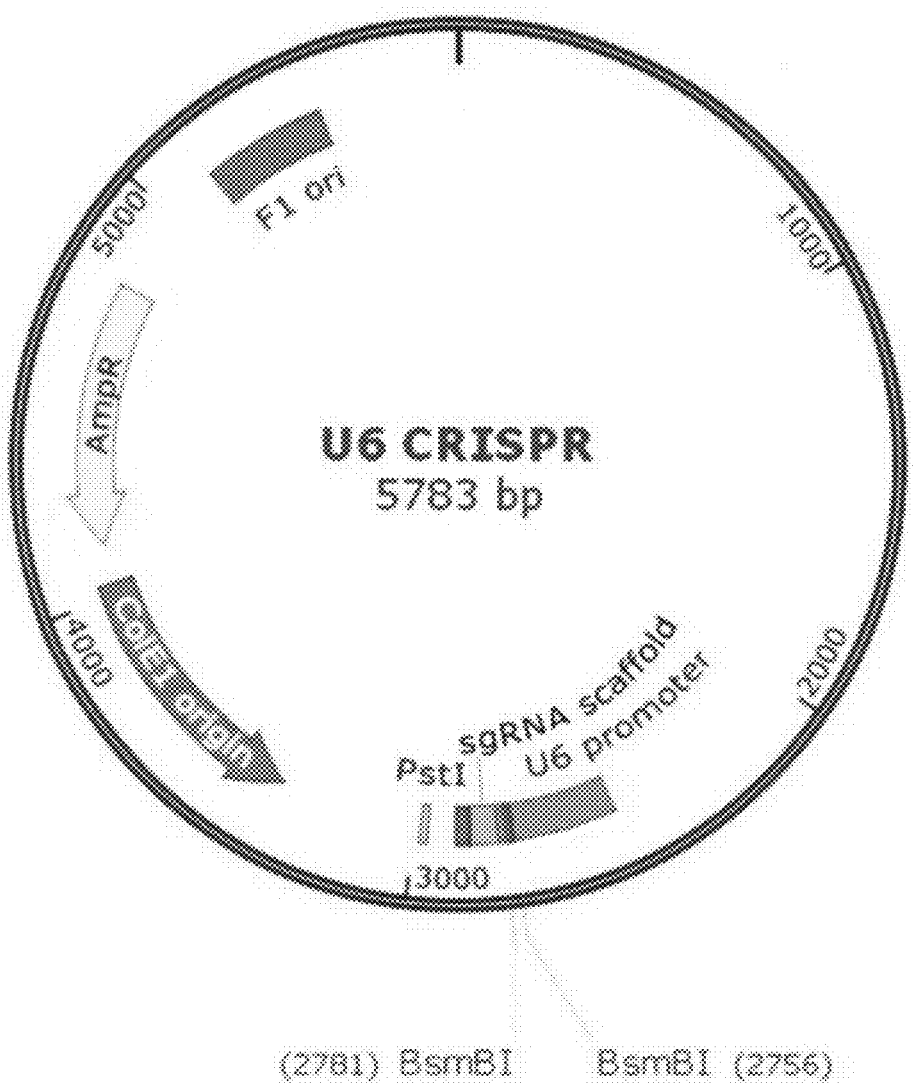
FIG. 21. Schematic representation of clustered regularly interspaced short palindromic repeats (CRISPR) sgRNA plasmid used for targeting channel catfish (*Ictalurus punctatus*) luteinizing hormone (LH) gene and catfish type gonadotropin-releasing hormone (cfGnRH) gene with eletroporation.

2 Material and Methods 2.1 Construction of the CRISPR sgRNA and Cas9 Nuclease Plasmids The CRISPR/Cas9 system was utilized in this project to mutate channel catfish (*I. punctatus*) LH gene β subunit (AF112192) (Liu et al., 2001) and the cfGnRH gene (data unpublished) for sterilization. To mutate these two genes using electroporation, CRISPR sgRNA plasmids were obtained from the Transposagen Company (Lexington, Ky.). These plasmids (CRISPR/LH-U6 and CRISPR/GnRH-U6) were driven by the U6 promoter, and the sgRNA scaffold was fused following the promoter (FIG. 21). Ampicillin resistance element was also inserted to assist selection.

Figure 22:
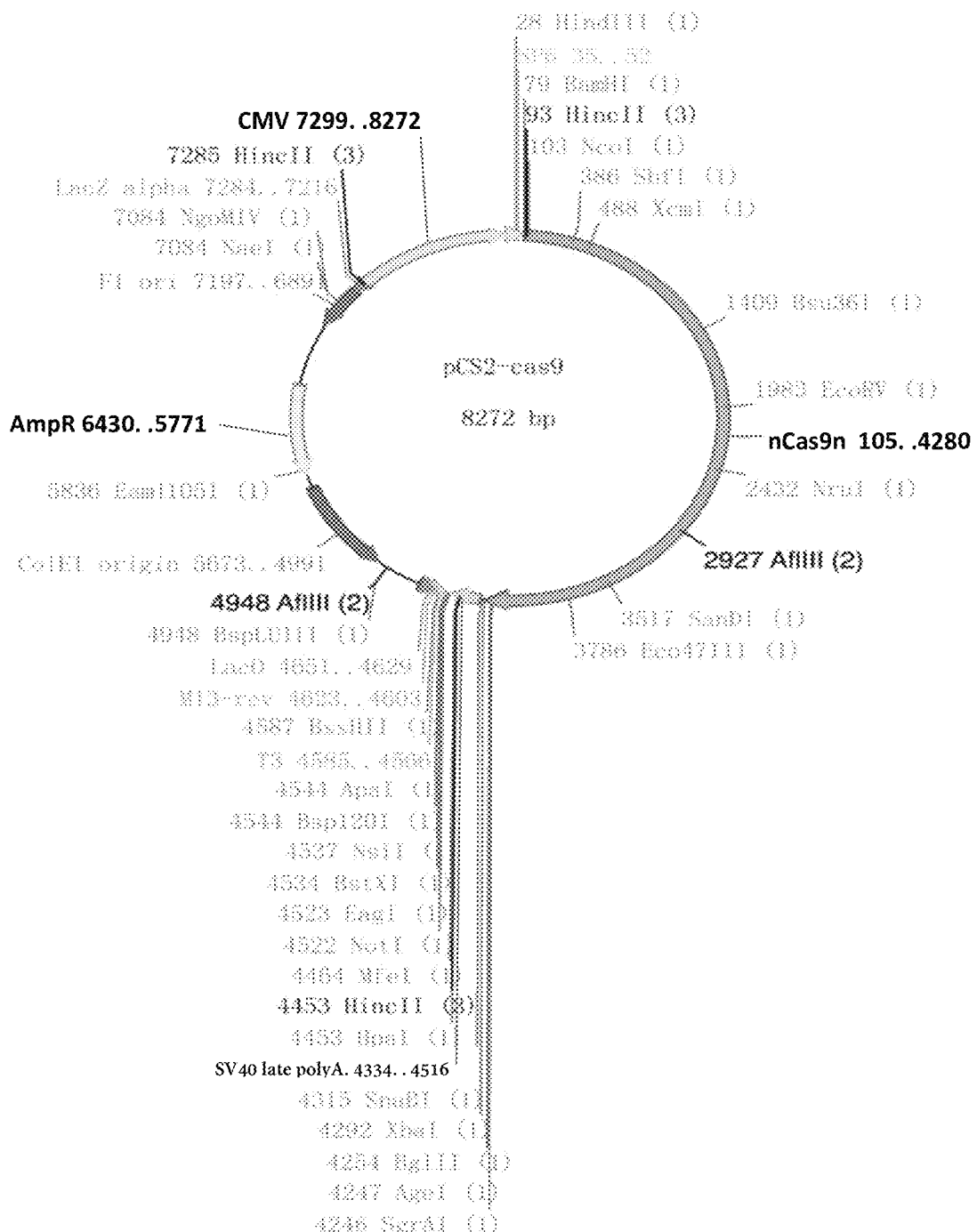
FIG. 22. Schematic representation of Cas9 endonuclease plasmid used for electroporation targeting channel catfish (*Ictalurus punctatus*) luteinizing hormone (LH) and catfish type gonadotropin releasing hormone (cfGnRH).

The Cas9 plasmid (pCS2-nCas9n), which was electroporated together with the two CRISP-U6 sgRNA plasmids, was obtained from Addgene (Cambridge, Mass.). pCS2-nCas9n plasmid was driven by the CMV promoter and contains the ampicillin selection element (FIG. 22).

Figure 23:
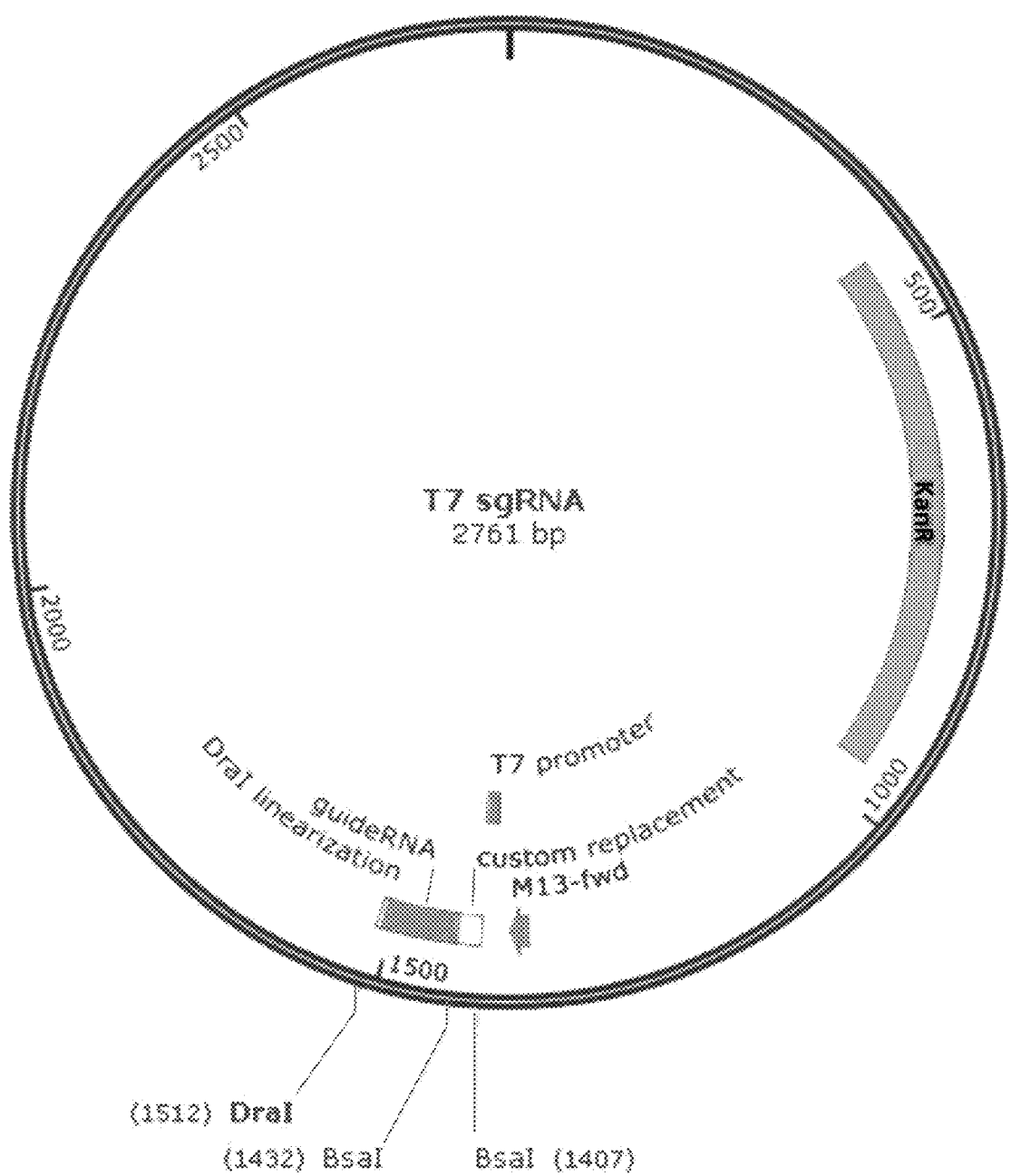
FIG. 23. Schematic representation of clustered regularly interspaced short palindromic repeats (CRISPR) sgRNA plasmid used for in vitro RNA synthesis and targeting channel catfish (*Ictalurus punctatus*) catfish type gonadotropin-releasing hormone (cfGnRH) gene.
Figure 24:
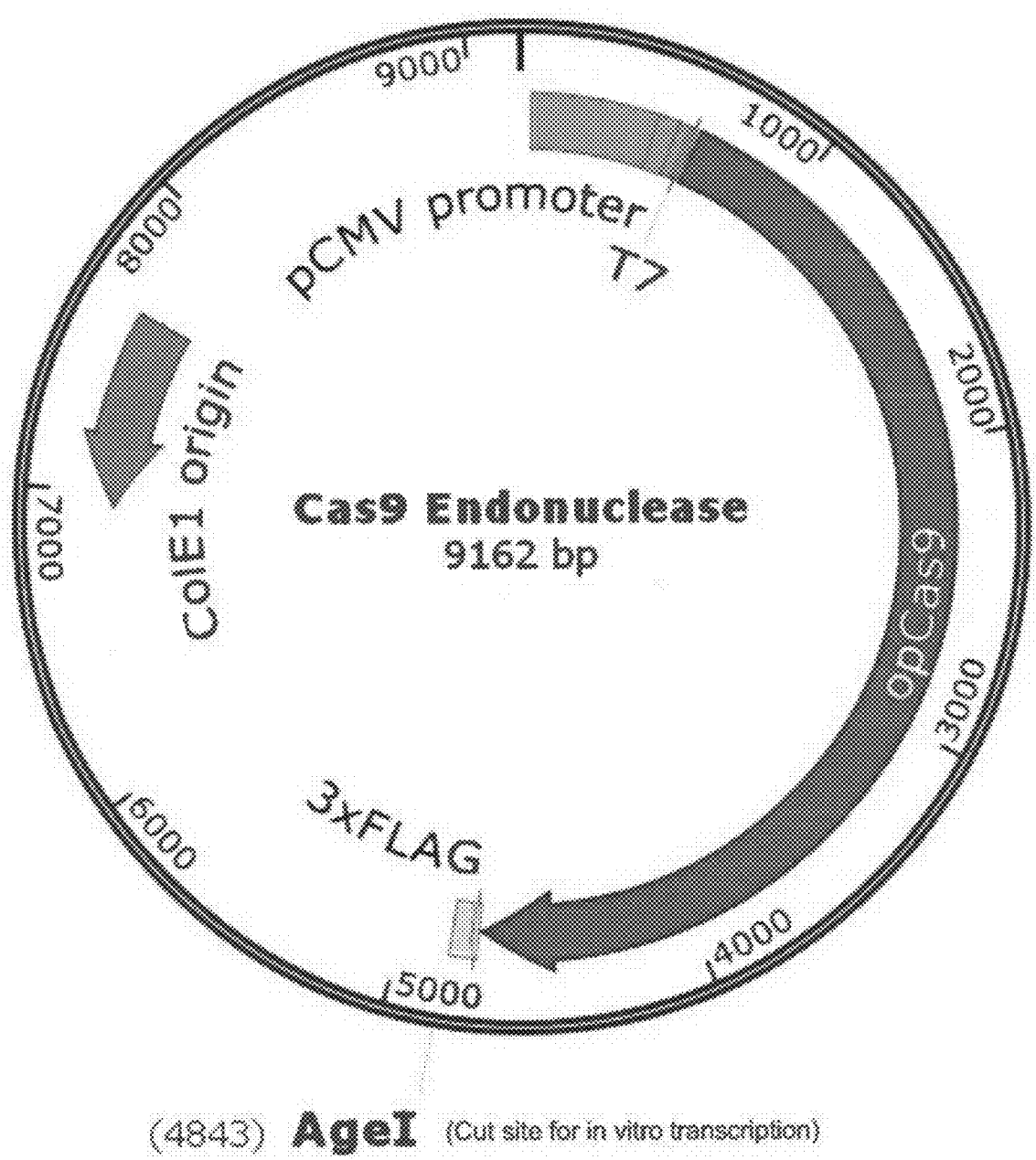
FIG. 24. Schematic representation of Cas9 endonuclease plasmid used for in vitro mRNA synthesis and microinjection targeting channel catfish (*Ictalurus punctatus*) catfish type gonadotropin releasing hormone (cfGnRH) gene.

The CRISPR plasmid (CRISPR/GnRH-T7) and Cas9 plasmid (Cas9-T7) utilized to mutate cfGnRH gene with microinjection technique were obtained from Transposagen Company (Lexington, Ky.). CRISPR/GnRH-T7 plasmid was driven by T7 promoter and contains the kanamycin resistance element (FIG. 23), while the Cas9-T7 plasmid was driven by both CMV and T7 promoters (FIG. 24).

Figures 25, 26:
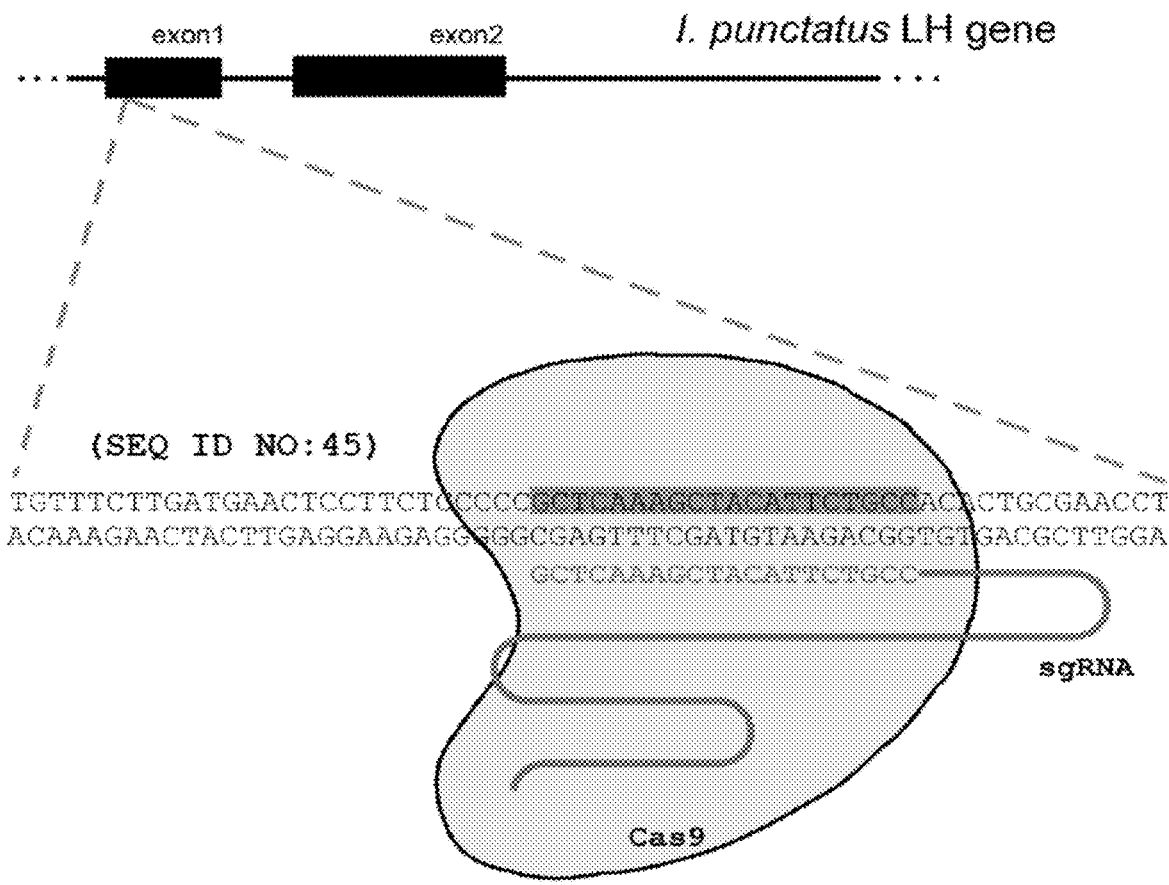
FIG. 25. Clustered regularly interspaced short palindromic repeats (CRISPR) plasmid sets targeting channel catfish (*Ictalurus punctatus*) luteinizing hormone (LH) gene and catfish type gonadotropin-releasing hormone (cfGnRH) gene.
FIG. 26. The location of the clustered regularly interspaced short palindromic repeats (CRISPR) target site in the channel catfish, *Ictalurus punctatus*, luteinizing hormone (LH) gene.

The target sequences of sgRNA plasmids in channel catfish LH gene and cfGnRH gene are shown in FIG. 25.

The targeting site of LH gene was located in the first exon (FIG. 26) and the targeting sire of cfGnRH was in the third exon. Upon successful mutation, both of them should interrupt the normal gene function.

2.2 Plasmid Preparation

The CRISPR/LH-U6, CRISPR/GnRH-U6 and pCS2-nCas9n plasmids were transformed into One Shot Top 10F" Chemically Competent *E. coli* (Invitrogen, Grand Island, N.Y.) and 100 µl transformation mix of each plasmid was used to spread on the LB agar plate with 100 µg/ml ampicillin. Single colonies were pick up and cultured in 400 ml LB broth with 100 µg/ml ampicillin and plasmids were then extracted with the IsoPure Plasmid Maxi II Prep Kit (Denville, Holliston, Mass.). The quality and quantity were examined with gel electrophoresis and spectrophotometry. The same procedure was performed to amplify CRISPR/GnRH-T7 plasmids with the only modification of using 50 µg/m kanamycin.

CRISPR/LH-U6 plasmids and CRISPR/GnRH-U6 plasmids were mixed together with pCS2-nCas9n plasmids, respectively, and diluted with 2 ml saline (0.9% NaCl) to the final concentration of 25 µg/ml each for the first electroporation of sperm. Additionally, plasmids were diluted with 5 ml TE buffer (5 mM Tris-HCl, 0.5M EDTA, pH=8.0), for the second electroporation of embryos.

2.3 mRNA Preparation

The CRISPR/GnRH-T7 plasmid and Cas9-T7 plasmid were utilized for in vitro transcription of sgRNA and Cas9 mRNA, used for the targeted mutation of channel catfish cfGnRH gene by microinjection. Plasmids were first linearized with restricted endonuclease digestion. Ten µg of CRISPR/GnRH-T7 was mixed with 4 µl DraI (20 U/µl) (NEB, Ipswich, Mass.), 5 µl NEBuffer (10×) and diluted with water to 50 Id. 10 g Cas9-T7 plasmids was mixed with 16 µl Agel (5 U/l) (NEB, Ipswich, Mass.), 5 µl NEBuffer (10×) and diluted to 50 µl. Digestion systems were incubated 37° C. for 2 hours. Linearized plasmids were inspected with gel electrophoresis and purified with MinElute Reaction Cleanup Kit (Qiagen, Valencia, Calif.).

The linearized plasmids were then in vitro transcribed to sgRNA and Cas9 mRNA with MessageMAX T7 ARCA-Capped Message Transcription Kit (CellScript, Madison, Wis.) following the manufacturer's instruction. Synthesized Cas9 mRNA was added with the PolyA tail by Poly(A) Polymerase Tailing Kit (Epicentre, Madison, Wis.).

sgRNA was purified with mirVana miRNA Isolation Kit (Ambion, Grand Island, N.Y.) and Cas9 mRNA was purified by MEGAclear Kit (Ambion, Grand Island, N.Y.) following the instructions. RNA quality and quantity were inspected with spectrophotometry, and the RNA stored at −80° C. until use.

2.4 Brood Stock Spawning

Sexually mature Kansas random channel catfish females were implanted with luteinizing hormone releasing hormone analog (LHRHa) at 90 μg/kg body weight to facilitate ovulation. Eggs were stripped from two ovulating females into metal pie pans coated with grease (Crisco, Orrville, Ohio). Two male channel catfish (Kansas random and AR) (Dunham and Smitherman, 1984) were euthanized and the testes were macerated into saline (0.9% NaCl) to release sperm and produce a sperm homogenate.

2.5 Fertilization, Electroporation and Microinjection

Double electroporation was performed for each of the CRSPR/Cas9 plasmids groups that targeting the channel catfish LH gene and cfGnRH gene described above with a Baekon 2000 macromolecule transfer system (Baekon, Inc., Saratoga, Calif.) with parameters set at 6 kV, 27 pulses, 0.8 s burst, 4 cycles, 160 μs (Powers et al., 1991). Briefly, channel catfish sperm were electroporated with one of the CRISPR/Cas9 plasmids sets, then two hundred eggs were fertilized with the electroporated sperm. Sixty minutes later, embryos were collected and incubated in plasmid solution for 10 minutes, followed by the second electroporation. The same procedure was performed on the control group, but without plasmids.

sgRNA that targeted cfGnRH gene was also microinjected together with the Gas9 nuclease mRNA. Channel catfish eggs were fertilized with normal sperm, and incubated in fresh water for 50 min. One hundred eggs were picked and placed on a 10 ml petri dish. One hundred picogram sgRNA and three hundred picogram Cas9 mRNA mixture were injected into the blastodisc using the Eppendorf Microinjector 5242 system (Hamburg, Germany). The control group was microinjected with the same solution without RNAs.

Then embryos were moved into 10 L tubs filled with Holtfreter's solution (Bait and Dunham, 1996) containing 10 ppm doxycycline and incubated at 27° C. until hatch. Dead embryos were removed and water was changed daily. Channel catfish fry were then transferred into a recirculating system.

2.6 Sample Collection, DNA Extraction and Mutation Analysis

The pelvic fin and barbel of 6-month-old fingerlings were sampled for DNA analysis. Samples were digested with 100 μg/ml proteinase K followed by protein precipitation and DNA ethanol precipitation as described by Kurita et al. (2004). DNA quantity and quality were determined with gel electrophoresis and spectrophotometry.

Channel catfish LH gene β subunit specific primer and cfGnRH gene specific primers (Table 9) were designed and Roche Expand High FidelityPlus PCR System (Roche, Indianapolis, Ind.) was used to amplify these DNA samples. The PCR amplification procedure was as follows: initial denaturation for 2 min at 94° C.; followed by 35 cycles of 94° C. for 30 s, 60° C. for 30 s and 72° C. for 1 min; and a final elongation for 10 min at 72° C. PCR products were examined by gel electrophoresis.

TABLE 9

Primer sequences used for the amplification of luteinizing hormone (LH) β subunit and catfish type gonadotropin-releasing hormone (cfGnRH) in channel catfish (Ictalurus punctatus).

| Primer | Sequence (5'-3') | Product Size (bp) | Description |
|---|---|---|---|
| LH-F | AGGATGTCAGTGCCA GCTTC (SEQ ID NO: 9) | 572 | LH gene amplification and mutation analysis |
| LH-R | CTTGGAGTAAATGGA CTCGTTG (SEQ ID NO: 10) | | |
| GnRH-F | ATGGATGCTGTCTTT GTTTTCC (SEQ ID NO: 19) | 550 | cfGnRH gene amplification and mutation analysis |

Gene mutations were detected through the Cel-I mutation detection assay with SURVEYOR Mutation Detection Kit (Integrated DNA Technologies, Coralville, Iowa) as described by Miller et al. (2007). Briefly, PCR products were denatured and re-annealed as follows; 94° C. 10 min; 94° C. to 85° C.-2° C./s; 85° C. to 25° C.-0.1° C./s; cooling to 4° C.; then 1 μl Enhancer S and 1 μl Nuclease S was added into 5 μl of the products above and incubated at 42° C. for 30 min; The digested PCR products were resolved on 2% UltraPure Agrose-1000 high resolution agarose gel (invitrogen, Grand Island, N.Y.).

2.7 TA Clone and Sequencing

To identify the exact modification of each gene, PCR products amplified from each individual of different groups were purified with IsoPure DNA Purification Kit (Denville, Holliston, Mass.), then inserted into the vector of TOPO TA Cloning Kit for Sequencing (Invitrogen, Grand Island, N.Y.) and transformed into the One Shot TOP10F Chemically Competent E. coli (Invitrogen, Grand Island, N.Y.). Colonies were selected from a LB agar plate containing 100 μg/ml ampicillin.

Ten colonies corresponding to each individual carrying mutated genes were picked and amplified. The bacteria glycerol stock were added into 96-well plates and sent to Eurofins Genomics Company (Louisville, Ky.) for sequencing.

Upon receiving the results, the quality was checked and the sequences were aligned with the wild type channel catfish LH and cfGnRH genes using the online multiple sequence alignment tool Clustal Omega (http://www.ebi.ac.uk/Tools/msa/clustalo/), respectively.

2.8 Plasmid Integration Inspection

To determine the presence of plasmids integrated into the channel catfish genome or persisting in the cytoplasm, two pairs of specific primers (Table 10) for each of the CRISPR/LH-U6, CRISPR/GnRH-U6 and pCS2-nCas9n plasmids were designed to detect the plasmid DNA in corresponding mutated channel catfish. The amplification regions of primers were the CMV promoter region, U6 promoter region and the backbone of plasmids, respectively. The PCR procedure was the same as of amplifying LH and cfGnRH genes and products were inspected with electrophoresis.

TABLE 10

Primer sequences used for the detection of clustered regularly interspaced short palindromic repeats (CRISPR) and Cas9 plasmids targeting channel catfish (*Ictalurus punctatus*) luteinizing hormone (LH) gene and catfish type gonadotropin-releasing hormone (cfGnRH) gene.

| Primer | Sequence (5'-3') | Product Size (bp) | Description |
|---|---|---|---|
| LI1-F | GCCTATTTCCCATGATTCCT (SEQ ID NO: 21) | 145 | CRISPR/LH-U6 plasmids integration detection |
| LI1-R | ACTGCAAACTACCCAAGAAA (SEQ ID NO: 22) | | |
| LI2-F | ATTTCTTGGGTAGTTTGCAG (SEQ ID NO: 23) | 173 | CRISPR/LH-U6 plasmids integration detection |
| LI2-R | CTTTCAAGTTACGGTAAGCA (SEQ ID NO: 24) | | |
| GI1-F | TTCATCCATAGTTGCCTGAC (SEQ ID NO: 25) | 176 | CRISPR/GnRH-U6 plasmids integration detection |
| GI1-R | ATAAAGTTGCAGGACCACTT (SEQ ID NO: 26) | | |
| GI2-F | ATCTTACCGCTGTTGAGATC (SEQ ID NO: 27) | 183 | CRISPR/GnRH-U6 plasmids integration detection |
| GI2-R | ACGCTGGTGAAAGTAAAAGA (SEQ ID NO: 28) | | |
| CI1-F | CTTCCTAATACCGCCCATAG (SEQ ID NO: 29) | 222 | pCS2-nCas9n plasmids integration detection |
| CI1-R | AACGGATATGAATGGGCAAT (SEQ ID NO: 30) | | |
| CI2-F | AAACCAACAGGAAAGTGACT (SEQ ID NO: 31) | 233 | pCS2-nCas9n plasmids integration detection |
| CI2-R | CATTCCTCTGTCCTCAAACA (SEQ ID NO: 32) | | |

2.9 Statistical Analysis

Mutation rates and survival rates from different CRISPR/Cas9 sets were analyzed utilizing Fisher's Exact Test and Pearson's Chi-square Test (McDonald, 2014). All analyses were performed with statistical software R (version 3.1.3).

3. Results 3.1 Hatch Rate and Survival Rate

Two hundred eggs were double electroporated with the CRISPR/Cas9 plasmids targeting channel catfish LH gene, cfGnRH gene groups or with buffer only. In the LH mutation group, 46 eggs hatched (hatch rate 23.0%) (Table 11) and after 6 months, only 13 were still alive (survival rate 28.3%). A similar result was for the cfGnRH mutation group, with 42 eggs hatched (21.0%) and only 8 fingerlings were alive (19.1%) after 6 months. For the control group, 55 of 200 eggs hatched in the control group (27.5%) and 14 of them were alive (25.5%). There was no significant difference between the treatment and control groups for both embryo hatch rate (Pearson's Chi-square Test, p=0.295) and fry survival rate (Fisher's Exact Test, p=0.610).

TABLE 11

Comparison of the embryo hatch rate and fry survival rate for clustered regularly interspaced short palindromic repeats (CRISPR)/Cas9 targeting channel catfish (*Ictalurus punctatus*) luteinizing hotilione (LH) gene or catfish type gonadotropin-releasing hormone (cfGnRH) gene.

| Constructs and method | Eggs N | Fry N | Hatch rate (%) † | Fingerlings N | Survival rate (%)* |
|---|---|---|---|---|---|
| Electroporation | | | | | |
| CRISPR-LH | 200 | 46 | 23.0$^a$ | 13 | 28.3 |
| CRISPR-GnRH | 200 | 42 | 21.0$^a$ | 8 | 19.1 |
| Control | 200 | 55 | 27.5$^a$ | 14 | 25.5 |
| Microinjection | | | | | |
| CRISPR-GnRH | 100 | 9 | 9.0$^b$ | 4 | 44.4 |
| Control | 100 | 11 | 11.0$^b$ | 5 | 45.5 |

† Different letters indicate significant difference between electroporation and microinjection (p = 0.0004).
*No significant difference between electroporation and microinjection (p = 0.301).

One hundred eggs were microinjected with sgRNA and Cas9 mRNA targeting the cfGnRH gene. Only 9% hatched and after 6 months only 4 were alive (survival rate 44.4%). For the control group, 11% hatched and 5 survived (45.5%). There was no difference between these two groups for mutation or survival rate (Fisher's Exact Test, p=0.814). When comparing hatch rate and survival rate between electroporated and microinjected eggs and fry, embryo hatch rates were found to be different between these two techniques (Pearson's Chi-square Test, p=0.0004), however, there was no difference between the fry survival rates (Fisher's Exact Test, p=0.301).

3.2 Mutation Rate

Figure 27:
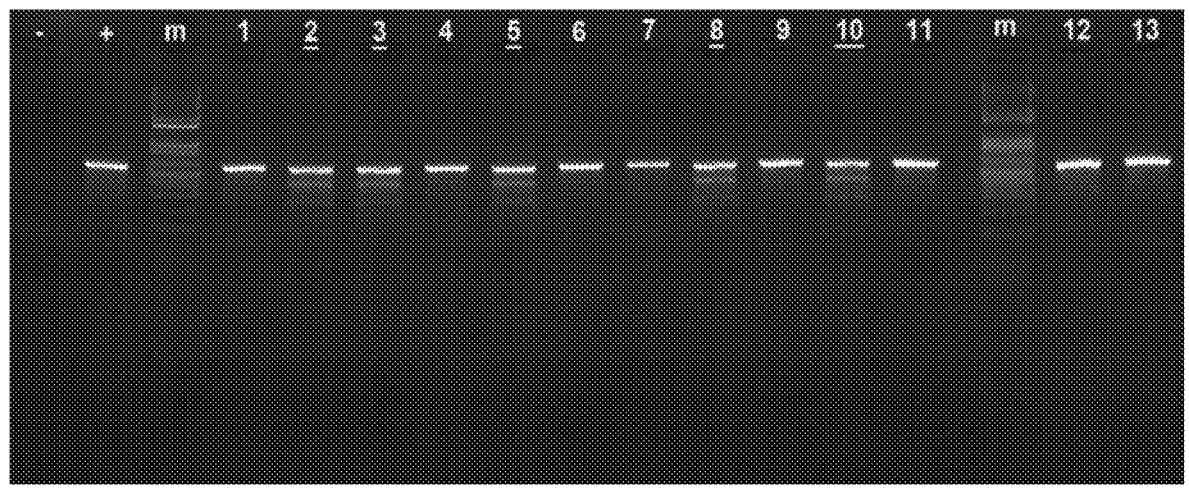
FIG. 27. Identification of edited luteinizing hormone (LH) gene in channel catfish (*Ictalurus punctatus*) electroporated with clustered regularly interspaced short palindromic repeats (CRISPR)/Cas9 plasmids using Cel-I mutation detection assay.
Figure 28:
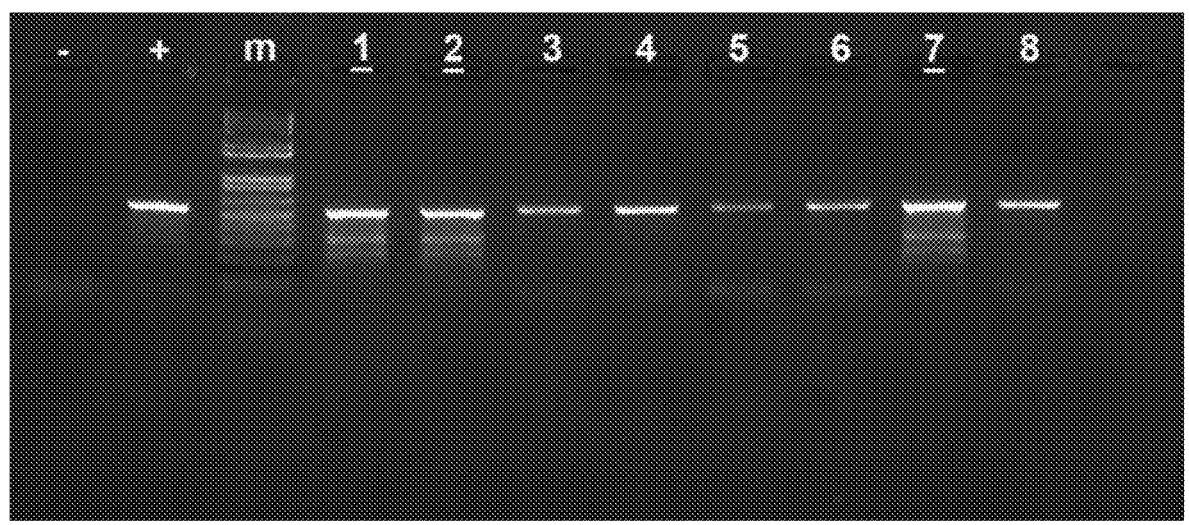
FIG. 28. Identification of edited catfish type gonadotropin-releasing hormone (cfGnRH) gene in channel catfish (*Ictalurus punctatus*) electroporated with clustered regularly interspaced short palindromic repeats (CRISPR)/Cas9 plasmids using Cel-I mutation detection assay.

Five of 13 individuals electroporated with CRISPR/Cas9 plasmids targeting channel catfish LH gene group and 3 of 8 individuals electroporated with CRISPR/Cas9 plasmids targeting channel catfish cfGnRH gene group (FIG. 27) carried the mutated gene (Table 12), as indicated by the clear three-banded pattern produced gel electrophoresis (FIG. 27), with mutation rates of 38.5% and 37.5%, respectively. No control fish were mutated.

When sgRNA and Cas9 mRNA was delivered via microinjection to target cfGnRH gene, 7 of 7 individuals were mutated (Table 12). The DNA band pattern was similar as that found in the TALEN experiment (FIG. 14, Chapter III). There were multiple bands on the gel, indicating cfGnRH gene was edited when compared with the control (FIG. 29). The mutation rate in this group was 100%.

TABLE 12

Comparison of luteinizing holmone (LH) gene and catfish type gonadotropin-releasing holinone (cfGnRH) gene mutation rate with electroporation and microinjection of clustered regularly interspaced short palindromic repeats CRISPR)/Cas9 system in channel catfish (*Ictalurus punctatus*).

| CRISPR | Procedure | N | N mutated | Mutation rate (%) |
|---|---|---|---|---|
| LH | Electroporation | 13 | 5 | 38.5 |
| GnRH | Electroporation | 8 | 3 | 37.5 |
| Control | Electroporation | 14 | 0 | 0 |
| GnRH | Microinjection | 7 | 7 | 100 |
| Control | Microinjection | 5 | 0 | 0 |

3.3 Sequence Modification of the Mutated Genes

In the LH gene mutated fingerlings, mutations occurred within the CRISPR targeting site. For all 5 individuals evaluated, only deletions existed based on the alignment result (FIG. 30).

The mutated cfGnRH gene generated by the CRISPR/Cas9 plasmids electroporation also showed only deletions based upon the results found from 3 individuals (FIG. 31).

In the microinjection experiment with CRISPR/Cas9 mRNA targeting cfGnRH gene, multiple types of mutations were generated. Four fish lost nucleotides at the cutting site, 1 had a one base substitution and the remainder had nucleotides insertions (FIG. 32).

Similar to the TALEN experiment, CRISPR/Cas9 showed high gene targeting specificity as all these mutations located within the expected targeting sites in the ORF. These mutations should lead to a frame-shift or early termination in transcription and disrupt normal gene functions.

3.5 CRISPR and Cas9 Plasmids Integration Evaluation

Figure 33:
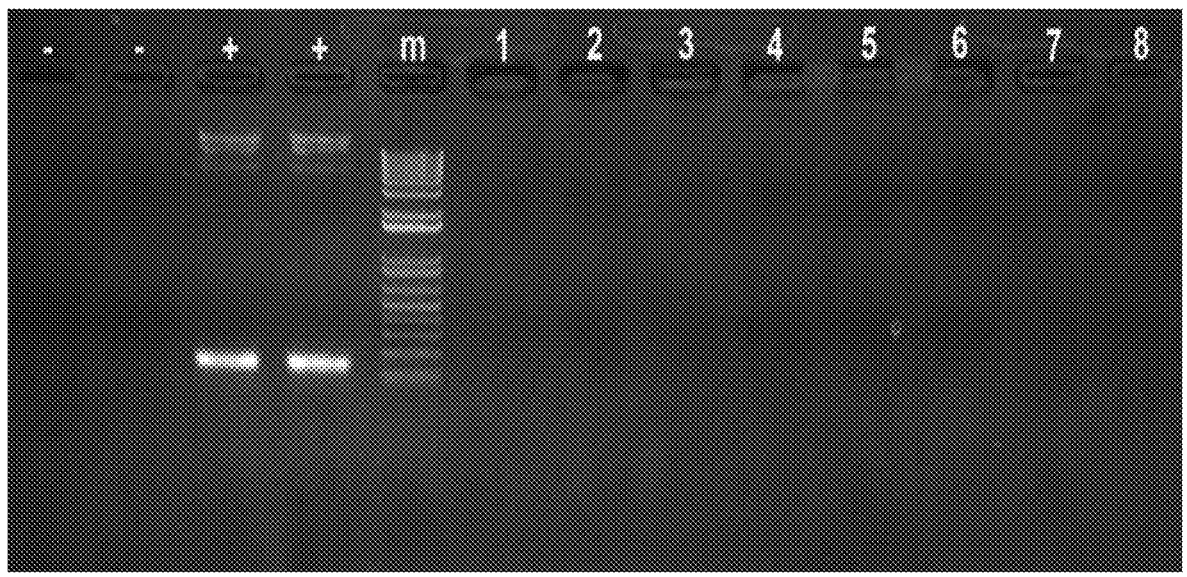
FIG. 33. PCR inspection of clustered regularly interspaced short palindromic repeats (CRISPR) plasmid (targeting the luteinizing hormone (LH) gene) integration into channel catfish (*Ictalurus punctatus*) genome.
Figure 34:
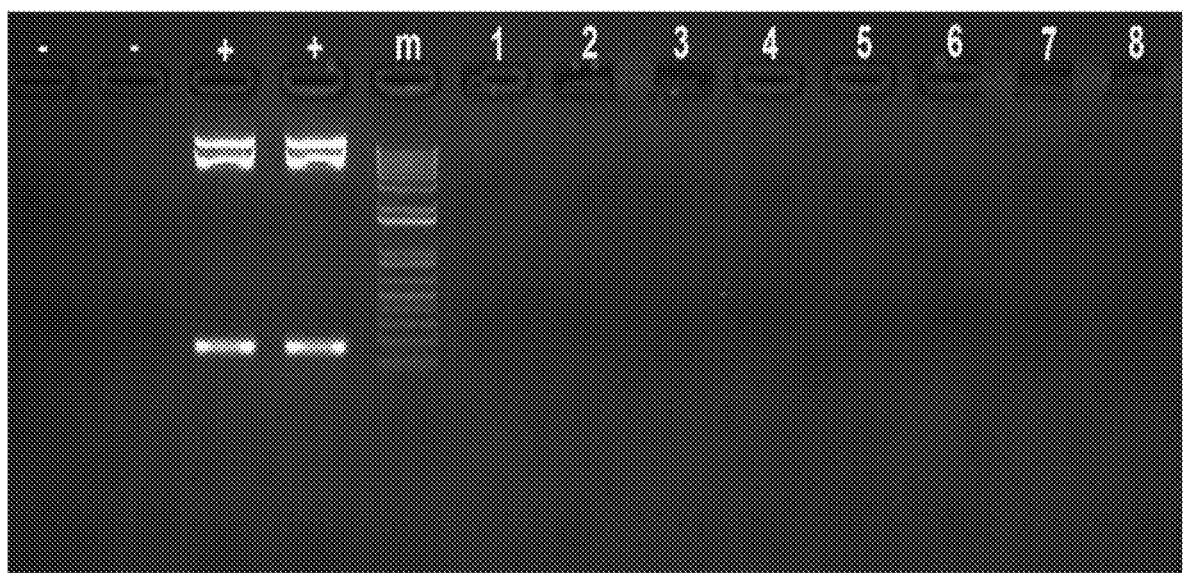
FIG. 34. PCR inspection of clustered regularly interspaced short palindromic repeats (CRISPR) plasmid (targeting the catfish type gonadotropin-releasing hormone (cfGnRH) gene) integration into channel catfish (*Ictalurus punctatus*) genome.
Figures 35, 36:
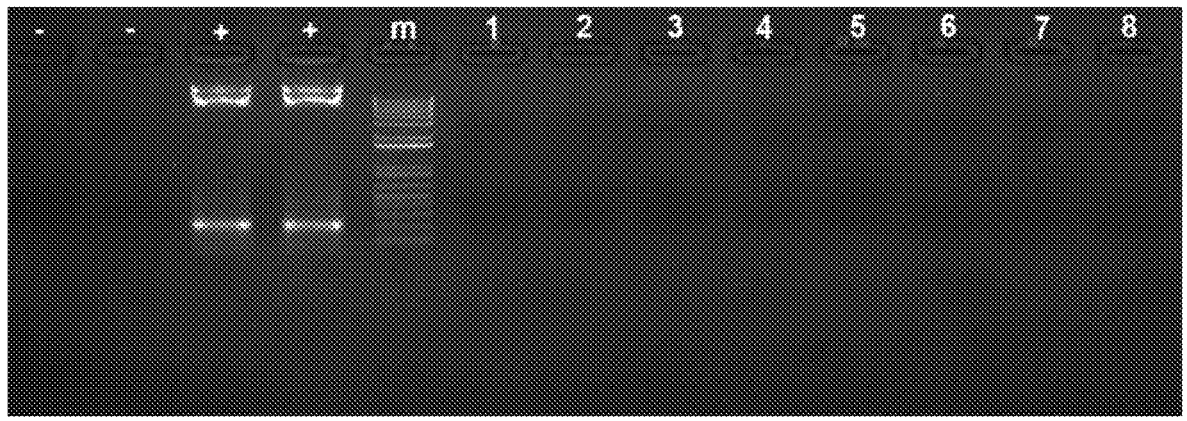
FIG. 35. PCR inspection of Cas9 plasmid integration into channel catfish (*Ictalurus punctatus*) genome.
FIG. 36. Amino acid alignments of cfGnRH TALEN sites showing mutations and predicted shifts, changes, and stops in the modified sequences.

Two pairs of specific primers for each of the CRISPR/LH-U6, CRISPR/GnRH-U6 and pCS2-nCas9n plasmids (Table 10) were used to detect the presence of plasmids DNA in the electroporation experiment in all of the mutated individuals. Similar to the results of the other experiments, no DNA of the CRISPR/LH-U6 (FIG. 33), CRISPR/GnRH-U6 (FIG. 34) and pCS2-nCas9n plasmid (FIG. 35) was detected with PCR All these results indicated neither the CRISPR plasmids nor the Cas9 plasmid was present in mutated channel catfish.

4 Discussion

Gene editing of channel catfish LH gene and cfGnRH gene, using the CRISPR/Cas9 technology with both electroporation and microinjection was accomplished. The mutation rate varied from ~38% with electroporation to 100% with microinjection. Additionally, embryo hatch rate and fry survival rate of the treatment groups and control groups did not differ. Thus, CRISPR/Cas9 technology did not have negative effects on the development of embryos and fry, and off-target mutations did not occur or were minimal and did not affect embryonic development and early survival. Several types of mutations were induced at the targeting sites with sequencing confirmation. This is the first time of using CRISPR/Cas9 to perform mutagenesis on genomic level in a major US aquaculture species.

CRISPR/Cas9 system is a newly developed technology but has been successfully utilized for targeted gene disruption in lots of animal models, such as nematode (*Caenorhabditis elegans*) (Friedland et al., 2013; Ward, 2015), fruit fly (*Drosophila*) (Gratz et al., 2013), frog (*Xenopus tropicalis*) (Nakayama et al., 2013), zebrafish (*Danio rerio*) (Chang et al., 2013; Hwang et al., 2013; Jao et al., 2013; Xiao et al., 2013), mice (Wang et al., 2013; Shen et al., 2013; Wu et al., 2015) and human cells (Cong et al., 2013; Hwang et al., 2013; Mali et al., 2013). The mutation rate varies in different studies which was as low as 2%-4% (Mali et al., 2013) to as high as 75%-99% (Jao et al., 2013). In the present experiment, the mutation rate for LH gene and cfGnRH gene were 38.5% and 37.5%, respectively, when using electroporation method, while the cfGnRH gene mutation rate was 100% when using microinjection. All these mutation rates are comparable with other studies and we successfully utilized the CRISPR/Cas9 technology in channel catfish gene mutagenesis.

Similar to the TALEN experiments, the sequences of the detected mutations in channel catfish DNA were all located in the CRISPR sgRNA binding sites within the gene ORF. The mutations should disrupt normal gene expression and likely will cause loss of gene function. Therefore, CRISPR/Cas9 system also has higher specificity in the targeted gene editing experiments, less off-target effect, and thus low cell toxicity, which is similar to what was achieved in zebrafish (Jao et al., 2013). 002511 Up to now, overwhelming majority of works using CRISPR/Cas9 system for targeted gene mutagenesis was done by microinjection (Chang et al., 2013; Jao et al., 2013). Recently, a few researchers edited genes mice by delivering CRISRP/Cas9 RNAs into zygotes with electroporation (Hashimoto and Takemoto, 2015; Qin et al., 2015), indicating electroporation is a good delivery approach of CRISPR/Cas9. Additionally, our studies using ZFN and TALEN successfully mutated channel catfish genes indicated electroporation with plasmids is also a promising method for gene editing.

In the present study, electroporation and microinjection with CRIPR/Cas9 system were compared. With electroporation of plasmids, channel catfish LH gene and cfGnRH gene mutation rate were 38.5% and 37.5%, respectively. When microinjection of mRNA was performed, the cfGnRH gene mutation rate rose to 100%, which is significant higher than that of electroporation (Fisher's Exact Test, p=0.0159). A potential explanation is that when using microinjection, it is assured each egg was successfully injected with CRISPR sgRNA and Cas9 mRNA, as the whole procedure was monitored under the microscope. But when using electroporation, it is possible that some eggs were not punched with micro holes in the egg shell or the plasmids did not reach the embryo proper. These eggs will not be affected by CRISPR/Cas9 resulting in microinjection providing a higher success rate.

However when comparing the egg hatch rate, there is significant difference between these two techniques. The egg hatch rates were 23.0% and 21.0% for LH and cfGnRH mutation groups with electroporation, respectively. This rate dropped to only 9.0% when using microinjection. Physical damage from the microneedle during microinjection is the likely cause of the reduced hatch.

CRISPR/Cas9 has proved to have a low incidence of off-target effects and a high gene mutation rate. If the editing of LH gene and cfGnRH gene of channel catfish realizes sterilization, it could be applied to overcome potential environmental and ecosystem risk, and profit the catfish farming industry.

5 Conclusion

We successfully performed CRISPR/Cas9 technology for targeted gene editing in channel catfish *I. punctatus* in this study. Both electroporation and microinjection approaches were applied and channel catfish reproductive related LH s subunit as well as cfGnRH gene were successfully mutated. This is the first time that CRISPR/Cas9 system has been used to edit genes of an aquaculture species in the US.

CRISPR/Cas9 system is a good technology for targeted gene manipulation and both electroporation and microinjection could induce high success rates. Whether to choose electroporation or microinjection could be decided by the aim of the study, and for large scale application, electroporation should be superior because of its simplicity and convenience.

Further study is needed to evaluate the fertility status of LH and cfGnRH mutated individuals when they reach sexual maturity. The restoration of fertility with hormone therapy will also need to be developed and evaluated to allow production of fertile brood stock to complete the reversible sterilization in channel catfish.

Example 4

Gene Editing of GnRH gene
Controls
Controls
There are five sets of Kansas Random controls were set up in the individual aquariums on June 5th. All the control fish were not injected any hormone during spawning season. 3 of 5 sets of controls spawned. Fertility was high 70-80%.

TABLE 13

Spawning results of control fish

| females | males | Eggs(g)/kg | Egg Size(Amount/g) | Total Weight of Eggs (g) | Hatching Rate | Pairing Date | Spawning Date | Pair Terminated |
|---|---|---|---|---|---|---|---|---|
| ♀KR1 | ♂KR1 | 95.71 | 17 | 67 | 70% | June 5$^{th}$ | June 11$^{th}$ | June 28$^{th}$ |
| ♀KR2 | ♂KR2 | 326.09 | 20 | 225 | 75% | June 5$^{th}$ | June 12$^{th}$ | June 28$^{th}$ |
| ♀KR3 | ♂KR3 | 204.29 | 30 | 143 | 78% | June 5$^{th}$ | June 13$^{th}$ | June 28$^{th}$ |
| ♀KR4 | ♂KR4 | / | / | / | / | June 5$^{th}$ | / | June 28$^{th}$ |
| ♀KR4 | ♂KR5 | / | / | / | / | June 5$^{th}$ | / | June 28$^{th}$ |

There are total 7 GnRH males and 4 GnRH females were paired with normal Kansas Random fish in individual aquariums to mate on June 5$^{th}$. All 7 of the Kansas Random females were implanted with 75 μg/kg of LHRHa. Four of the GnRH males were able to induce then normal females to spawn, but fertility was less than 3%, indicating near sterility for these males, especially considering they are likely mosaic. Only one of 4 GnRH females spawned, but she had high fertility. Spawning rate 25% was lower than controls, 60%, another indicator of sterility.

TABLE 14

Spawning results of GnRH gene edited fish

| GnRH fish No. | First pair | Eggs(g)/kg | Hatching Rate |
|---|---|---|---|
| ♂1 | ♀KR1 | 148.72 | <0.5% |
| ♂2 | ♀KR2 | 166.43 | <0.5% |
| ♂3 | ♀KR3 | 156.03 | 2% |
| ♂4 | ♀KR4 | 338.10 | 2.6% |
| ♂5 | ♀KR5 | 159.72 | 2.9% |
| ♂6 | ♀KR6 | / | / |
| ♂7 | ♀KR7 | / | / |
| ♂8 | ♀KR8 | / | / |
| ♂9 | ♀KR9 | / | / |
| ♀1 | ♂KR1 | 94.81 | 66% |
| ♀2 | ♂KR2 | / | / |
| ♀3 | ♂KR3 | / | / |
| ♀4 | ♂KR4 | / | / |
| ♀5 | ♂KR5 | / | / |

Total 16 KR females and 5 GnRH females were paired. 6 of 21 females spawned.

Gene Editing of FSH Gene
There are total 5 FSH males and 3 FSH females were paired with normal Kansas Random fish in individual baskets to mate on June 20$^{th}$. All the KR females were injected with a priming dose of 75 μg/kg LHRHa. Two FSH males were able to induce control KR females to lay eggs, and one FSH female spawned. In all 3 cases, hatching rate was 1% or less indicating a high degree of infertility.

TABLE 15

Spawning results of FSH gene edited fish

| FSH Fish No. | First Pair | Eggs(g)/kg | Hatching Rate | Pairing Date | Spawning Date |
|---|---|---|---|---|---|
| ♂1 | ♀KR1 | / | / | June 20$^{th}$ | / |
| ♂2 | ♀KR2 | 501.16 | <0.5% | June 20$^{th}$ | June 22$^{nd}$ |
| ♂3 | ♀KR3 | / | / | June 20$^{th}$ | / |
| ♂4 | ♀KR4 | / | / | June 20$^{th}$ | / |
| ♂5 | ♀KR5 | 156.42 | <0.5% | June 20$^{th}$ | June 22$^{nd}$ |

TABLE 15-continued

Spawning results of FSH gene edited fish

| FSH Fish No. | First Pair | Eggs(g)/kg | Hatching Rate | Pairing Date | Spawning Date |
|---|---|---|---|---|---|
| ♀1 | ♂KR1 | 425.50 | 1% | June 20$^{th}$ | June 28$^{th}$ |
| ♀2 | ♂KR2 | / | / | June 20$^{th}$ | / |
| ♀3 | ♂KR3 | / | / | June 20$^{th}$ | / |

Total 5 KR females, 1 Thompson females and 3 FSH females were paired. 3 of 9 females spawned.

Gene Editing of LH Gene
There are total 4 LH males and 6 LH females were paired with normal Kansas Random fish in individual baskets to mate on June 22$^{nd}$. All the KR females were injected with a priming dose of 75 μg/kg LHRHa. Only one LH male was able to induce the control female to spawn, but again the fertility was extremely low, 1%. The lack of spawning and low hatch is indicative of lack of capacity to reproduce.

TABLE 16

Spawning results of LH gene edited fish

| FSH Fish No. | First Pair | Eggs(g)/kg | Hatching Rate | Pairing Date | Spawning Date |
|---|---|---|---|---|---|
| ♂1 | ♀KR1 | 222.54 | 1% | June 22$^{nd}$ | June 24$^{th}$ |
| ♂2 | ♀KR2 | / | / | June 22$^{nd}$ | / |
| ♂3 | ♀KR3 | / | / | June 22$^{nd}$ | / |
| ♂4 | ♀KR4 | / | / | June 22$^{nd}$ | / |

TABLE 16-continued

Spawning results of LH gene edited fish

| FSH Fish No. | First Pair | Eggs(g)/kg | Hatching Rate | Pairing Date | Spawning Date |
|---|---|---|---|---|---|
| ♀1 | ♂KR1 | / | / | June 22$^{nd}$ | / |
| ♀2 | ♂KR2 | / | / | June 22$^{nd}$ | / |
| ♀3 | ♂KR3 | / | / | June 22$^{nd}$ | / |
| ♀4 | ♂KR4 | / | / | June 22$^{nd}$ | / |
| ♀5 | ♂KR5 | / | / | June 22$^{nd}$ | / |
| ♀6 | ♂KR6 | / | / | June 22$^{nd}$ | / |

In the event that there is an inconsistency between a definition of a term in the specification as compared to a definition of the term in a cited reference or the art, the term should be interpreted based on the definition in the specification.

Example 5

Introduction

Channel catfish (*Ictalurus punctatus*) is the most important freshwater aquaculture species in the US. Genetically enhanced fish that are sterile could both profit the catfish industry and overcome potential environmental risk of various types of domestic fish. Gene editing is a potentially powerful technology to produce sterile channel catfish.

Zinc Finger Nuclease (ZFN), Transcription Activator-like Effector Nuclease (TALEN) and Clustered Regularly Interspaced Short Palindromic Repeats (CRISPR)/Cas9 are three gene manipulation techniques that could create highly targeted double-strand breaks (DSBs) within targeted genes and enable the manipulation of the genome with unprecedented ease and precision. Gonadotropin-releasing hormone (GnRH), luteinizing hormone (LH) and follicle-stimulating hormone (FSH) are critical and play central roles in regulating gametogenesis and the production of gonadal hormones.

In this research, we intended to build a gene edited sterile channel catfish (*Ictalurus punctatus*). The development of germ cells and gonadal somatic cells may be inhibited. Fish mating experiments were utilized to evaluate the reproductive capability of gene edited catfish. Mutation analyses were employed on $F_1$ fish to verify the heredity of mutations. Reversal of sterility of gene edited sterile fish may be achievable. A hormone therapy regime will be developed and evaluated in the future to restore reproduction of sterile fish.

Methods

Plasmids described previously for encoding ZF, TALEN, and CRISPR/Cas9 nucleases were used (FIGS. 1, 9, 21, 22, 23, 24) in addition to the following:

Baekon 2000 macromolecule transfer system (Baekon, Inc., CA).

Roche Expand High Fidelity Plus PCR System (Roche, Indianapolis, Ind.)

Surveyor® Mutation Detection Kit (Integrated DNA Technologies, IA)

Mating experiments.

Wild type♀×Mutated♂, Mutated♀×Wild type♂

Mutated♀×Mutated♂

Hormone therapy.

GnRH gene edited fish: LHRHa implant

FSH gene edited fish: Gonadotropin from pregnant mare or human serum injection

LH gene edited fish: Carp LH injection

Results

For the GnRH gene mutated fish, total 7 mutant males and 4 mutant females were paired. 3 of 7 males fertilized the eggs. 1 of 4 females spawned (Table. 17).

TABLE 17

Spawning results of GnRH gene edited fish

| GnRH Fish No. | First pair | Eggs(g)/kg | Hatching Rate |
|---|---|---|---|
| ♂1 | ♀WT1 | 148.72 | <0.5% |
| ♂2 | ♀WT2 | 338.10 | 2% |
| ♂3 | ♀WT3 | 159.72 | 2.6% |
| ♂4 | ♀WT4 | / | 2.9% |
| ♂5 | ♀WT5 | / | / |
| ♂6 | ♀WT6 | / | / |
| ♂7 | ♀WT7 | / | / |
| ♀1 | ♂WT1 | 94.81 | 66% |
| ♀2 | ♂WT2 | / | / |
| ♀3 | ♂WT3 | / | / |
| ♀4 | ♂WT4 | / | / |

For the FSH gene mutated fish, total 5 mutant males and 3 mutant females were paired. 2 of 5 males fertilized the eggs. 1 of 3 females spawned (Table. 18).

TABLE 18

Spawning results of LH gene edited fish.

| FSH Fish No. | First Pair | Eggs(g)/kg | Hatching Rate |
|---|---|---|---|
| ♂1 | ♀WT1 | / | / |
| ♂2 | ♀WT2 | 501.16 | <0.5% |
| ♂3 | ♀WT3 | / | / |
| ♂4 | ♀WT4 | / | / |
| ♂5 | ♀WT5 | 156.42 | <0.5% |
| ♀1 | ♂WT1 | 425.50 | 1% |
| ♀2 | ♂WT2 | / | / |
| ♀3 | ♂WT3 | / | / |

For the LH gene mutated fish, total 4 mutant males and 6 mutant females were paired. I of 4 males fertilized the eggs. 0 of 6 females spawned (Table. 19). 17 pairs of LH mutants failed to spawn previously. Additional studies showed similar results with 25 males and 30 females mutated in LH being spawned but only one of them (a single male) fertilizing eggs. Of these eggs, only 1% were viable.

TABLE 19

Spawning results of LH gene edited fish

| LH Fish No. | First Pair | Eggs(g)/kg | Hatching Rate |
|---|---|---|---|
| ♂1 | ♀WT1 | 222.54 | 1% |
| ♂2 | ♀WT2 | / | / |
| ♂3 | ♀WT3 | / | / |
| ♂4 | ♀WT4 | / | / |
| ♀1 | ♂WT1 | / | / |
| ♀2 | ♂WT2 | / | / |
| ♀3 | ♂WT3 | / | / |
| ♀4 | ♂WT4 | / | / |
| ♀5 | ♂WT5 | / | / |
| ♀6 | ♂WT6 | / | / |

TABLE 20

Spawning results of control group

| females | males | Eggs(g)/kg | Hatching Rate |
|---|---|---|---|
| ♀KR1 | ♂WT1 | 95.71 | 70% |
| ♀KR2 | ♂WT2 | 326.09 | 75% |
| ♀KR3 | ♂WT3 | 204.29 | 78% |
| ♀KR4 | ♂WT4 | / | / |
| ♀KR4 | ♂WT5 | / | / |

The hatching rates of the most of the gene edited families were significantly lower than the controls. More fungus was found in the gene edited families.

The $F_1$ offspring were mutant fish. The individuals showed different types of mutations. GnRH, FSH and LH genes were successfully mutated in channel catfish through all three technologies, ZFN, TALEN and CRISPR/Cas9. In this study, the ovulation rate and the hatching rate were much lower for mutants than normal channel catfish. The mutations were transmitted to the $F_1$ generation.

It will be readily apparent to one skilled in the art that varying substitutions and modifications may be made to the methods and compositions disclosed herein. These methods and compositions may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the methods and compositions. Thus, it should be understood that although these methods and compositions have been illustrated by specific embodiments and optional features, modification and/or variation of the concepts herein disclosed may be resorted to by those skilled in the art, and that such modifications and variations are considered to be within the scope of the disclosed methods and compositions.

The invention claimed is:

1. A genetically modified *Ictalurus punctatus* that has been genetically modified to comprise a modified luteinizing hormone gene, wherein the genetically modified *Ictalurus punctatus* exhibits reduced reproduction relative to wild type *Ictalurus punctatus*, and wherein the modified luteinizing hormone gene is an endogenous gene that has been modified to comprise a mutation relative to the native gene sequence of the luteinizing hormone gene within the nucleotide sequence of SEQ ID NO:72 that results in a frameshift in the coding sequence of the gene.

2. A genetically modified *Ictalurus punctatus* that has been genetically modified to comprise a modified gonadotropin-releasing hormone gene, wherein the genetically modified *Ictalurus punctatus* exhibits reduced reproduction relative to wild type *Ictalurus punctatus*, and wherein the modified gonadotropin-releasing hormone gene is an endogenous gene that has been modified to comprise a mutation relative to the native gene sequence of the gonadotropin-releasing hormone gene within the nucleotide sequence of SEQ ID NO:78 that results in a frameshift in the coding sequence of the gene.

3. A method for reducing reproduction in a population of farmed *Ictalurus punctatus* in aquaculture confinement, the method comprising farming the *Ictalurus punctatus* of claim 1 in aquaculture confinement.

4. A method for reducing reproduction in a population of farmed *Ictalurus punctatus* in aquaculture confinement, the method comprising farming the *Ictalurus punctatus* of claim 2 in aquaculture confinement.

5. The *Ictalurus punctatus* of claim 1, wherein the mutation is a deletion.

6. The *Ictalurus punctatus* of claim 2, wherein the mutation is a deletion.

7. A genetically modified *Ictalurus punctatus* that has been genetically modified to comprise a modified luteinizing hormone gene, wherein the genetically modified *Ictalurus punctatus* exhibits reduced reproduction relative to wild type *Ictalurus punctatus*, and wherein the modified luteinizing hormone gene is an endogenous gene that has been modified to comprise a mutation relative to the native gene sequence of the luteinizing hormone gene that results in a frameshift in the coding sequence of the gene.

8. A genetically modified *Ictalurus punctatus* that has been genetically modified to comprise a modified gonadotropin-releasing hormone gene, wherein the genetically modified *Ictalurus punctatus* exhibits reduced reproduction relative to wild type *Ictalurus punctatus*, and wherein the modified gonadotropin-releasing hormone gene is an endogenous gene that has been modified to comprise a mutation relative to the native gene sequence of the gonadotropin-releasing hormone gene that results in a frameshift in the coding sequence of the gene.

9. A method for reducing reproduction in a population of farmed *Ictalurus punctatus* in aquaculture confinement, the method comprising farming the *Ictalurus punctatus* of claim 7 in aquaculture confinement.

10. A method for reducing reproduction in a population of farmed *Ictalurus punctatus* in aquaculture confinement, the method comprising farming the *Ictalurus punctatus* of claim 8 in aquaculture confinement.

11. The *Ictalurus punctatus* of claim 7, wherein the mutation is a deletion.

12. The *Ictalurus punctatus* of claim 8, wherein the mutation is a deletion.

\* \* \* \* \*

SEQUENCE LISTING

```
<160> NUMBER OF SEQ ID NOS: 139

<210> SEQ ID NO 1
<211> LENGTH: 38
<212> TYPE: DNA
<213> ORGANISM: Ictalurus punctatus
<220> FEATURE:
<221> NAME/KEY: misc_feature
<222> LOCATION: (1)..(38)
<223> OTHER INFORMATION: LH Target sites for ZFNs

<400> SEQUENCE: 1
cacagaaaca gtctcattaa caggttcgca gtgtggca                              38

<210> SEQ ID NO 2
<211> LENGTH: 36
<212> TYPE: DNA
<213> ORGANISM: Ictalurus punctatus
<220> FEATURE:
<221> NAME/KEY: misc_feature
<222> LOCATION: (1)..(36)
<223> OTHER INFORMATION: LH target sites for ZFNs

<400> SEQUENCE: 2
ctcattaaca ggttcgcagt gtggcagaat gtagct                                36

<210> SEQ ID NO 3
<211> LENGTH: 43
<212> TYPE: DNA
<213> ORGANISM: Ictalurus punctatus
<220> FEATURE:
<221> NAME/KEY: misc_feature
<222> LOCATION: (1)..(43)
<223> OTHER INFORMATION: LH target sites for ZFNs

<400> SEQUENCE: 3
```
ctcattaaca ggttcgcagt gtggcagaat gtagctttga cgc         43

<210> SEQ ID NO 4
<211> LENGTH: 52
<212> TYPE: DNA
<213> ORGANISM: Ictalurus punctatus
<220> FEATURE:
<221> NAME/KEY: misc_feature
<222> LOCATION: (1)..(52)
<223> OTHER INFORMATION: TALEN binding site and cleavage site for LH

<400> SEQUENCE: 4
tcttgatgaa ctccttctcc cccgctcaaa gctacattct gccacactgc ga         52

<210> SEQ ID NO 5
<211> LENGTH: 50
<212> TYPE: DNA
<213> ORGANISM: Ictalurus punctatus
<220> FEATURE:
<221> NAME/KEY: misc_feature
<222> LOCATION: (1)..(50)
<223> OTHER INFORMATION: TALEN binding site and cleavage site for FSH

<400> SEQUENCE: 5
taccaacatc tccatcaccg tggagagcga cgagtgtggc agctgcatca         50

<210> SEQ ID NO 6
<211> LENGTH: 52
<212> TYPE: DNA
<213> ORGANISM: Ictalurus punctatus
<220> FEATURE:
<221> NAME/KEY: misc_feature
<222> LOCATION: (1)..(52)
<223> OTHER INFORMATION: TALEN binding site and cleavage site for cfGnRH

<400> SEQUENCE: 6
ttcacctcgg aataaactct acaggctgaa agatctgctg gtgcacagct ca         52

<210> SEQ ID NO 7
<211> LENGTH: 44
<212> TYPE: DNA
<213> ORGANISM: Ictalurus punctatus
<220> FEATURE:
<221> NAME/KEY: misc_feature
<222> LOCATION: (1)..(44)
<223> OTHER INFORMATION: CRISPER target sequence for LH

<400> SEQUENCE: 7
ccttctcccc cgctcaaagc tacattctgc cacactgcga acct         44

<210> SEQ ID NO 8
<211> LENGTH: 44
<212> TYPE: DNA
<213> ORGANISM: Ictalurus punctatus
<220> FEATURE:
<221> NAME/KEY: misc_feature
<222> LOCATION: (1)..(44)
<223> OTHER INFORMATION: CRISPER target sequence for GnRH

<400> SEQUENCE: 8
tgccgaggac ctccggctac gtgtgtgatt acgtagatgt ttca         44

<210> SEQ ID NO 9
<211> LENGTH: 20
<212> TYPE: DNA
<213> ORGANISM: Ictalurus punctatus
<220> FEATURE:
<221> NAME/KEY: misc_feature -continued
<222> LOCATION: (1)..(20)
<223> OTHER INFORMATION: primer sequences used for the amplification of
      LH and the detection of ZFN plasmid integration in catfish

<400> SEQUENCE: 9
aggatgtcag tgccagcttc                                                 20

<210> SEQ ID NO 10
<211> LENGTH: 22
<212> TYPE: DNA
<213> ORGANISM: Ictalurus punctatus
<220> FEATURE:
<221> NAME/KEY: misc_feature
<222> LOCATION: (1)..(22)
<223> OTHER INFORMATION: primer sequences used for the amplification of
      LH and the detection of ZFN plasmid integration in catfish

<400> SEQUENCE: 10
cttggagtaa atggactcgt tg                                              22

<210> SEQ ID NO 11
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the amplification of
      LH and the detection of ZFN plasmid integtration in catfish

<400> SEQUENCE: 11
gtgtacggct acaggggaaa                                                 20

<210> SEQ ID NO 12
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the amplification of
      LH and the detection of ZFN plasmid integration in catfish

<400> SEQUENCE: 12
ttggggttga ggtgcttatc                                                 20

<210> SEQ ID NO 13
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the amplification of
      LH and the detection of ZFN plasmid integration in catfish

<400> SEQUENCE: 13
cgtgaccgag ttcaagttcc                                                 20

<210> SEQ ID NO 14
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the amplification of
      LH and the detection of ZFN plasmid integration in catfish

<400> SEQUENCE: 14
aagttgatct cgccgttgtt                                                  20

<210> SEQ ID NO 15
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the amplification of
      LH and the detection of ZFN plasmid integration in catfish

<400> SEQUENCE: 15
tacaaagacc atgacggtga                                                  20

<210> SEQ ID NO 16
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the amplification of
      LH and the detection of ZFN plasmid integration in catfish

<400> SEQUENCE: 16
tgcagattcg acactggaag                                                  20

<210> SEQ ID NO 17
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the amplification of
      LH beta subunit and cfGnRH

<400> SEQUENCE: 17
aggatgtcag tgccagcttc                                                  20

<210> SEQ ID NO 18
<211> LENGTH: 22
<212> TYPE: DNA
<213> ORGANISM: Ictalurus punctatus
<220> FEATURE:
<221> NAME/KEY: misc_feature
<222> LOCATION: (1)..(22)
<223> OTHER INFORMATION: primer sequences used for the amplification of
      LH beta subunit and cfGnRH

<400> SEQUENCE: 18
cttggagtaa atggactcgt tg                                               22

<210> SEQ ID NO 19
<211> LENGTH: 22
<212> TYPE: DNA
<213> ORGANISM: Ictalurus punctatus
<220> FEATURE:
<221> NAME/KEY: misc_feature
<222> LOCATION: (1)..(22)
<223> OTHER INFORMATION: primer serquences used for the amplification of
      LH beta subunit and cfGnRH

<400> SEQUENCE: 19
atggatgctg tctttgtttt cc                                               22

```
<210> SEQ ID NO 20
<211> LENGTH: 21
<212> TYPE: DNA
<213> ORGANISM: Ictalurus punctatus
<220> FEATURE:
<221> NAME/KEY: misc_feature
<222> LOCATION: (1)..(21)
<223> OTHER INFORMATION: primer sequences used for the amplification of
      LH beta subunit and cfGnRH

<400> SEQUENCE: 20
ccacacgaaa taaaggcaaa g                                              21

<210> SEQ ID NO 21
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the detection of
      CRISPER and Cas9 plamids targeting LH and cfGnRH genes

<400> SEQUENCE: 21
gcctatttcc catgattcct                                                20

<210> SEQ ID NO 22
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the detection of
      CRISPER and Cas9 plasmids targeting LH and cfGnRH genes

<400> SEQUENCE: 22
actgcaaact acccaagaaa                                                20

<210> SEQ ID NO 23
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the detection of
      CRISPER and Cas9 plasmids targeting LH and cfGnRH genes

<400> SEQUENCE: 23
atttcttggg tagtttgcag                                                20

<210> SEQ ID NO 24
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the detection of
      CRISPER and Cas9 plasmids targeting LH and cfGnRH genes

<400> SEQUENCE: 24
ctttcaagtt acggtaagca                                                20

<210> SEQ ID NO 25
<211> LENGTH: 20
<212> TYPE: DNA
```

```
<213> ORGANISM: Ictalurus punctatus
<220> FEATURE:
<221> NAME/KEY: misc_feature
<222> LOCATION: (1)..(20)
<223> OTHER INFORMATION: primer sequences used for the detection of
      CRISPER and Cas9 plasmids targeting LH and cfGnRH genes

<400> SEQUENCE: 25
ttcatccata gttgcctgac                                               20

<210> SEQ ID NO 26
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the detection of
      CRISPER and Cas9 plasmids targeting LH and cfGnRH genes

<400> SEQUENCE: 26
ataaagttgc aggaccactt                                               20

<210> SEQ ID NO 27
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the detection of
      CRISPER and Cas9 plasmids targeting LH and cfGnRH genes

<400> SEQUENCE: 27
atcttaccgc tgttgagatc                                               20

<210> SEQ ID NO 28
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the detection of
      CRISPER and Cas9 plasmids targeting LH and cfGnRH genes

<400> SEQUENCE: 28
acgctggtga aagtaaaaga                                               20

<210> SEQ ID NO 29
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the detection of
      CRISPER and Cas9 plasmids targeting LH and cfGnRH genes

<400> SEQUENCE: 29
cttcctaata ccgcccatag                                               20

<210> SEQ ID NO 30
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
```

```
<223> OTHER INFORMATION: primer sequences used for the detection of
      CRISPER and Cas9 plasmids targeting LH and cfGnRH genes

<400> SEQUENCE: 30
aacggatatg aatgggcaat                                              20

<210> SEQ ID NO 31
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the detection of
      CRISPER and Cas9 plasmids targeting LH and cfGnRH genes

<400> SEQUENCE: 31
aaaccaacag gaaagtgact                                              20

<210> SEQ ID NO 32
<211> LENGTH: 20
<212> TYPE: DNA
<213> ORGANISM: Ictalurus punctatus
<220> FEATURE:
<221> NAME/KEY: misc_feature
<222> LOCATION: (1)..(20)
<223> OTHER INFORMATION: primer sequences used for the detection of
      CRISPER and Cas9 plasmids targeting LH and cfGnRH genes

<400> SEQUENCE: 32
cattcctctg tcctcaaaca                                              20

<210> SEQ ID NO 33
<211> LENGTH: 46
<212> TYPE: DNA
<213> ORGANISM: Ictalurus punctatus

<400> SEQUENCE: 33
attctgccac actgcgaacc tgttaatgag actgtttctg tggaga                 46

<210> SEQ ID NO 34
<211> LENGTH: 28
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 34
ttttcttctc ctgtgtttct tgatgaac                                     28

<210> SEQ ID NO 35
<211> LENGTH: 29
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 35
ttttcttctc ctggtgtttc ttgatgaac                                    29

<210> SEQ ID NO 36
<211> LENGTH: 29
<212> TYPE: DNA
<213> ORGANISM: Artificial
<220> FEATURE:
```

<223> OTHER INFORMATION: Mutated Ictalurus punctatus luteinizing hormone
      gene

<400> SEQUENCE: 36
ttttcttctc ctgtgttttc ttgatgaac                                    29

<210> SEQ ID NO 37
<211> LENGTH: 29
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 37
ttttcttctc ctgtgttttc ttgatgaac                                    29

<210> SEQ ID NO 38
<211> LENGTH: 29
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 38
ttttcttctc ctgatgtttc ttgatgaac                                    29

<210> SEQ ID NO 39
<211> LENGTH: 30
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 39
ttttcttctc ctggtggttt cttgatgaac                                   30

<210> SEQ ID NO 40
<211> LENGTH: 30
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 40
ttttcttctc ctgatggttt cttgatgaac                                   30

<210> SEQ ID NO 41
<211> LENGTH: 30
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 41
ttttcttctc ctgtgtgttt cttgatgaac                                   30

<210> SEQ ID NO 42
<211> LENGTH: 28
<212> TYPE: DNA
<213> ORGANISM: Artificial
<220> FEATURE:
<223> OTHER INFORMATION: Mutated Ictalurus punctatus luteinizing hormone gene

<400> SEQUENCE: 42 tttctcctc ctgtgtttct tgatgaac                                28

<210> SEQ ID NO 43
<211> LENGTH: 26
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 43
ttttcttctc ctgtttcttg atgaac                                 26

<210> SEQ ID NO 44
<211> LENGTH: 29
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 44
ttttctcctc ctggtgtttc ttgatgaac                              29

<210> SEQ ID NO 45
<211> LENGTH: 60
<212> TYPE: DNA
<213> ORGANISM: Ictalurus punctatus

<400> SEQUENCE: 45
tgtttcttga tgaactcctt ctcccccgct caaagctaca ttctgccaca ctgcgaacct    60

<210> SEQ ID NO 46
<211> LENGTH: 59
<212> TYPE: DNA
<213> ORGANISM: Ictalurus punctatus

<400> SEQUENCE: 46
gtttcttgat gaactccttc tcccccgctc aaagctacat tctgccacac tgcgaacct     59

<210> SEQ ID NO 47
<211> LENGTH: 58
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 47
gtttcttgat gaactccttc tcccccgtca agctacatt ctgccacact gcgaacct       58

<210> SEQ ID NO 48
<211> LENGTH: 56
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 48
gtttcttgat gaactccttc tccgctcaaa gctacattct gccacactgc gaacct         56

```
<210> SEQ ID NO 49
<211> LENGTH: 56
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 49
gtttcttgat gaactccttc tcccctcaaa gctacattct gccacactgc gaacct      56

<210> SEQ ID NO 50
<211> LENGTH: 55
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 50
gtttcttgat gaactccttc tcgctcaaag ctacattctg ccacactgcg aacct         55

<210> SEQ ID NO 51
<211> LENGTH: 54
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 51
gtttcttgat gaactccttc tcctcaaagc tacattctgc cacactgcga acct           54

<210> SEQ ID NO 52
<211> LENGTH: 59
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 52
gtttcttgat gaactccttc tccccgctc taagctacat tctgccacac tgcgaacct      59

<210> SEQ ID NO 53
<211> LENGTH: 60
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 53
gtttcttgat gaactccttc tccccgcat caaagctaca ttctgccaca ctgcgaacct     60

<210> SEQ ID NO 54
<211> LENGTH: 61
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 54
gtttcttgat gaactccttc tcccccgct ccaaagctac attctgccac actgcgaacc     60
t                                                                    61
```

-continued

<210> SEQ ID NO 55
<211> LENGTH: 57
<212> TYPE: DNA
<213> ORGANISM: Ictalurus punctatus

<400> SEQUENCE: 55
gtcttaccaa catctccatc accgtggaga gcgacgagtg tggcagctgc atcactg        57

<210> SEQ ID NO 56
<211> LENGTH: 55
<212> TYPE: DNA
<213> ORGANISM: Artificial
<220> FEATURE:
<223> OTHER INFORMATION: Mutated Ictalurus punctatus follicle-
      stimulating hormone gene

<400> SEQUENCE: 56
gtcttaccaa catctccatc accgtggagc gacgagtgtg gcagctgcat cactg          55

<210> SEQ ID NO 57
<211> LENGTH: 54
<212> TYPE: DNA
<213> ORGANISM: Artificial
<220> FEATURE:
<223> OTHER INFORMATION: Mutated Ictalurus punctatus follicle-
      stimulating hormone gene

<400> SEQUENCE: 57
gtcttaccaa catctccatc accgtgagcg acgagtgtgg cagctgcatc actg           54

<210> SEQ ID NO 58
<211> LENGTH: 53
<212> TYPE: DNA
<213> ORGANISM: Artificial
<220> FEATURE:
<223> OTHER INFORMATION: Mutated Ictalurus punctatus follicle-
      stimulating hormone gene

<400> SEQUENCE: 58
gtcttaccaa catctccatc accggagcga cgagtgtggc agctgcatca ctg            53

<210> SEQ ID NO 59
<211> LENGTH: 53
<212> TYPE: DNA
<213> ORGANISM: Artificial
<220> FEATURE:
<223> OTHER INFORMATION: Mutated Ictalurus punctatus follicle-
      stimulating hormone gene

<400> SEQUENCE: 59
gtcttaccaa catctccatc accgtggaga cgagtgtggc agctgcatca ctg            53

<210> SEQ ID NO 60
<211> LENGTH: 57
<212> TYPE: DNA
<213> ORGANISM: Artificial
<220> FEATURE:
<223> OTHER INFORMATION: Mutated Ictalurus punctatus follicle-
      stimulating hormone gene

<400> SEQUENCE: 60
gtcttaccaa catctccatc accgtggaga gcgccgagtg tggcagctgc atcactg        57

<210> SEQ ID NO 61
<211> LENGTH: 56
<212> TYPE: DNA

```
<213> ORGANISM: Artificial
<220> FEATURE:
<223> OTHER INFORMATION: Mutated Ictalurus punctatus follicle-
      stimulating hormone gene

<400> SEQUENCE: 61
gtcttaccaa catctccatc accgtggaga gcgcgagtgt ggcagctgca tcactg      56

<210> SEQ ID NO 62
<211> LENGTH: 61
<212> TYPE: DNA
<213> ORGANISM: Artificial
<220> FEATURE:
<223> OTHER INFORMATION: Mutated Ictalurus punctatus follicle-
      stimulating hormone gene

<400> SEQUENCE: 62
gtcttaccaa catctccatc accgtggact cggagcgacg agtgtggcag ctgcatcact      60
g      61

<210> SEQ ID NO 63
<211> LENGTH: 62
<212> TYPE: DNA
<213> ORGANISM: Artificial
<220> FEATURE:
<223> OTHER INFORMATION: Mutated Ictalurus punctatus follicle-
      stimulating hormone gene

<400> SEQUENCE: 63
gtcttaccaa catctccatc accgtggaga gcgacgagtg cggtgtggca gctgcatcac      60
tg      62

<210> SEQ ID NO 64
<211> LENGTH: 59
<212> TYPE: DNA
<213> ORGANISM: Ictalurus punctatus

<400> SEQUENCE: 64
tgtttcacct cggaataaac tctacaggct gaaagatctg ctggtgcaca gctcataat      59

<210> SEQ ID NO 65
<211> LENGTH: 57
<212> TYPE: DNA
<213> ORGANISM: Artificial
<220> FEATURE:
<223> OTHER INFORMATION: Mutated Ictalurus punctatus gonadotropin-
      releasing  hormone gene

<400> SEQUENCE: 65
tgtttcacct cggaataaac tctaggctga aagatctgct ggtgcacagc tcataat      57

<210> SEQ ID NO 66
<211> LENGTH: 56
<212> TYPE: DNA
<213> ORGANISM: Artificial
<220> FEATURE:
<223> OTHER INFORMATION: Mutated Ictalurus punctatus gonadotropin-
      releasing  hormone gene

<400> SEQUENCE: 66
tgtttcacct cggaataaac tctggctgaa agatctgctg gtgcacagct cataat      56

<210> SEQ ID NO 67
<211> LENGTH: 56
<212> TYPE: DNA
```

<213> ORGANISM: Artificial
<220> FEATURE:
<223> OTHER INFORMATION: Mutated Ictalurus punctatus gonadotropin-
releasing hormone gene

<400> SEQUENCE: 67
tgtttcacct cggaataaac tctacaggaa agatctgctg gtgcacagct cataat    56

<210> SEQ ID NO 68
<211> LENGTH: 54
<212> TYPE: DNA
<213> ORGANISM: Artificial
<220> FEATURE:
<223> OTHER INFORMATION: Mutated Ictalurus punctatus gonadotropin-
releasing hormone gene

<400> SEQUENCE: 68
tgtttcacct cggaataaac tctatgaaag atctgctggt gcacagctca taat    54

<210> SEQ ID NO 69
<211> LENGTH: 60
<212> TYPE: DNA
<213> ORGANISM: Artificial
<220> FEATURE:
<223> OTHER INFORMATION: Mutated Ictalurus punctatus gonadotropin-
releasing hormone gene

<400> SEQUENCE: 69
tgtttcacct cggaataaac tctacaaggc tgaaagatct gctggtgcac agctcataat    60

<210> SEQ ID NO 70
<211> LENGTH: 59
<212> TYPE: DNA
<213> ORGANISM: Artificial
<220> FEATURE:
<223> OTHER INFORMATION: Mutated Ictalurus punctatus gonadotropin-
releasing hormone gene

<400> SEQUENCE: 70
tgtttcacct cggaataaac tctacagtct gatagatctg ctggtgcaca gctcataat    59

<210> SEQ ID NO 71
<211> LENGTH: 61
<212> TYPE: DNA
<213> ORGANISM: Artificial
<220> FEATURE:
<223> OTHER INFORMATION: Mutated Ictalurus punctatus gonadotropin-
releasing hormone gene

<400> SEQUENCE: 71
tgtttcacct cggaataaac tctacagggg ctgaaagatc tgctggtgca cagctcataa    60
t    61

<210> SEQ ID NO 72
<211> LENGTH: 49
<212> TYPE: DNA
<213> ORGANISM: Ictalurus punctatus

<400> SEQUENCE: 72
tgaactcctt ctcccccgct caaagctaca ttctgccaca ctgcgaacc    49

<210> SEQ ID NO 73
<211> LENGTH: 48
<212> TYPE: DNA
<213> ORGANISM: Artificial
<220> FEATURE:

<223> OTHER INFORMATION: Mutated Ictalurus punctatus luteinizing hormone
      gene

<400> SEQUENCE: 73
tgaactcctt ctcccccgct caaagctaca ttcgccacac tgcgaacc                48

<210> SEQ ID NO 74
<211> LENGTH: 47
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 74
tgaactcctt ctcccccgct caaagctaca ttctcacact gcgaacc                 47

<210> SEQ ID NO 75
<211> LENGTH: 45
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 75
tgaactcctt ctcccccgct caaagctaca ttcacactgc gaacc                   45

<210> SEQ ID NO 76
<211> LENGTH: 43
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 76
tgaactcctt ctcccccgct caaagctaca ttcactgcga acc                     43

<210> SEQ ID NO 77
<211> LENGTH: 41
<212> TYPE: DNA
<213> ORGANISM: Artificial
<220> FEATURE:
<223> OTHER INFORMATION: Mutated Ictalurus punctatus luteinizing hormone
      gene

<400> SEQUENCE: 77
tgaactcctt ctcccccgct caaagcgcca cactgcgaac c                       41

<210> SEQ ID NO 78
<211> LENGTH: 49
<212> TYPE: DNA
<213> ORGANISM: Ictalurus punctatus

<400> SEQUENCE: 78
gaaatgccga ggacctccgg ctacgtgtgt gattacgtag atgtttcac               49

<210> SEQ ID NO 79
<211> LENGTH: 47
<212> TYPE: DNA
<213> ORGANISM: Artificial
<220> FEATURE:
<223> OTHER INFORMATION: Mutated Ictalurus punctatus gonadotropin-
      releasing hormone gene

<400> SEQUENCE: 79

```
gaaatgccga ggacctccgg ctagtgtgtg gtacgtagat gtttcac          47
```

<210> SEQ ID NO 80
<211> LENGTH: 47
<212> TYPE: DNA
<213> ORGANISM: Artificial
<220> FEATURE:
<223> OTHER INFORMATION: Mutated Ictalurus punctatus gonadotropin-
      releasing hormone gene

<400> SEQUENCE: 80

```
gaaatgccga ggacctccgg ctagttgtgt gaacgtagat gtttcac          47
```

<210> SEQ ID NO 81
<211> LENGTH: 44
<212> TYPE: DNA
<213> ORGANISM: Artificial
<220> FEATURE:
<223> OTHER INFORMATION: Mutated Ictalurus punctatus gonadotropin-
      releasing hormone gene

<400> SEQUENCE: 81

```
gaaatgccga ggacctccgg ctagttgtga cgtagatgtt tcac             44
```

<210> SEQ ID NO 82
<211> LENGTH: 49
<212> TYPE: DNA
<213> ORGANISM: Ictalurus punctatus

<400> SEQUENCE: 82

```
gaaatgccga ggacctccgg ctacgtgtgt gattacgtag atgtttcac        49
```

<210> SEQ ID NO 83
<211> LENGTH: 48
<212> TYPE: DNA
<213> ORGANISM: Artificial
<220> FEATURE:
<223> OTHER INFORMATION: Mutated Ictalurus punctatus gonadotropin-
      releasing hormone gene

<400> SEQUENCE: 83

```
gaaatgccga ggacctccgg ctacgtgtgt gttacgtaga tgtttcac         48
```

<210> SEQ ID NO 84
<211> LENGTH: 47
<212> TYPE: DNA
<213> ORGANISM: Artificial
<220> FEATURE:
<223> OTHER INFORMATION: Mutated Ictalurus punctatus gonadotropin-
      releasing hormone gene

<400> SEQUENCE: 84

```
gaaatgccga ggacctccgg ctacgtgtga ttacgtagat gtttcac          47
```

<210> SEQ ID NO 85
<211> LENGTH: 47
<212> TYPE: DNA
<213> ORGANISM: Artificial
<220> FEATURE:
<223> OTHER INFORMATION: Mutated Ictalurus punctatus gonadotropin-
      releasing hormone gene

<400> SEQUENCE: 85

```
gaaatgccga ggacctccgg ctacgtgtgt gtacgtagat gtttcac          47
```

```
<210> SEQ ID NO 86
<211> LENGTH: 49
<212> TYPE: DNA
<213> ORGANISM: Artificial
<220> FEATURE:
<223> OTHER INFORMATION: Mutated Ictalurus punctatus gonadotropin-
      releasing hormone gene

<400> SEQUENCE: 86
gaaatgccga ggacctccgg ctacgtgtgt gtttacgtag atgtttcac           49

<210> SEQ ID NO 87
<211> LENGTH: 51
<212> TYPE: DNA
<213> ORGANISM: Artificial
<220> FEATURE:
<223> OTHER INFORMATION: Mutated Ictalurus punctatus gonadotrophin
      releasing hormone gene

<400> SEQUENCE: 87
gaaatgccga ggacctccgg ctacgtgtgt gatattacgt agatgtttca c         51

<210> SEQ ID NO 88
<211> LENGTH: 52
<212> TYPE: DNA
<213> ORGANISM: Artificial
<220> FEATURE:
<223> OTHER INFORMATION: Mutated Ictalurus punctatus gonadotrophin
      releasing hormone gene

<400> SEQUENCE: 88
gaaatgccga ggacctccgg ctacgtgtgt gatctttacg tagatgtttc ac        52

<210> SEQ ID NO 89
<211> LENGTH: 15
<212> TYPE: PRT
<213> ORGANISM: Ictalurus punctatus

<400> SEQUENCE: 89

Ser Pro Arg Asn Lys Leu Tyr Arg Leu Lys Asp Leu Leu Val His
1               5                   10                  15

<210> SEQ ID NO 90
<211> LENGTH: 6
<212> TYPE: PRT
<213> ORGANISM: Artificial
<220> FEATURE:
<223> OTHER INFORMATION: Mutated Ictalurus punctatus gonadotropin-
      releasing hormone

<400> SEQUENCE: 90

Ser Pro Arg Asn Lys Leu
1               5

<210> SEQ ID NO 91
<211> LENGTH: 15
<212> TYPE: PRT
<213> ORGANISM: Artificial
<220> FEATURE:
<223> OTHER INFORMATION: Mutated Ictalurus punctatus gonadotropin-
      releasing hormone

<400> SEQUENCE: 91

Ser Pro Arg Asn Lys Leu Trp Leu Lys Asp Leu Leu Val His Ser
1               5                   10                  15

<210> SEQ ID NO 92
```

```
<211> LENGTH: 15
<212> TYPE: PRT
<213> ORGANISM: Artificial
<220> FEATURE:
<223> OTHER INFORMATION: Mutated Ictalurus punctatus gonadotropin-
      releasing hormone

<400> SEQUENCE: 92

Ser Pro Arg Asn Lys Leu Tyr Arg Lys Asp Leu Leu Val His Ser
1               5                   10                  15

<210> SEQ ID NO 93
<211> LENGTH: 15
<212> TYPE: PRT
<213> ORGANISM: Artificial
<220> FEATURE:
<223> OTHER INFORMATION: Mutated Ictalurus punctatus gonadotropin-
      releasing hormone

<400> SEQUENCE: 93

Ser Pro Arg Asn Lys Leu Tyr Glu Arg Ser Ala Gly Ala Gln Leu
1               5                   10                  15

<210> SEQ ID NO 94
<211> LENGTH: 15
<212> TYPE: PRT
<213> ORGANISM: Artificial
<220> FEATURE:
<223> OTHER INFORMATION: Mutated Ictalurus punctatus gonadotropin-
      releasing hormone

<400> SEQUENCE: 94

Ser Pro Arg Asn Lys Leu Tyr Lys Leu Lys Asp Leu Leu Val His
1               5                   10                  15

<210> SEQ ID NO 95
<211> LENGTH: 15
<212> TYPE: PRT
<213> ORGANISM: Artificial
<220> FEATURE:
<223> OTHER INFORMATION: Mutated Ictalurus punctatus gonadotropin-
      releasing hormone

<400> SEQUENCE: 95

Ser Pro Arg Asn Lys Leu Tyr Ser Leu Ile Asp Leu Leu Val His
1               5                   10                  15

<210> SEQ ID NO 96
<211> LENGTH: 9
<212> TYPE: PRT
<213> ORGANISM: Artificial
<220> FEATURE:
<223> OTHER INFORMATION: Mutated Ictalurus punctatus gonadotropin-
      releasing hormone

<400> SEQUENCE: 96

Ser Pro Arg Asn Lys Leu Tyr Arg Gly
1               5

<210> SEQ ID NO 97
<211> LENGTH: 15
<212> TYPE: PRT
<213> ORGANISM: Ictalurus punctatus

<400> SEQUENCE: 97

Met Asn Ser Phe Ser Pro Ala Gln Ser Tyr Ile Leu Pro His Cys
1               5                   10                  15
```

<210> SEQ ID NO 98
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 98

Met Asn Ser Phe Ser Pro Val Lys Ala Thr Phe Cys His Thr Ala
1               5                   10                  15

<210> SEQ ID NO 99
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 99

Met Asn Ser Phe Ser Ala Gln Ser Tyr Ile Leu Pro His Cys Glu
1               5                   10                  15

<210> SEQ ID NO 100
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 100

Met Asn Ser Phe Ser Pro Gln Ser Tyr Ile Leu Pro His Cys Glu
1               5                   10                  15

<210> SEQ ID NO 101
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 101

Met Asn Ser Phe Ser Leu Lys Ala Thr Phe Cys His Thr Ala Asn
1               5                   10                  15

<210> SEQ ID NO 102
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 102

Met Asn Ser Phe Ser Ser Lys Leu His Ser Ala Thr Leu Arg Thr
1               5                   10                  15

<210> SEQ ID NO 103
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 103

Met Asn Ser Phe Ser Pro Ala Leu Ser Tyr Ile Leu Pro His Cys
1               5                   10                  15

<210> SEQ ID NO 104
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 104

Met Asn Ser Phe Ser Pro Ala Ser Lys Leu His Ser Ala Thr Leu
1               5                   10                  15

<210> SEQ ID NO 105
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 105

Met Asn Ser Phe Ser Pro Arg Ser Lys Ala Thr Phe Cys His Thr
1               5                   10                  15

<210> SEQ ID NO 106
<211> LENGTH: 15
<212> TYPE: PRT
<213> ORGANISM: Ictalurus punctatus

<400> SEQUENCE: 106

Met Ser Val Pro Ala Ser Ser Phe Leu Leu Leu Cys Phe Leu Met
1               5                   10                  15

<210> SEQ ID NO 107
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 107

Met Ser Val Pro Ala Ser Ser Phe Leu Leu Leu Val Phe Leu Asp
1               5                   10                  15

<210> SEQ ID NO 108
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 108

Met Ser Val Pro Ala Ser Ser Phe Leu Leu Leu Trp Phe Leu Asp
1               5                   10                  15

<210> SEQ ID NO 109
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 109

Met Ser Val Pro Ala Ser Ser Phe Leu Leu Leu Cys Phe Leu Asp
1               5                   10                  15

<210> SEQ ID NO 110
<211> LENGTH: 15
<212> TYPE: PRT

-continued

<213> ORGANISM: Artificial
<220> FEATURE:
<223> OTHER INFORMATION: Mutated Ictalurus punctatus luteinizing hormone

<400> SEQUENCE: 110

Met Ser Val Pro Ala Ser Ser Phe Leu Leu Leu Met Phe Leu Asp
1               5                   10                  15

<210> SEQ ID NO 111
<211> LENGTH: 14
<212> TYPE: PRT
<213> ORGANISM: Artificial
<220> FEATURE:
<223> OTHER INFORMATION: Mutated Ictalurus punctatus luteinizing hormone

<400> SEQUENCE: 111

Met Ser Val Pro Ala Ser Ser Phe Leu Leu Leu Val Val Ser
1               5                   10

<210> SEQ ID NO 112
<211> LENGTH: 14
<212> TYPE: PRT
<213> ORGANISM: Artificial
<220> FEATURE:
<223> OTHER INFORMATION: Mutated Ictalurus punctatus luteinizing hormone

<400> SEQUENCE: 112

Met Ser Val Pro Ala Ser Ser Phe Leu Leu Leu Met Val Ser
1               5                   10

<210> SEQ ID NO 113
<211> LENGTH: 14
<212> TYPE: PRT
<213> ORGANISM: Artificial
<220> FEATURE:
<223> OTHER INFORMATION: Mutated Ictalurus punctatus luteinizing hormone

<400> SEQUENCE: 113

Met Ser Val Pro Ala Ser Ser Phe Leu Leu Leu Cys Val Ser
1               5                   10

<210> SEQ ID NO 114
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 114

Met Ser Val Pro Ala Ser Ser Phe Leu Leu Leu Cys Phe Leu Met
1               5                   10                  15

<210> SEQ ID NO 115
<211> LENGTH: 15
<212> TYPE: PRT
<213> ORGANISM: Artificial
<220> FEATURE:
<223> OTHER INFORMATION: Mutated Ictalurus punctatus luteinizing hormone

<400> SEQUENCE: 115

Met Ser Val Pro Ala Ser Ser Phe Leu Leu Leu Phe Leu Asp Glu
1               5                   10                  15

<210> SEQ ID NO 116
<211> LENGTH: 15
<212> TYPE: PRT
<213> ORGANISM: Artificial

```
<220> FEATURE:
<223> OTHER INFORMATION: Mutated Ictalurus punctatus luteinizing hormone

<400> SEQUENCE: 116

Met Ser Val Pro Ala Ser Ser Phe Leu Leu Val Phe Leu Asp
1               5                   10                  15

<210> SEQ ID NO 117
<211> LENGTH: 15
<212> TYPE: PRT
<213> ORGANISM: Ictalurus punctatus

<400> SEQUENCE: 117

Leu Thr Asn Ile Ser Ile Thr Val Glu Ser Asp Glu Cys Gly Ser
1               5                   10                  15

<210> SEQ ID NO 118
<211> LENGTH: 15
<212> TYPE: PRT
<213> ORGANISM: Artificial
<220> FEATURE:
<223> OTHER INFORMATION: Mutated Ictalurus punctatus follicle-
      stimulating hormone

<400> SEQUENCE: 118

Leu Thr Asn Ile Ser Ile Thr Val Glu Arg Arg Val Trp Gln Leu
1               5                   10                  15

<210> SEQ ID NO 119
<211> LENGTH: 15
<212> TYPE: PRT
<213> ORGANISM: Artificial
<220> FEATURE:
<223> OTHER INFORMATION: Mutated Ictalurus punctatus follicle-
      stimulating hormone

<400> SEQUENCE: 119

Leu Thr Asn Ile Ser Ile Thr Val Ser Asp Glu Cys Gly Ser Cys
1               5                   10                  15

<210> SEQ ID NO 120
<211> LENGTH: 15
<212> TYPE: PRT
<213> ORGANISM: Artificial
<220> FEATURE:
<223> OTHER INFORMATION: Mutated Ictalurus punctatus follicle-
      stimulating hormone

<400> SEQUENCE: 120

Leu Thr Asn Ile Ser Ile Thr Gly Ala Thr Ser Val Ala Ala Ala
1               5                   10                  15

<210> SEQ ID NO 121
<211> LENGTH: 15
<212> TYPE: PRT
<213> ORGANISM: Artificial
<220> FEATURE:
<223> OTHER INFORMATION: Mutated Ictalurus punctatus follicle-
      stimulating hormone

<400> SEQUENCE: 121

Leu Thr Asn Ile Ser Ile Thr Val Glu Thr Ser Val Ala Ala Ala
1               5                   10                  15

<210> SEQ ID NO 122
<211> LENGTH: 15
<212> TYPE: PRT
```

```
<213> ORGANISM: Artificial
<220> FEATURE:
<223> OTHER INFORMATION: Mutated Ictalurus punctatus follicle-
      stimulating hormone

<400> SEQUENCE: 122

Leu Thr Asn Ile Ser Ile Thr Val Glu Ser Ala Glu Cys Gly Ser
1               5                   10                  15

<210> SEQ ID NO 123
<211> LENGTH: 15
<212> TYPE: PRT
<213> ORGANISM: Artificial
<220> FEATURE:
<223> OTHER INFORMATION: Mutated Ictalurus punctatus follicle-
      stimulating hormone

<400> SEQUENCE: 123

Leu Thr Asn Ile Ser Ile Thr Val Glu Ser Gly Glu Cys Gly Ser
1               5                   10                  15

<210> SEQ ID NO 124
<211> LENGTH: 15
<212> TYPE: PRT
<213> ORGANISM: Artificial
<220> FEATURE:
<223> OTHER INFORMATION: Mutated Ictalurus punctatus follicle-
      stimulating hormone

<400> SEQUENCE: 124

Leu Thr Asn Ile Ser Ile Thr Val Asp Ser Asp Glu Cys Gly Ser
1               5                   10                  15

<210> SEQ ID NO 125
<211> LENGTH: 15
<212> TYPE: PRT
<213> ORGANISM: Artificial
<220> FEATURE:
<223> OTHER INFORMATION: Mutated Ictalurus punctatus follicle-
      stimulating hormone

<400> SEQUENCE: 125

Leu Thr Asn Ile Ser Ile Thr Val Glu Ser Asp Glu Cys Gly Val
1               5                   10                  15

<210> SEQ ID NO 126
<211> LENGTH: 20
<212> TYPE: DNA
<213> ORGANISM: Artificial
<220> FEATURE:
<223> OTHER INFORMATION: Forward primer for amplifying follicle-
      stimulating hormone gene of Ictalurus punctatus

<400> SEQUENCE: 126
cacaactcca gctgtgacaa                                              20

<210> SEQ ID NO 127
<211> LENGTH: 20
<212> TYPE: DNA
<213> ORGANISM: Artificial
<220> FEATURE:
<223> OTHER INFORMATION: Reverse primer for amplifying follicle-
      stimulating hormone gene of Ictalurus punctatus

<400> SEQUENCE: 127
cagaattccg tggccattta                                              20
```

```
<210> SEQ ID NO 128
<211> LENGTH: 18
<212> TYPE: DNA
<213> ORGANISM: Artificial
<220> FEATURE:
<223> OTHER INFORMATION: Forward primer for detecting integration of
      lutenizing hormone plasmid of Ictalurus punctatus

<400> SEQUENCE: 128
aacaacaacg gcggtaag                                                   18

<210> SEQ ID NO 129
<211> LENGTH: 20
<212> TYPE: DNA
<213> ORGANISM: Artificial
<220> FEATURE:
<223> OTHER INFORMATION: Reverse primer for detecting integration of
      lutenizing hormone plasmid of Ictalurus punctatus

<400> SEQUENCE: 129
ttccctccat tgttattcgc                                                 20

<210> SEQ ID NO 130
<211> LENGTH: 20
<212> TYPE: DNA
<213> ORGANISM: Artificial
<220> FEATURE:
<223> OTHER INFORMATION: Forward primer for detecting integration of
      lutenizing hormone plasmid of Ictalurus punctatus

<400> SEQUENCE: 130
gcgaataaca atggagggaa                                                 20

<210> SEQ ID NO 131
<211> LENGTH: 17
<212> TYPE: DNA
<213> ORGANISM: Artificial
<220> FEATURE:
<223> OTHER INFORMATION: Reverse primer for detecting integration of
      lutenizing hormone plasmid of Ictalurus punctatus

<400> SEQUENCE: 131
gtcgtgggat gcaatgg                                                    17

<210> SEQ ID NO 132
<211> LENGTH: 20
<212> TYPE: DNA
<213> ORGANISM: Artificial
<220> FEATURE:
<223> OTHER INFORMATION: Forward primer for detecting integration of
      follicle-stimulating hormone plasmid of Ictalurus punctatus

<400> SEQUENCE: 132
gcaaataata acggtggcaa                                                 20

<210> SEQ ID NO 133
<211> LENGTH: 18
<212> TYPE: DNA
<213> ORGANISM: Artificial
<220> FEATURE:
<223> OTHER INFORMATION: Reverse primer for detecting integration of
      follicle-stimulating hormone plasmid of Ictalurus punctatus

<400> SEQUENCE: 133
gtttccctcc gtcatgcg                                                   18

<210> SEQ ID NO 134
```

```
<211> LENGTH: 19
<212> TYPE: DNA
<213> ORGANISM: Artificial
<220> FEATURE:
<223> OTHER INFORMATION: Forward primer for detecting integration of
      follicle-stimulating hormone plasmid of Ictalurus punctatus

<400> SEQUENCE: 134
gcgaataaca atggaggga                                                19

<210> SEQ ID NO 135
<211> LENGTH: 20
<212> TYPE: DNA
<213> ORGANISM: Artificial
<220> FEATURE:
<223> OTHER INFORMATION: Reverse primer for detecting integration of
      follicle-stimulating hormone plasmid of Ictalurus punctatus

<400> SEQUENCE: 135
gccaccgtta ttatttgcaa                                               20

<210> SEQ ID NO 136
<211> LENGTH: 18
<212> TYPE: DNA
<213> ORGANISM: Artificial
<220> FEATURE:
<223> OTHER INFORMATION: Forward primer for detecting integration of
      gonadotropin-stimulating hormone plasmid of Ictalurus punctatus

<400> SEQUENCE: 136
aacaacaacg gcggtaag                                                 18

<210> SEQ ID NO 137
<211> LENGTH: 20
<212> TYPE: DNA
<213> ORGANISM: Artificial
<220> FEATURE:
<223> OTHER INFORMATION: Reverse primer for detecting integration of
      gonadotropin-stimulating hormone plasmid of Ictalurus punctatus

<400> SEQUENCE: 137
cccattattg ttcgcgattg                                               20

<210> SEQ ID NO 138
<211> LENGTH: 17
<212> TYPE: DNA
<213> ORGANISM: Artificial
<220> FEATURE:
<223> OTHER INFORMATION: Forward primer for detecting integration of
      gonadotropin-stimulating hormone plasmid of Ictalurus punctatus

<400> SEQUENCE: 138
gcatgacgga gggaaac                                                  17

<210> SEQ ID NO 139
<211> LENGTH: 20
<212> TYPE: DNA
<213> ORGANISM: Artificial
<220> FEATURE:
<223> OTHER INFORMATION: Reverse primer for detecting integration of
      gonadotropin-stimulating hormone plasmid of Ictalurus punctatus

<400> SEQUENCE: 139
ccattattgt tcgcgattga                                               20
```